US011369594B2

(12) United States Patent
Grange et al.

(10) Patent No.: US 11,369,594 B2
(45) Date of Patent: Jun. 28, 2022

(54) CYTOTOXIC ACTIN-TARGETING COMPOUNDS

(71) Applicant: Queen's University at Kingston, Kingston (CA)

(72) Inventors: Rebecca Grange, Kingston (CA); John Allingham, Kingston (CA); Andrew Craig, Kingston (CA); P. Andrew Evans, Kingston (CA); Madhu Aeluri, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 16/639,207

(22) PCT Filed: Aug. 17, 2018

(86) PCT No.: PCT/CA2018/051000
§ 371 (c)(1),
(2) Date: Feb. 14, 2020

(87) PCT Pub. No.: WO2019/033219
PCT Pub. Date: Feb. 21, 2019

(65) Prior Publication Data
US 2020/0306233 A1    Oct. 1, 2020

Related U.S. Application Data

(60) Provisional application No. 62/547,254, filed on Aug. 18, 2017.

(51) Int. Cl.
| | | |
|---|---|---|
| *A61K 31/45* | (2006.01) |
| *A61K 45/06* | (2006.01) |
| *A61K 47/36* | (2006.01) |
| *A61K 31/221* | (2006.01) |
| *A61K 31/25* | (2006.01) |
| *A61K 31/341* | (2006.01) |
| *A61K 31/4015* | (2006.01) |
| *A61K 31/397* | (2006.01) |
| *C07D 211/76* | (2006.01) |
| *C07D 207/27* | (2006.01) |
| *C07D 205/08* | (2006.01) |
| *C07D 307/46* | (2006.01) |
| *C07D 321/10* | (2006.01) |
| *C07C 235/28* | (2006.01) |
| *C07C 321/10* | (2006.01) |

(52) U.S. Cl.
CPC ............ *A61K 31/45* (2013.01); *A61K 31/221* (2013.01); *A61K 31/25* (2013.01); *A61K 31/341* (2013.01); *A61K 31/397* (2013.01); *A61K 31/4015* (2013.01); *A61K 45/06* (2013.01); *A61K 47/36* (2013.01); *C07C 235/28* (2013.01); *C07C 321/10* (2013.01); *C07D 205/08* (2013.01); *C07D 207/27* (2013.01); *C07D 211/76* (2013.01); *C07D 307/46* (2013.01)

(58) Field of Classification Search
None
See application file for complete search history.

(56) References Cited

PUBLICATIONS

Grant & Hackh's Chemical Dictionary (5th Ed. 1987) at p. 148.*
International Search Report and Written Opinion for corresponding International Application No. PCT/CA2018/051000 filed on Aug. 17, 2018.
Suenaga, K., et al., "Synthesis and actin-depolymerizing activity of mycalolide analogs", Tetrahedron Letters 45, pp. 5383-5386, (2004).
Suenaga, K. et al., "Synthesis and biological activity of mycalollide analogs", Tetrahedron 62, pp. 8278-8290, (2006).
Tanaka, J., et al., "Actin-Binding Toxin "Tail" Wags the Dog", Chemistry & Biology 15, pp. 205-207, (2008).
Panek, J.S., et al., "Total Synthesis of the Actin-Depolymerzing Agent (-)—Mycalolide A: Application of Chiral Silane-Based Bond Contruction Methodology", J.Am. Chem. Soc., vol. 122, pp. 11090-11097, (2000).
Kobayashi, K., et al., "Design, Synthesis, and Biological Evaluations of Aplyronine A-Mycalolide B Hybrid Compound", Organic Letters, vol. 14, No. 5. pp. 1290-1293, (2012).

* cited by examiner

*Primary Examiner* — Po-Chih Chen
(74) *Attorney, Agent, or Firm* — Angela Lyon

(57) ABSTRACT

A class of compounds useful in pharmaceutical compositions and methods for treating or preventing cancer is described. Analogs of Mycalolide B have been prepared and tested in breast and ovarian cancer cell lines. The compounds show utility for inhibition of survival and proliferation of tumor cells. The compounds have been shown to disrupt actin.

21 Claims, 18 Drawing Sheets

Fig. 1A-C

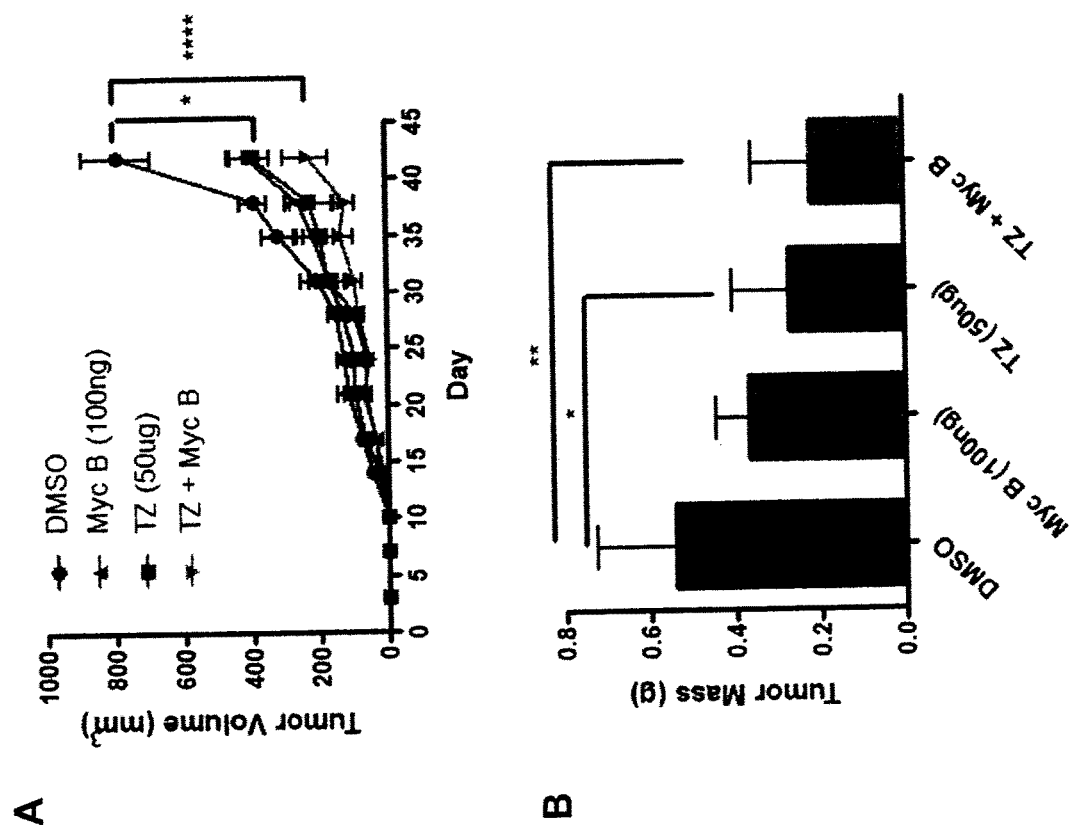
Fig. 3A-B

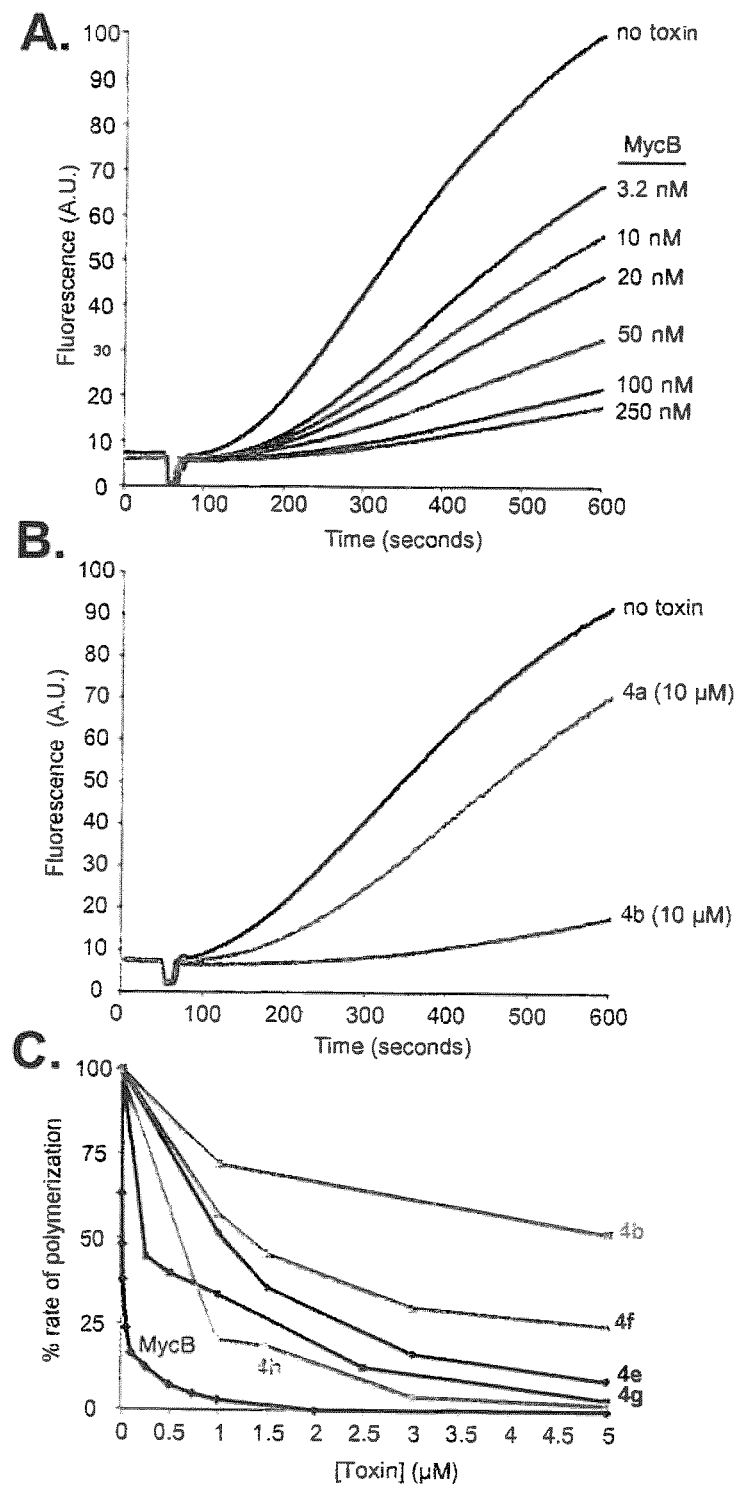
Fig. 4A-C

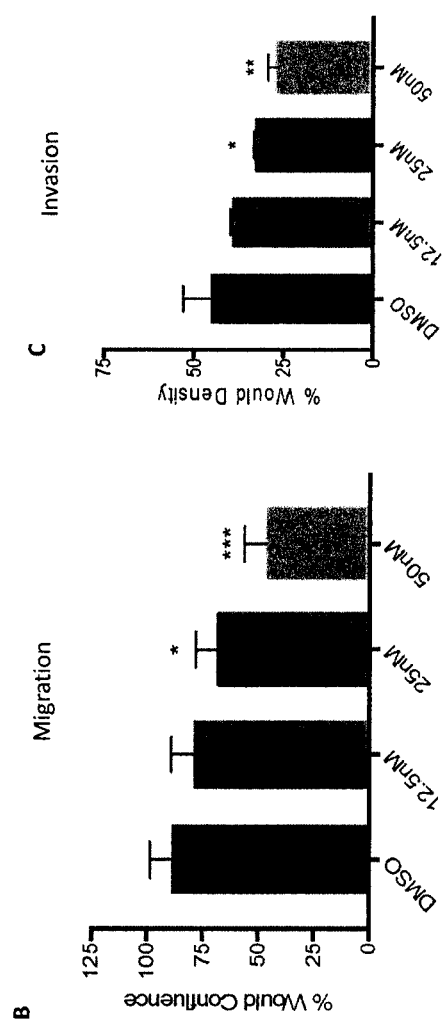
Fig. 5B-C

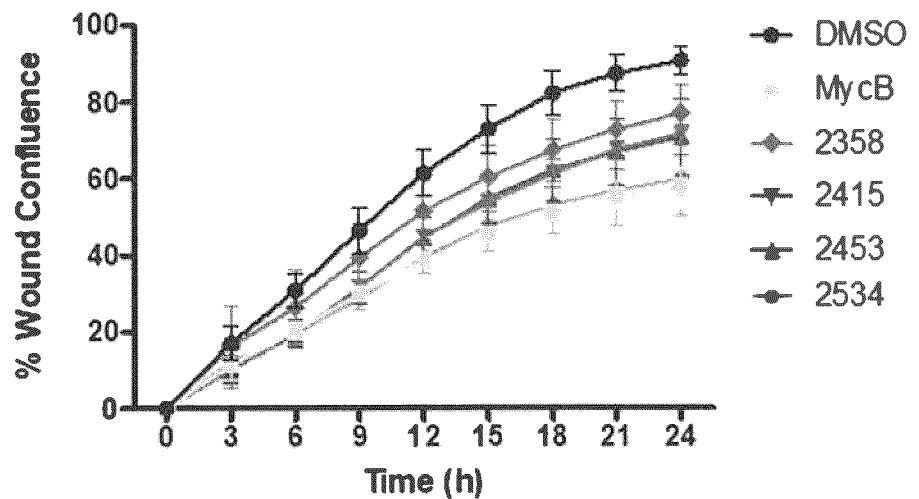
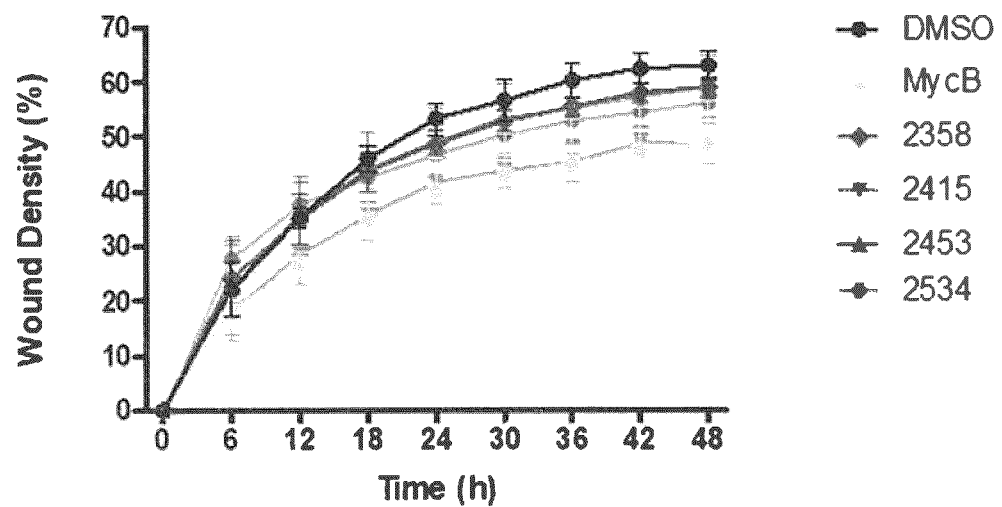
Fig. 6A-B

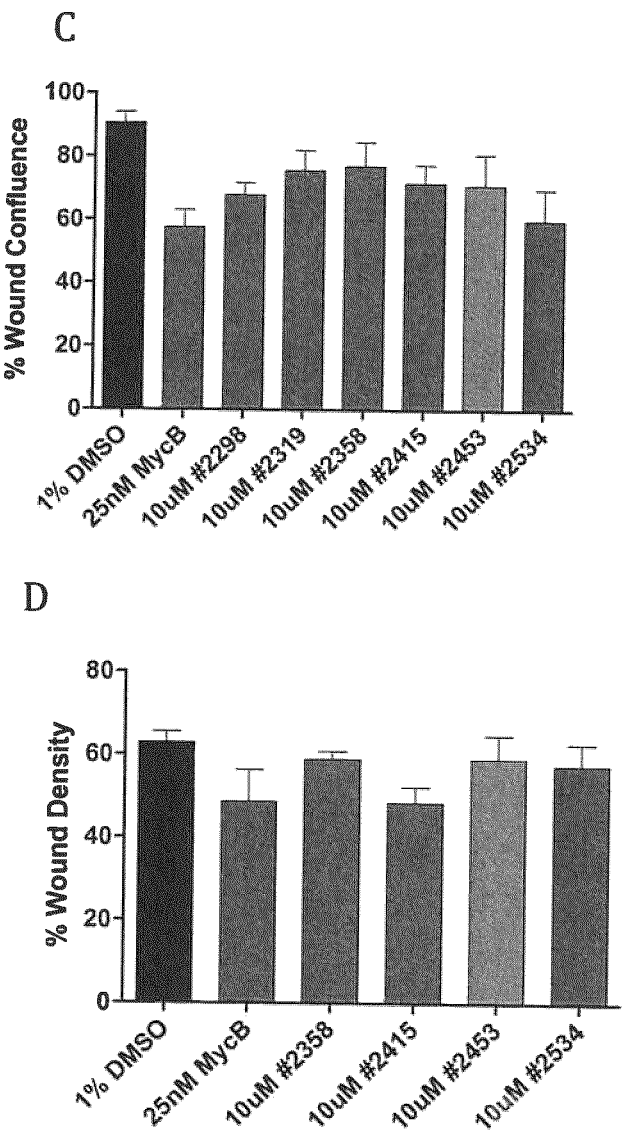
Fig. 6C-D

A
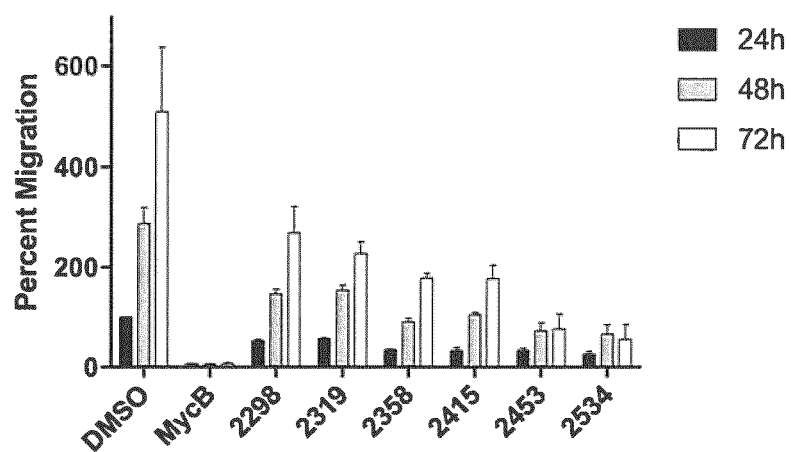
B
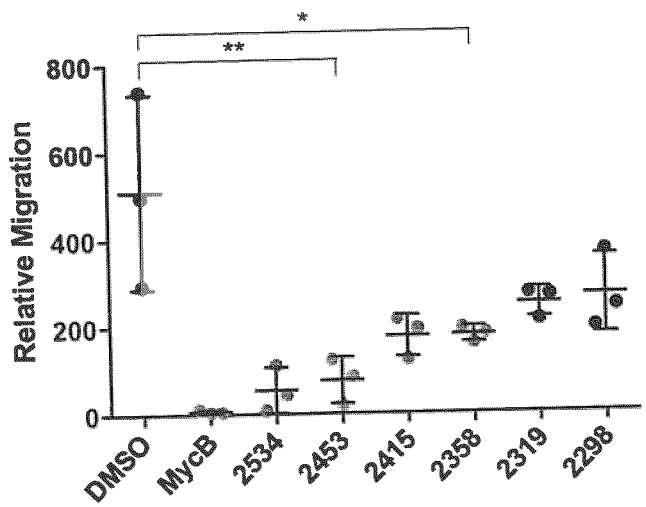
Fig. 7A-B

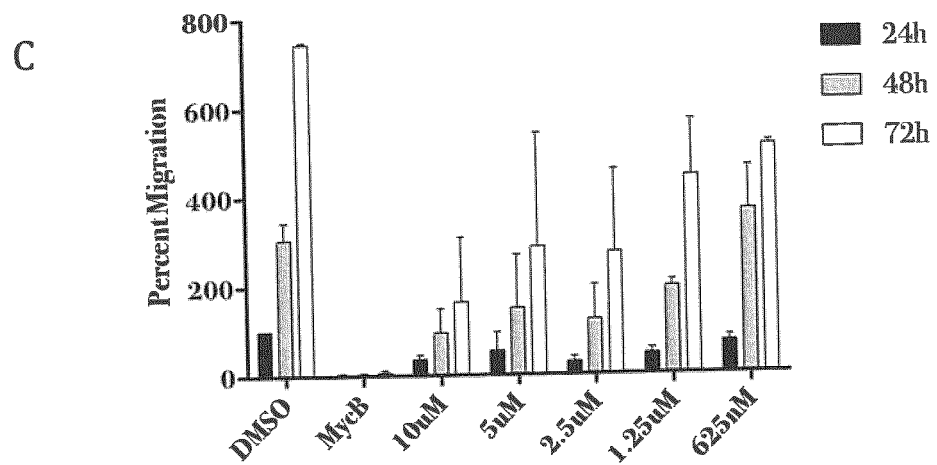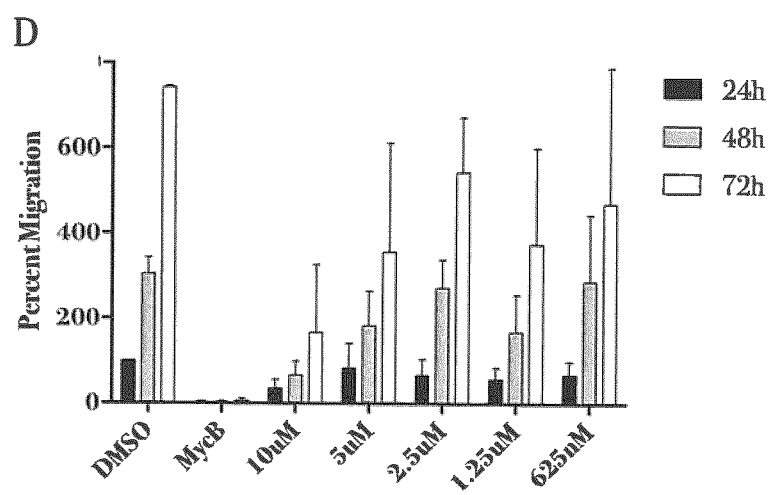
Fig. 7C-D

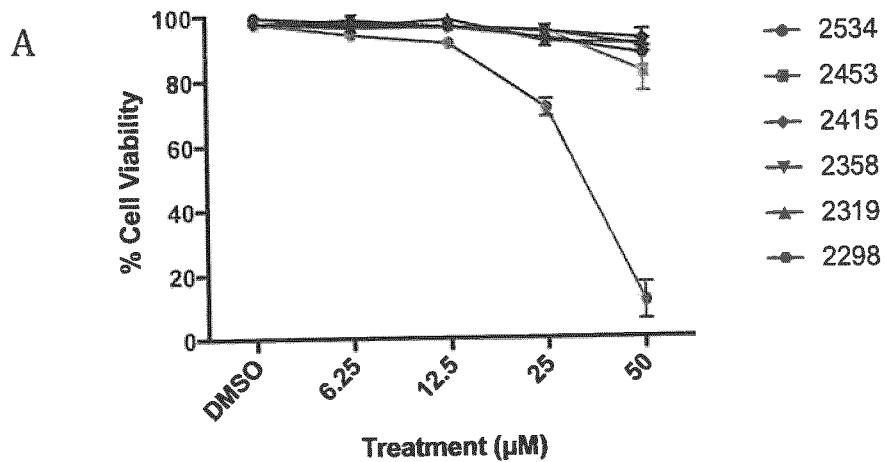
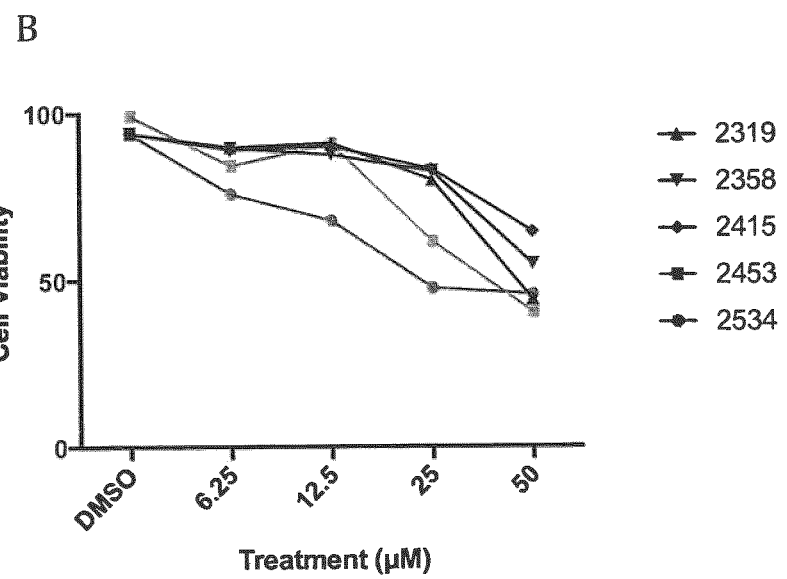
Fig. 8A-B

C 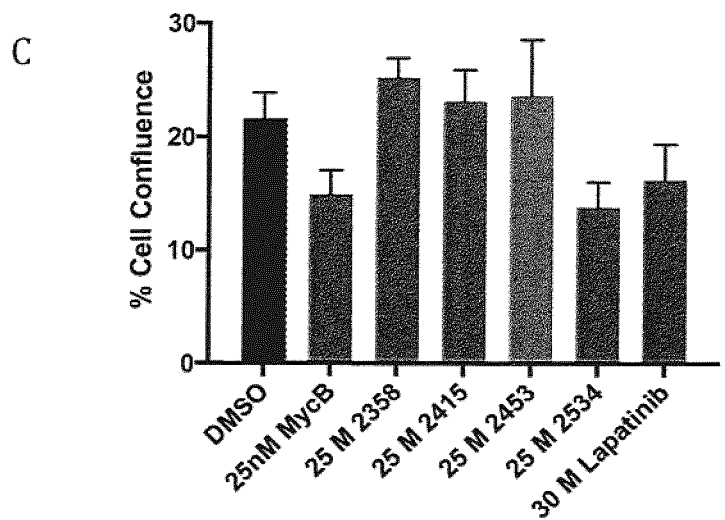
D 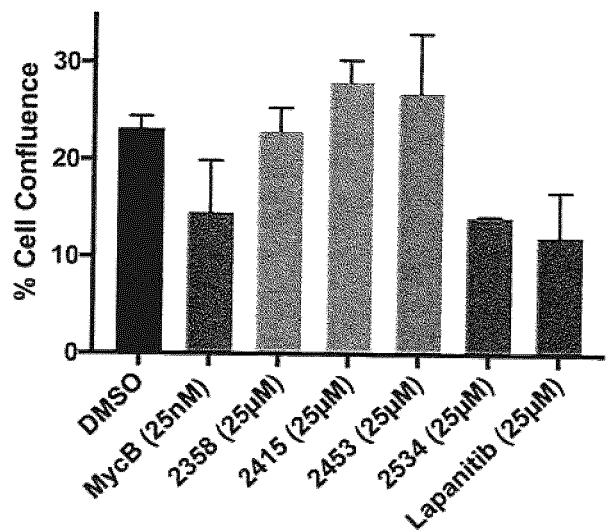
Fig. 8C-D

E
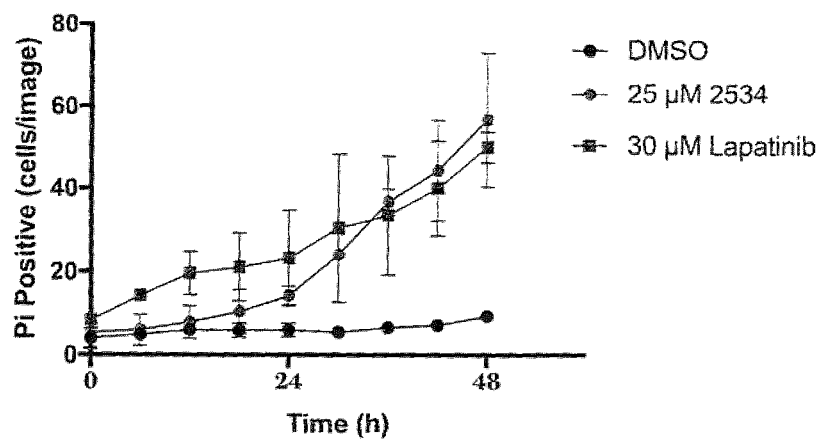
F
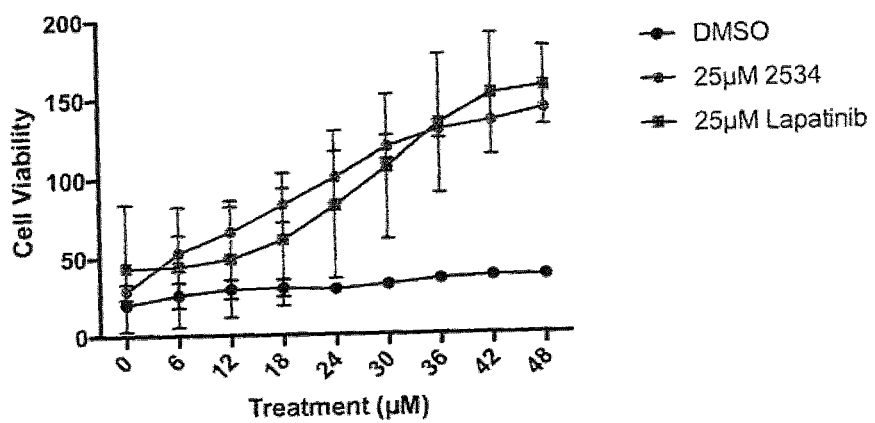
Fig. 8E-F

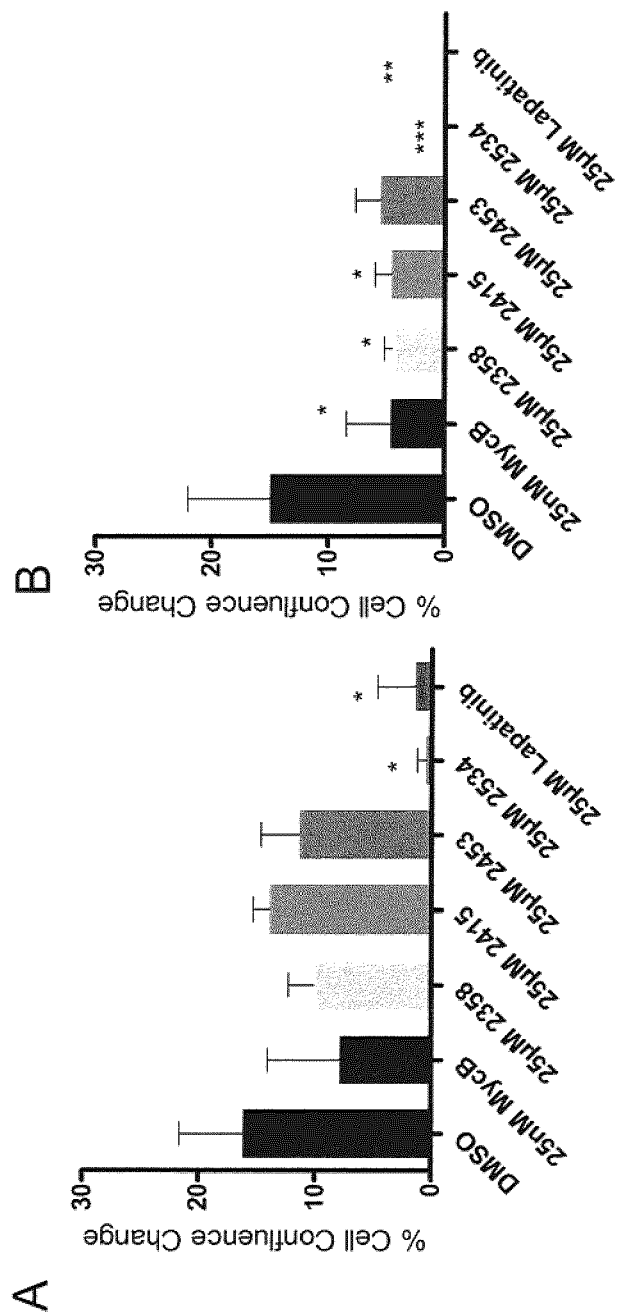
Fig 9A-B

CYTOTOXIC ACTIN-TARGETING COMPOUNDS

FIELD

The field pertains to synthesis of cytotoxic compounds that are analogs of mycalolides.

BACKGROUND

Actin is recognized as a strategic target for anticancer agents, although many of the naturally occurring agents are too complex and toxic to be utilized as drugs. Actin is a 43-kDa globular protein (G-actin) that can reversibly polymerize into helical filaments (F-actin), which form a three-dimensional network inside eukaryotic cells. G-actin is an ATPase that can be divided into four subdomains, where hydrolysis of ATP occurs deep within a cleft that separates subdomains 2 and 4. ATP hydrolysis is associated with G-actin's propensity to assemble into, or remain part of, F-actin polymers, such that the transition to the ADP-bound form reduces G-actin's filament-forming ability to permit F-actin depolymerization. The reversible polymerization of G-actin into F-actin in the cytosol, known as 'cytoskeleton remodeling', is critical for cytokinesis, cell division, vesicle and organelle movement, cell signaling, and maintenance of cell shape. Dynamic remodeling of actin filaments in the cytosol also drives shape changes, cell locomotion, and chemotactic migration that are vital to tissue development, wound healing, neuron migration, immune responses, and maintenance of homeostasis. However, these activities of actin can become aberrantly regulated in cancer, particulary those that spread to other sites (metastasis). It is postulated that anticancer drugs that interfere with actin may be able to disrupt tumor cell division, as well as tumor cell migration and invasion events that lead to metastatic disease. Hence, there is a need to develop new anticancer drugs that employ actin as their strategic target, which would constitute a new approach to chemotherapy.

SUMMARY

According to one aspect of the invention there is provided a compound of structural Formula (1),

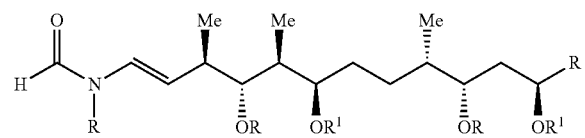

Formula (1)

wherein $R^1$ is independently H, —C(=O)R, —C(OR)(R)(R), —C(=O)NR$^2$R$^3$, —S(O$_2$)NR, —P(=O)(OR)$_2$, aliphatic and/or aryl moiety, and R, R$^2$, and R$^3$ are independently an aliphatic moiety and/or aryl moiety that is substituted or unsubstituted and optionally includes one or more heteroatoms.

According to another aspect of the invention there is provided a pharmaceutical composition, comprising an effective amount of a compound of Formula (1). In one embodiment, the compound of structural formula (1) of the above aspects is compound 4a, 4b, 4c, 4d, 4e, 4f, 4g, 4h, 11, 12, MA-02-058, MA-02-047, MA-02-044, or MA-02-046 as shown in Table 1, or a pharmaceutically acceptable salt thereof. In one embodiment, the pharmaceutical composition further comprises a pharmaceutically acceptable vehicle.

According to another aspect of the invention there is provided a method of treating and/or mitigating cancer, comprising administering to a subject a pharmaceutical composition comprising a compound of Formula (1). In one embodiment, the cancer is metastatic cancer, such as, for example, breast cancer, ovarian cancer, melanoma, colorectal cancer, kidney cancer, cervical cancer, testicular cancer, or liver cancer. In one embodiment, the compound of Formula (1) inhibits actin.

According to another aspect of the invention there is provided a pharmaceutical composition for the treatment and/or mitigation of cancer, comprising an effective amount of a compound of Formula (1). In one embodiment, the pharmaceutical composition includes a compound of Formula (1) such as compound 4a, 4b, 4c, 4d, 4e, 4f, 4g, 4h, 11, 12, MA-02-058, MA-02-047, MA-02-044, or MA-02-046 as shown in Table 1, or a pharmaceutically acceptable salt thereof. In one embodiment, the pharmaceutical composition of the above embodiments or aspects, further comprising a pharmaceutically acceptable vehicle. In one embodiment, the pharmaceutical composition is for the treatment and/or mitigation of cancer. In one embodiment, the cancer is metastatic cancer. In one embodiment, the cancer is breast, ovarian, lung, or pancreatic cancer.

According to another aspect of the invention there is provided a pharmaceutical composition for suppressing metastatic cancer cell motility and survival, comprising a pharmaceutical composition as defined in any one of above embodiments or aspects, and a pharmaceutically acceptable vehicle. In one embodiment, the metastatic cancer is breast cancer, ovarian cancer, lung cancer, pancreatic cancer, melanoma, colorectal cancer, kidney cancer, cervical cancer, testicular cancer, or liver cancer. In one embodiment, the pharmaceutical composition further comprising one or more antineoplastic agent(s). In one embodiment, the pharmaceutical composition further comprises a protein or a glycosaminoglycan. In one embodiment, the protein is an antibody, hemoglobin, alphafeto-protein, fibrinogen, or serum albumin. In one embodiment, the glycosaminoglycan comprises hyaluronic acid.

According to another aspect of the invention there is provided a method of treating and/or mitigating cancer, a cell proliferation disorder, or an actin-related disorder, comprising administering to a subject a pharmaceutical composition comprising a compound of Formula (1). In one embodiment, the the cancer is metastatic cancer. In one embodiment, the metastatic cancer is breast cancer, ovarian cancer, lung cancer, pancreatic cancer, melanoma, colorectal cancer, kidney cancer, cervical cancer, testicular cancer, or liver cancer. In one embodiment, the compound of Formula (1) inhibits actin. In one embodiment, the compound of Formula (1) is compound 4a, 4b, 4c, 4d, 4e, 4f, 4g, 4h, 11, 12MA-02-058, MA-02-047, MA-02-044, or MA-02-046 of Table 1.

According to another aspect of the invention there is provided a method of inhibiting actin in a subject in need thereof, comprising administering to the subject the compound of Formula (1). In one embodiment of this aspect, the subject has inflammatory lung disease. In one embodiment of this aspect, sputum viscosity is reduced. In one embodiment, the actin-related disorder comprises accumulation of actin in cell nuclei. In one embodiment, the actin-related disorder comprises malaria.

According to another aspect of the invention there is provided a method of reducing actin released into circulation upon cellular damage, comprising administering the pharmaceutical composition to a subject in need thereof. In one embodiment of this aspect, the the cellular damage was caused by stroke, or an adverse cardiovascular problem.

According to another aspect of the invention there is provided a method of suppressing tumor growth, metastasis, or both, comprising administering a pharmaceutical composition as defined in any of the above embodiments or aspects, to a subject in need thereof.

According to another aspect of the invention there is provided a method of treating an actin-related disorder, comprising administering a pharmaceutical composition as defined in any of the above embodiments, to a subject in need thereof. In one embodiment, the the actin-related disorder comprises sputum viscosity in a subject with inflammatory lung disease. In one embodiment, the actin-related disorder comprises accumulation of actin in cell nuclei. In one embodiment, the actin-related disorder comprises malaria.

According to another aspect of the invention there is provided a method of reducing actin released into circulation upon cellular damage, comprising administering a pharmaceutical composition as defined in any one of the above embodiments to a subject in need thereof. In one embodiment, the cellular damage was caused by stroke, or an adverse cardiovascular problem.

According to another aspect of the invention there is provided use of a compound of Formula (1) for preparation of a medicament for treating and/or mitigating one or more of cancer, actin-related disorder, malaria, inflammatory lung disease, stroke, or an adverse cardiovascular problem.

BRIEF DESCRIPTION OF THE DRAWINGS

For a better understanding of the present invention and to illustrate more clearly how it may be carried into effect, reference will now be made by way of example to the accompanying drawings, which illustrate aspects and features according to preferred embodiments of the present invention, and in which:

FIG. 3A shows effects of MycB treatments on SKOV3 tumor xenograft model as a monotherapy or in combination with Trastuzumab (TZ). The graph shows subcutaneous SKOV3 tumor volumes versus days post injection of SKOV3 cells in $Rag2^{-/-}$:$IL2R\gamma c^{-/-}$ mice. Following the detection of palpable tumors, mice were randomized between vehicle control (DMSO), MycB (100 ng, intratumoral), TZ (50 µg, intraperitoneal), or the combination of MycB and TZ (same doses/delivery), and given twice weekly until endpoint was reached (n=6/group; significant differences between treatment groups based on ANOVA are indicated by *$P<0.05$, ****$P<0.0001$).

FIG. 3B shows the differences in tumor mass between treatment groups for the same study as FIG. 3A (significant differences between treatment groups based on ANOVA are indicated by *$P<0.05$, **$P<0.01$).

FIGS. 4A-C shows in vitro structure-activity relationship (SAR) studies of simplified actin-targeting natural product analogs in comparison to the bioactive natural product MycB, wherein:

FIG. 4A shows a plot to illustrate concentration-dependent effects of MycB on actin polymerization, wherein a change in fluorescence signal during polymerization of 9.0 µM pyrenyl-G-actin was measured in the presence of 0 to 5 µM MycB, and plotted as a function of time;

FIG. 4B shows effect of analogs 4a and 4b (diastereomers at C30 position) on actin polymerization;

FIG. 4C shows concentration-dependent effects of MycB and selected toxin analogs on actin polymerization relative to 9.0 µM pyrenyl-G-actin alone (polymerization rates were determined by measuring the slope of polymerization plots like those depicted in FIG. 4A).

FIGS. 5B and 5C shows percent wound confluence and percent wound density for cells treated with the indicated concentrations of MycB in migration assays (5B) or invasion through Matrigel (5C; significant differences between treatment groups based on ANOVA are indicated by *$P<0.05$, ***$P<0.01$).

FIG. 6A shows effects of MycB and analogs on the kinetics and extent of SKOV3 cell migration into a wound area. The graph shows wound confluence versus time (h) for SKOV3 cells treated with DMSO, MycB, or the indicated analogs up to 24 hours (h; see Table 1 for structures for indicated compounds).

FIG. 6B shows effects of MycB and analogs on the kinetics and extent of SKOV3 cell invasion into a wound area covered with 5% Matrigel. The graph shows percent wound density versus time (h; see Table 1 for structures for indicated compounds).

FIG. 6C shows an endpoint comparison of wound confluence for SKOV3 migration described in FIG. 6A (see Table 1 for structures for indicated compounds).

FIG. 6D shows an endpoint comparison of percent wound density for SKOV3 invasion described in FIG. 6B (see Table 1 for structures for indicated compounds).

FIG. 7A shows the effects of MycB and analogs on a 3D model of cancer cell migration, wherein cells grown as spheroids are allowed to attach and migrate outwards for up to 72 hours. The graph shows the percent migration relative to DMSO control (at 24 h) for treatments with MycB or the specified test compounds for 24, 48 and 72 h using SKOV3 cells (see Table 1 for structures for indicated compounds).

FIG. 7B shows an endpoint analysis of relative cell migration for treatment groups described in FIG. 7A (significant differences between treatment groups based on ANOVA are indicated by *$P<0.05$, ****$P<0.0001$; see Table 1 for structures for indicated compounds).

FIG. 7C shows a dose response analysis of test compound 2453 on percent SKOV3 cell migration in the spheroid reattachment assay for 24, 48 and 72 h.

FIG. 7D shows a dose response analysis of test compound 2534 on percent SKOV3 cell migration in the spheroid reattachment assay for 24, 48 and 72 h.

FIG. 8A shows a plot of percent SKOV3 cell viability versus dose of the indicated analogs based on propidium iodide (PI) uptake at 48 h (see Table 1 for structures for indicated compounds).

FIG. 8B shows a plot of percent HCC1954 cell viability versus dose of the indicated analogs based on PI uptake at 48 h (see Table 1 for structures for indicated compounds).

FIG. 8C shows a comparison of cell confluence versus treatments with DMSO (1%), MycB (25 nM), analogs (25 µM, see Table 1 for structures for indicated compounds), or HER2 inhibitor Lapatinib (25 µM) at 48 h.

FIG. 8D shows a comparison of cell confluence versus treatments with DMSO (1%), MycB (25 nM), analogs (25 µM, see Table 1 for structures for indicated compounds), or HER2 inhibitor Lapatinib (25 µM) at 48 h.

FIG. 8E shows a comparison of test compound 2534 (25 µM) and Lapatinib (30 µM) on SKOV3 cytotoxicity using PI uptake assay (cells/image) versus time up to 48 h (see Table 1 for structure of indicated compound).

FIG. 8F shows a comparison of test compound 2534 (25 µM) and Lapatinib (25 µM) on HCC1954 cytotoxicity using PI uptake assay (cells/image) versus time up to 48 h (see Table 1 for structure of indicated compound).

FIG. 9A shows growth suppression of HER2 cancer cells by select Myc B analogs and specifically shows a plot of cell confluence change (percentage) for indicated analogs, which indicate rate of growth of HER2 cancer cells HCC1954 (breast) as measured using a live cell imaging systemas compared to DMSO control conditions and as compared to treatment with nanomolar doses of Myc B.

FIG. 9B shows growth suppression of HER2 cancer cells by select Myc B analogs and specifically shows a plot of cell confluence change (percentage) for indicated analogs, which indicate rate of growth of SKOV3 (ovarian) as measured using a live cell imaging systemas compared to DMSO control conditions and as compared to treatment with nanomolar doses of Myc B.

DETAILED DESCRIPTION OF EMBODIMENTS

Definitions

Figure 1:
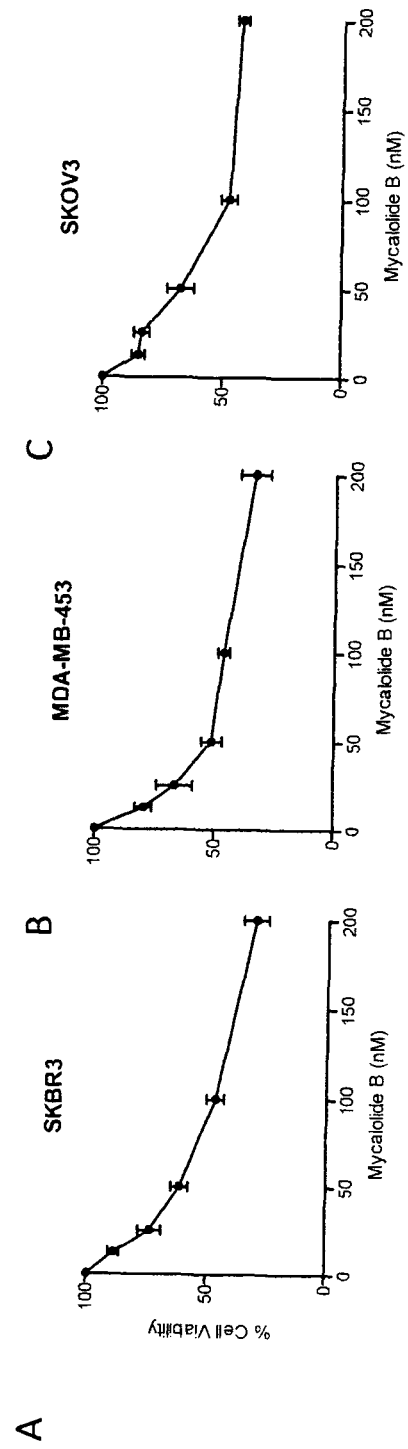
FIG. 1A-C show plots showing loss of viability of HER2+ breast and ovarian cancer cells with increasing doses of Mycalolide B (MycB). Specifically, graphs indicate percentage of viable cells after 48 hours of treatment with mycalolide B at 0-200 nM concentrations using SKBR3, MDA-MB-453 and SKOV3 cells. Cell viability was determined using Trypan blue exclusion assay (both unstained and stained cells were counted using a hemocytometer; values are mean±standard error of the mean (SEM) for triplicate experiments).

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term "ADC" refers to antibody-drug conjugates.

As used herein, the term "ECM" refers to extracellular matrix.

As used herein, the term "PI" refers to propidium iodide.

As used herein "unsubstituted" refers to any open valence of an atom being occupied by hydrogen.

As used herein "substituted" refers to the structure having one or more substituents.

As used herein "heteroatom" means a non-carbon, non-hydrogen atom, and may be used to denote atoms that have a lone pair of electrons available to form dative or coordinate bonds (e.g., N, O, P).

As used herein the term "TBSO" refers to a tertbutyldimethylsilyloxy moiety.

As used herein the term "alkoxy" or "alkoxy group" refers to an —O—R moiety, where R is an aliphatic or aryl moiety that may be substituted or unsubstituted.

As used herein the term "acyloxy" or "acyloxy group" refers to a —O—C(=O)—R moiety, where R is an aliphatic or aryl moiety that may be substituted or unsubstituted.

As used herein the term "acyl" or "acyl group" refers to a —C(=O)—R moiety, where R is an aliphatic and aryl moiety that may be substituted or unsubstituted.

As used herein the term "ester" refers to a —C(=O)—O—R or a —C(=O)—S—R moiety, where R is an aliphatic or aryl moiety that may be substituted or unsubstituted.

As used herein the term "amide" refers to a —C(=O)—NR$^1$R$^2$ moiety where R$^1$ and R$^2$ are independently hydrogen atoms or aliphatic or aryl moieties.

As used herein the term "carbamate" refers to a —O—C(=O)—NR$^a$R$^b$ moiety where R$^a$ and R$^b$ are independently hydrogen atoms or aliphatic or aryl moieties.

As used herein the term "leaving group" refers to a moiety of a reactant that is displaced by another moiety during a reaction. Common leaving groups include, for example, chloride, bromide, iodide, mesylate, tosylate, and triflate.

As used herein, the term "substituted" means having one or more substituent moieties whose presence either facilitates or improves the desired reaction, or does not impede the desired reaction. A "substituent" is an atom or group of bonded atoms that can be considered to have replaced one or more hydrogen atoms attached to a parent molecular entity; and, whose presence either facilitates or improves desired reactions and/or functions of the invention, or does not impede desired reactions and/or functions of the invention. Examples of substituents include alkyl, alkenyl, alkynyl, aryl, polycyclic aryl, benzyl, polycyclic benzyl, fused aromatic rings, aryl-halide, heteroaryl, cycloalkyl (non-aromatic ring), Si(alkyl)$_3$, Si(alkoxy)$_3$, halo, alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkyithiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, aryl, aryl-halide, heteroaryl, and cycloalkyl (i.e., non-aromatic ring).

As used herein, "aliphatic" refers to hydrocarbon moieties that are linear, branched or cyclic, may be alkyl, alkenyl or alkynyl, and may be substituted or unsubstituted. "Alkenyl" means a hydrocarbon moiety that is linear, branched or cyclic and contains at least one carbon to carbon double bond. "Alkynyl" means a hydrocarbon moiety that is linear, branched or cyclic and contains at least one carbon to carbon triple bond.

As used herein, "alkyl" or "alkylene" refers to a linear, branched or cyclic, saturated hydrocarbon, which consists solely of single bonded carbon and hydrogen atoms, which can be unsubstituted or is optionally substituted with one or more substituents, for example a methyl or ethyl group. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups.

The term "cycloalkyl" as used herein refers to a non-aromatic, saturated or partially saturated, monocyclic, bicyclic or tricyclic hydrocarbon ring system containing at least three carbon atoms. Examples of C3-Cn cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "alkenyl" or "alkenylene" means a hydrocarbon moiety that is linear, branched or cyclic and comprises at least one carbon to carbon double bond which can be unsubstituted or optionally substituted with one or more substituents. "Alkynyl" or "alkynylene" means a hydrocarbon moiety that is linear, branched or cyclic and comprises at least one carbon to carbon triple bond which can be unsubstituted or optionally substituted with one or more substituents.

As used herein, "aryl" and/or "aromatic ring" refers to hydrocarbons derived from benzene or a benzene derivative that are unsaturated aromatic carbocyclic groups from 6 to 100 carbon atoms, or from which may or may not be a fused ring system, in some embodiments 6 to 50, in other embodiments 6 to 25, and in still other embodiments 6 to 15. The aryls may have a single or multiple rings. The term "aryl" and/or "aromatic ring" as used herein also includes substituted aryls and/or aromatic rings that include aromatic heterocycles. Examples include, but are not limited to, phenyl, naphthyl, xylene, phenylethane, substituted phenyl, substituted naphthyl, substituted xylene, substituted 4-ethylphenyl and the like.

As used herein, the term "unsubstituted" refers to any open valence of an atom being occupied by hydrogen. Also, if an occupant of an open valence position on an atom is not specified then it is hydrogen.

As used herein the term "hydroxyl protecting groups" includes many moieties that are used to block an oxygen moiety from reaction until the protecting group is cleaved and the oxygen is once again available for reaction (Wuts, P. G. M. and Greene, T. W. (2007) "Protective Groups in Organic Synthesis" John Wiley & Sons).

As used herein "TBS" refers to tert-butyldimethylsilyl.

As used herein "Bn" refers to benzyl.

As used herein "BINOL" refers to 1,1'-bi(2-naphthol).

As used herein "DBU" refers to 1,8-diazabicyclo[5.4.0]undec-7-ene.

As used herein "DCE" refers to 1,2-dichloroethane.

As used herein "DDQ" refers to 2,3-dichloro-5,6-dicyano-p-benzoquinone.

As used herein "DIBAL" refers to diisobutylaluminum hydride.

As used herein "DMAP" refers to dimethylaminopyridine.

As used herein "THF" refers to tetrahydrofuran.

Embodiments

Actin is found in essentially all eukaryotic cells and is a family of globular multi-functional proteins that form microfilaments. Actin participates in many important cellular processes, including muscle contraction, cell motility, cell division, cytokinesis, vesicle and organelle movement, cell signaling, and the establishment and maintenance of cell junctions and cell shape. Many of these processes are mediated by extensive and intimate interactions between actin and cellular membranes. In vertebrates, three main groups of actin isoforms, alpha, beta, and gamma, have been identified. The alpha actins, which are found in muscle tissues, enable muscle contractility. The beta and gamma actins coexist in most cell types as cytoskeleton components, and as mediators of internal cell motility.

Several natural products that display potent cytotoxic activities toward cancer cells target actin. Some of these agents are unsuitable for clinical use due to their lack of specificity for the actin of tumor cells. This lack of specificity leads to severe side effects which are ascribed to binding at the actin in muscle sarcomere. The lack of specificity also leads to poor efficacy in regard to tumor cell deaths.

Derivatives of natural products that include a cytotoxic pharmacophore of a parent molecule are useful, and are generally easier to prepare than the natural form. For example, such derivatives can be combined with ancillary moieties such as monoclonal antibodies, carrier peptides, or polymeric linkers to form conjugates. Such conjugates offer dual activity: cytotoxicity and specificity for tumor cells. Their specificity increases tolerability and clinical benefit. Conjugates of actin-targeting poisons may enable delivery of cytotoxic derivatives to primary tumors and metastatic cells, and limit harmful effects on healthy cells. Antibody-Drug Conjugates (ADCs) are one type of conjugate that could be used to target cancer by attaching an actin-targeting moiety to a cancer-seeking antibody. Such ADCs would in principle maximize the cancer killing potential of a therapeutic by allowing the actin-inhibiting component to be taken up by a cancer cell with precision, before the cell has a chance to form secondary tumors. In doing so, these agents have the potential to reduce many of the common side-effects associated with cancer chemotherapies, and to diminish cancer burden and mortality.

Actin-targeting natural products possess a diverse range of actin-disrupting activities that halt cell division and migration. Such activities lead to cell death in cultured tumor strains that are highly metastatic and express targetable antigens. Toxin addition causes rapid changes in F-actin organization, leading to altered cell shape compared to highly motile phenotypes observed in vehicle control cells. A disruption of invadopodia occurs. Invadopodia are F-actin-based membrane protrusions that degrade extracellular matrix (ECM) to enhance tissue invasion and tumor metastasis. Treatment with actin toxins at nanomolar doses led to severe defects in migration and invasion properties of metastatic cancers (e.g., breast cancers, lung cancers, melanomas, ovarian cancer, colorectal cancer, kidney cancer, cervical cancer, testicular cancer, and liver cancer.). Through conjugation of these toxins to tumor-specific antibodies, ADCs are potent inhibitors of tumor progression and metastasis.

A compound of general formula (1) is provided herein, wherein the structure is a derivative of Mycalolide:

Formula (1)

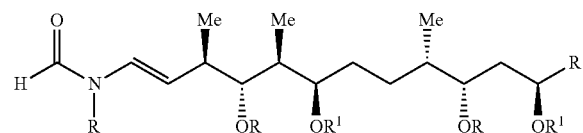

wherein $R^1$ is independently H, —C(=O)R, —C(OR)(R)(R), —C(=O)NR$^2$R$^3$, —S(O$_2$)NR, —P(=O)(OR)$_2$, aliphatic and/or aryl moiety; and R, $R^2$, and $R^3$ are independently an aliphatic moiety and/or aryl moiety that can be substituted or unsubstituted and can include one or more heteroatoms such as P, S, N, or O.

Structural formulae of representative examples of compounds of Formula(1) are provided in Table 1.

As described above, the actin cytoskeleton is a key cellular component in enablement of morphological changes in cancer cells since it facilitates their ability to metastasize. Chemotherapeutic agents are described herein that limit actin's contribution to the spread of cancer. Potent natural inhibitors of actin, such as the mycalolides, inspired the design and preparation of rationally-simplified versions of the naturally occurring agents. Actin-inhibiting ability of these derivatives has been demonstrated in several ways thus validating them as anti-cancer agents.

Chemotherapy agents often fail to block the main cause of cancer-associated deaths, namely cancer cell migration events leading to metastasis. By targeting actin, key cellular machinery responsible for morphological changes in malignant cells is affected and migration of malignant cells from primary tumor sites to other organs is inhibited.

Cancer metastasis begins when a subset of cancer cells actively migrate toward, and penetrate into, blood vessels and lymph nodes to disseminate throughout the body. Embolism of these tumor cells in microcapillary networks can be followed by invasion into the capillary walls (extravasation), allowing entry into surrounding tissue to establish secondary tumor sites that can lead to metastatic disease. Growth hormones, signaling cascades and proteolytic enzymes all contribute to this process, but the main driver of cancer cell migration is actin.

A diverse group of natural products that specifically target and demonstrate cytotoxic activity against the actin cytoskeleton have been isolated from a variety of sources: terrestrial plants, sponges, marine nudibranchs, algae, fungi, and bacteria.

A class of natural product poisons of the actin cytoskeleton have inspired a family of anticancer agents. By conjugating these agents to cancer seeking antibodies, ADCs may deliver actin poisons to tumor cells, thereby providing a new strategy to address cancer and patient prognosis.

As described above, derivatives of natural products that include a cytotoxic pharmacophore of a parent molecule are useful, and are generally easier to prepare than the natural form. Such derivatives can also be combined with ancillary moieties such as proteins, including monoclonal antibodies, carrier peptides, or polymeric linkers to form conjugates to enhance their effects. Such conjugates offer dual activity: increased cytotoxicity and specificity for tumour cells. Their specificity increases tolerability and clinical benefit. Conjugates of actin-targeting poisons may enable delivery of cytotoxic derivatives to primary tumours and metastatic cells, and limit harmful effects on healthy cells. ADCs are one type of conjugate that could be used to target cancer by attaching an actin-targeting moiety to a cancer-seeking antibody. Such ADCs would in principle maximize the cancer killing potential of a therapeutic by allowing the actin-inhibiting component to be taken up by a cancer cell with precision, before the cell has a chance to form secondary tumours. In doing so, these agents have the potential to reduce many of the common side-effects associated with cancer chemotherapies, and to diminish cancer burden and mortality. However, ADCs do have development challenges from their complex and heterogeneous nature including poor solubility, instability, aggregation, and, due to their size, can have poor penetration to tumours. To that end other non-antibody proteins could also have utility as conjugates. Such examples include using hemoglobin, alphafeto-protein, fibrinogen or serum albumin. Other possible ancillary moieties for drug conjugation include glycosaminoglycans such a hyaluronic acid.

Referring to FIG. 1A-C, the cytotoxicity of MycB on HER2+ breast and ovarian cancer cells was measured. Specifically, data is provided regarding the percentage of viable cells following treatment with MycB at 0-200 nM concentrations for 48 hours using SKBR3, MDA-MB-453 and SKOV3 cells. Cell viability was determined using Trypan blue exclusion assay (both unstained and stained cells were counted on a hemocytometer; values are mean±SEM of triplicate experiments).

Figure 2:
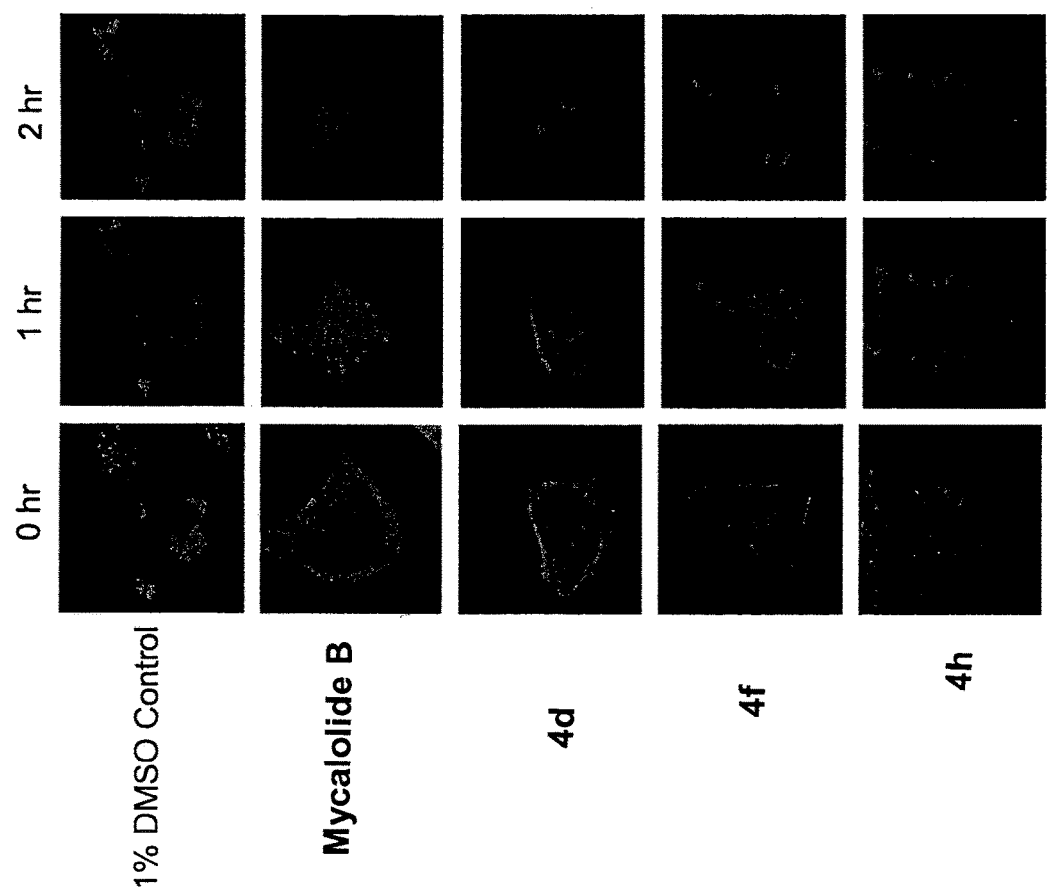
FIG. 2 shows images acquired by live cell imaging of SKOV3 cells expressing LifeAct-GFP (to visualize F-actin) following treatment with DMSO (1%), MycB (25 nM) or the indicated analogs (10 µM) for 0-2 hours (hr). Images were acquired using a Quorum Wave FX-X1 Spinning Disc Confocal live cell imaging system.

Referring to FIG. 2, images are shown that depict effects of MycB and analogs on actin cytoskeleton in live cancer cells. Specifically, SKOV3 cells expressing LifeAct-GFP (to visualize F-actin) were incubated with either 1% DMSO (as a vehicle control), 25 nM MycB, or 10 μM of the indicated analogs, and imaged immediately and continuously by confocal microscopy. Images were taken at time 0, 1 and 2 h in the stabilized conditions of the Quorum Wave FX-X1 Spinning Disc Confocal live cell imaging system.

Referring to FIGS. 3A and 3B, a proof-of-principle study of the anticancer effects of MycB in a SKOV3 tumor xenograft model. FIG. 3A shows the effects of MycB on growth of subcutaneous SKOV3 tumors versus time (days post injection of SKOV3 cells) in Rag2$^{-/-}$:IL2Rγc$^{-/-}$ mice. Following the detection of palpable tumors, mice were randomized between vehicle control (DMSO), MycB (100 ng, intratumoral), TZ (50 μg, intraperitoneal), or both MycB and TZ (same doses/delivery) twice weekly until endpoint was reached (n=6/group; significant differences between treatment groups based on ANOVA are indicated by *P<0.05, **** P<0.0001). FIG. 3B shows the differences in tumor mass between treatment groups for the same study as FIG. 3A (significant differences between treatment groups based on ANOVA are indicated by *P<0.05, **P<0.01).

Referring to FIGS. 4A-C, in vitro SAR studies were conducted for simplified actin-targeting natural product analogs, wherein FIG. 4A shows a plot to illustrate concentration-dependent effects of mycalolide B on actin polymerization, wherein a change in fluorescence signal during polymerization of 9.0 µM pyrenyl-G-actin was measured in the presence of 0 to 5 µM MycB, and plotted as a function of time. FIG. 4B shows an effect of analogs 4a and 4b (diastereomers at C30 position) on actin polymerization. FIG. 4C shows concentration-dependent effects of MycB and selected toxin analogs on actin polymerization relative to 9.0 µM pyrenyl-G-actin alone. Polymerization rates were determined by measuring the slope of polymerization plots like those depicted in FIG. 4A.

Figure 5A:
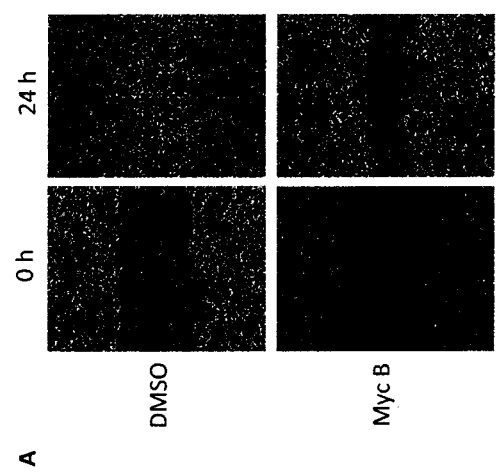
FIG. 5A shows phase contrast images of wound closure cell migration assays using SKOV3 cells treated with DMSO (1%) or MycB (25 nM) at time 0 and 24 h.
Figure 5D:
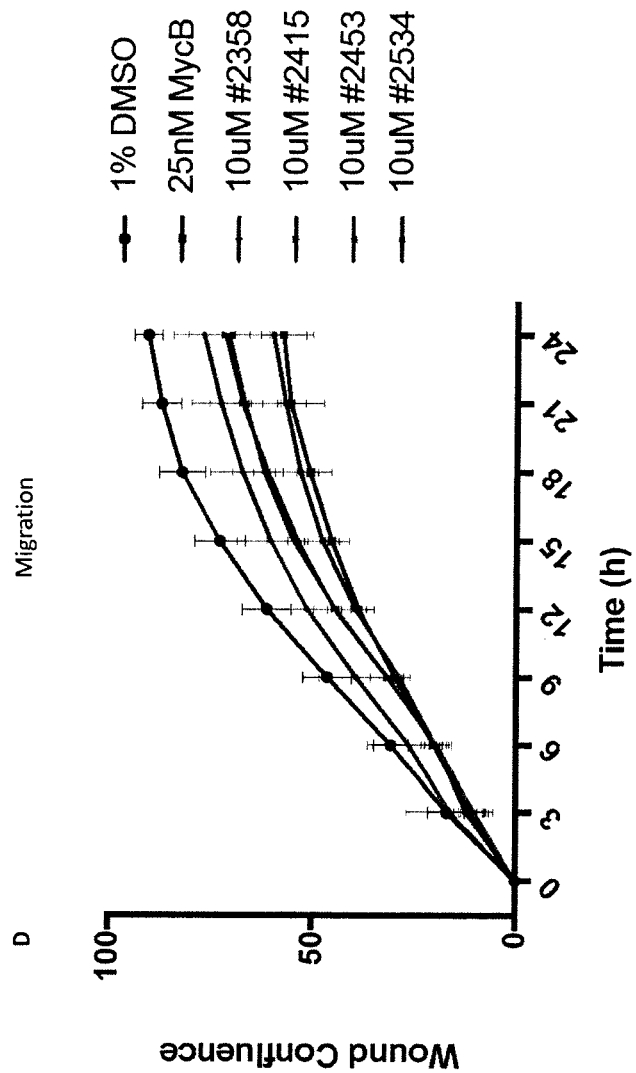
FIG. 5D shows a plot of wound confluence versus time for SKOV3 cells treated with DMSO, MycB (25 nM), or the indicated analogs (10 uM) for 0-24 h (see Table 1 for structures for indicated compounds).

Referring to FIG. 5A-D, the effects of MycB and analogs were tested for their ability to suppress wound healing migration or invasion of SKOV3 cells using an IncuCyte ZOOM system. SKOV3 cells (25,000) were seeded in triplicates in a 96-well ImageLock plates and confluent monolayers were subjected to wound healing migration or invasion (wound area overlayed with 5% Matrigel). Representative phase contrast images are shown for time 0 and after 24 h for DMSO and MycB (25 nM). FIGS. 5B and 5C show the percent wound confluence (migration) and percent wound density (invasion) for SKOV3 cells treated with the indicated concentrations of MycB as measured using the IncuCyte Software. FIG. 5D shows a plot of percent wound closure for SKOV3 cell migration assays treated with DMSO, MycB (25 nM), or the indicated analogs (10 µM) as measured using the IncuCyte Software.

Referring to FIGS. 6A-D, plots are shown for SKOV3 scratch wound migration assays (24 h) and invasion assays (48 h) using the IncuCyte ZOOM system (n=3).

Referring to FIGS. 7A-D, SKOV3 cells were grown in polyhema-coated wells to form spheroids for 3 days prior to transfer to adherent conditions that facilitate cell migration from the spheroids. FIG. 7A shows a plot of percent migration relative to DMSO control for the indicated treatments with MycB or analogs for 24, 48 and 72 h. FIG. 7B summarizes the relative cell migration area at 72 h for each treatment group in triplicate. FIG. 7C-D show dose response studies of analogs 2453 (C) and 2534 (D) in the spheroid reattachment migration assay at 24, 48 and 72 h.

Referring to FIG. 8A, a plot is shown that presents percent SKOV3 cell viability versus 48 h treatment for a propidium iodide (PI) uptake cytotoxicity study (n=2).

Referring to FIG. 8B, a plot is shown of percent HCC1954 cell viability versus 48 h treatment for a PI cytotoxicity study (n=2).

Referring to FIG. 8C, a plot is shown of percent SKOV3 cell confluence versus 48 h treatment for a PI cytotoxicity study (n=2).

Referring to FIG. 8D, a plot is shown of HCC1954 cell confluence versus treatment for a PI cytotoxicity study (n=2).

Referring to FIG. 8E, a plot is shown of a PI+ (cells/image) versus time for a PI cytotoxicity study (n=2) of SKOV3 cells.

Referring to FIG. 8F, a plot is shown of HCC1954 cell viability (cells/field) versus treatment for a PI cytotoxicity study (n=2).

Referring to FIG. 9A, a plot is shown to depict growth suppression of HER2 cancer cells by select Myc B analogs and specifically shows a plot of cell confluence change for indicated analogs, which indicate rate of growth of HER2 cancer cells HCC1954 (breast) as measured using a live cell imaging systemas compared to DMSO control conditions and as compared to treatment with nanomolar doses of Myc B.

Referring to FIG. 9B, a plot is shown of growth suppression of HER2 cancer cells by select Myc B analogs and specifically shows a plot of cell confluence change for indicated analogs, which indicate rate of growth of SKOV3 (ovarian) as measured using a live cell imaging systemas compared to DMSO control conditions and as compared to treatment with nanomolar doses of Myc B.

Figure 10:
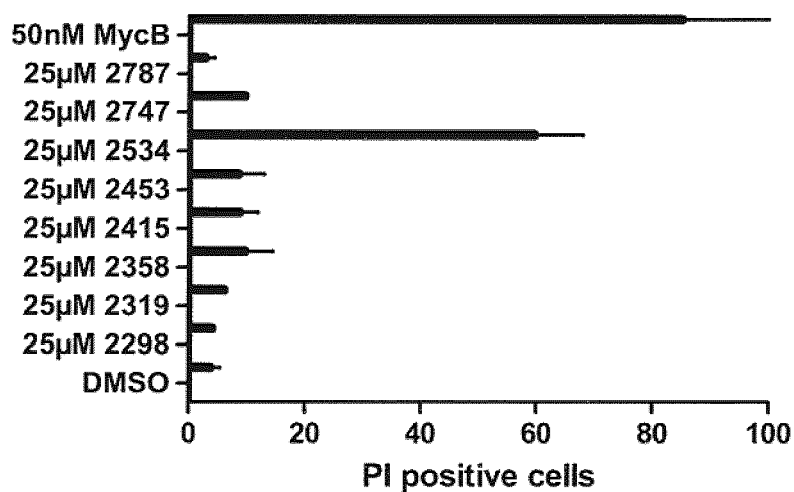
FIG. 10 shows cytotoxicity effects of Myc B and analogs in SKOV3 cells and specifically shows the number of PI positive cells (mean±SEM) at 48 hours of treatment when SKOV3 (ovarian) cells were incubated with DMSO (1%) or analog in DMEM supplemented with 2% FBS and PI (1 µM) using an IncuCyte Zoom Live Cell Analysis System for 48 hours.

Referring to FIG. 10, a plot is shown that depicts cytotoxicity effects of Myc B and analogs in SKOV3 cells and specifically shows the number of PI positive cells (mean±SEM) at 48 hours of treatment when SKOV3 (ovarian) cells were incubated with DMSO (1%) or analog in DMEM supplemented with 2% FBS and PI (1 µM) using an IncuCyte Zoom Live Cell Analysis System for 48 hours. Compared to DMSO control, which showed limited cytotoxicity measured by propidium iodide (PI) uptake in the cells, Myc B treatment caused a significant increase in PI uptake (cytoxicity) in SKOV3 cells. An analog that showed a significant cytoxicity response was 4f (also referred to herein as 2534).

Figure 11:
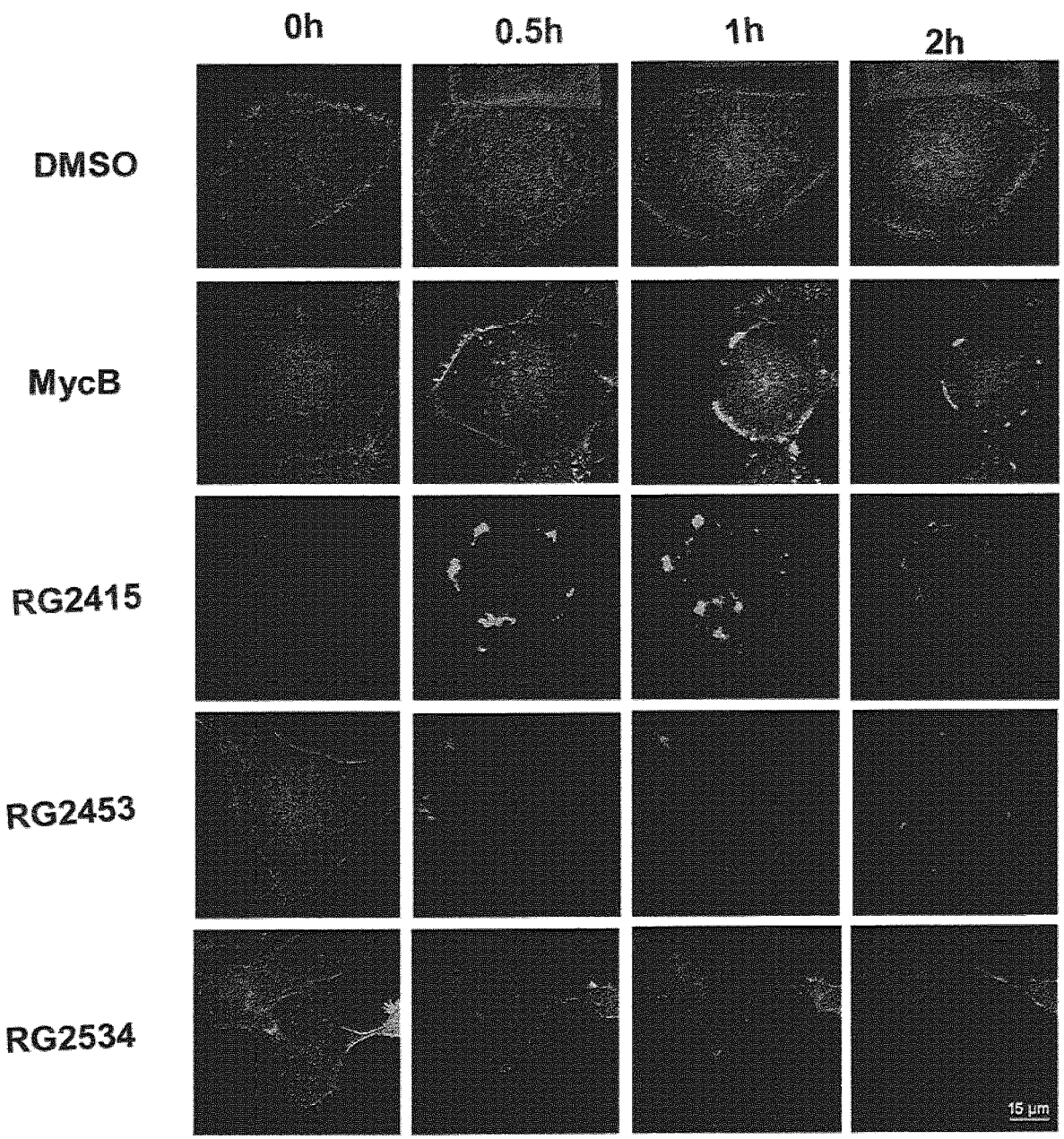
FIG. 11 shows representative confocal micrographs for selected time points (0-2 hours) of live cell imaging for SKOV3 cells expressing LifeAct-GFP (lighter regions) treated with either DMSO (1%), Myc B (25 nM), or indicated analogs (10 µM; scale bar indicates 15 µm).

Referring to FIG. 11, representative confocal micrographs are shown for selected time points (0-2 hours) of live cell imaging for SKOV3 cells expressing LifeAct-GFP (lighter regions) treated with either DMSO (1%), Myc B (25 nM), or indicated analogs (10 µM; scale bar indicates 15 µm), the disruption of filamentous actin (F-actin) in HER2 cancer cells was measured using live cell confocal imaging of LifeAct-GFP reporter. The LifeAct-GFP signal in DMSO control conditions indicates the localization of F-actin structures in SKOV3 cells. Treatment with Myc B (25 nM) shows a time-dependent collapse of F-actin into large aggregates near the cell periphery. Treatments with analogs 4h (2415) and 4g (2453) at 10 µM dose resulted in similar collapse of F-actin structures. Analog 2534 had limited effects at early time points shown in this figure.

Figure 12:
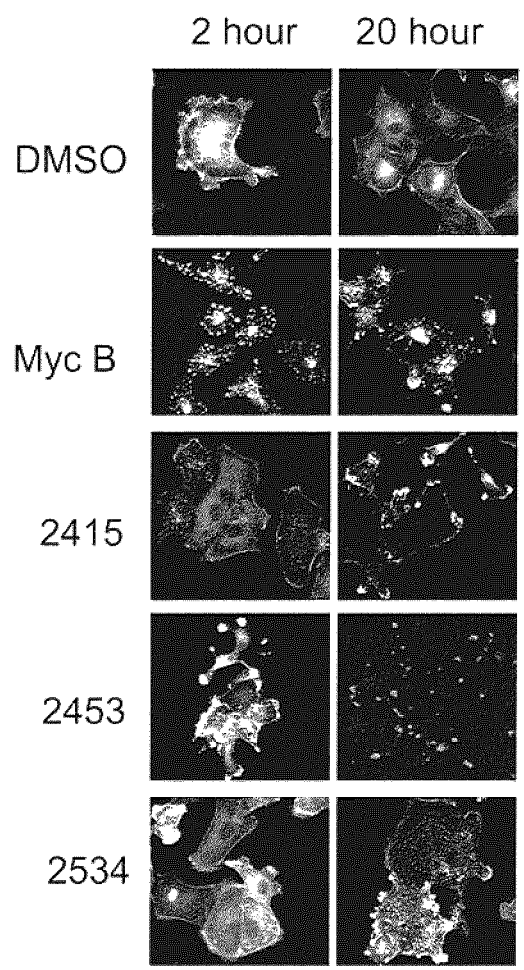
FIG. 12 shows representative fluorescence micrographs of SKOV3 cells treated with DMSO (1%), Myc B (25 nM), or indicated analog (10 µM) for 2 or 20 hours prior to staining of F-actin (TRITC-Phalloidin).

Referring to FIG. 12, representative fluorescence micrographs are shown of SKOV3 cells treated with DMSO (1%), Myc B (25 nM), or indicated analog (10 µM) for 2 or 20 hours prior to staining of F-actin (TRITC-Phalloidin). the effects of Myc B analog treatments over 20 hours are compared with DMSO and Myc B in HER2 cancer cells. The localization of endogenous F-actin was revealed by staining with TRITC-Phalloidin and epifluorescence micrograph images are shown. The motile shape and uniform distrubution of F-actin at the cell periphery of SKOV3 cells were observed in the DMSO control images. To summarize these findings, treatments with Myc B (25 nM) or the indicated analogs (10 µM) led to disruption of F-actin at the cell periphery and collapse into large aggregates in the cytoplasm of the cells. Of the analogs tested, 4h (2415) and 4g (2453) were the most highly disruptive of F-actin in these assays. As described in Example 37, disruption of filamentous actin (F-actin) in HER2 cancer cells was measured using live cell confocal imaging of LifeAct-GFP reporter. The LifeAct-GFP signal in DMSO control conditions indicates the localization of F-actin structures in SKOV3 cells. Treatment with Myc B (25 nM) shows a time-dependent collapse of F-actin into large aggregates near the cell periphery. Treatments with analogs 4h (2415) and 4g (2453) at 10 µM dose resulted in similar collapse of F-actin structures. Analog 4f (2534) had limited effects at early time points. Compounds described herein can be used to treat such actin-related problems because of their efficacy in disrupting actin, as shown by studies described in the Examples and Figures herein.

Conditions that include actin-related problems include inflammatory lung disease (e.g., sputum viscosity may be decreased by treatment with a compound of Formula (1). Other actin-related disorders are characterized by accumulation of actin in cell nuclei. An example of such a condition is malaria. Compounds of Formula(1) are suitable for use in a method of reducing actin that has been released into a subject's circulatory system upon cellular damage. Such cellular damage may be caused by stroke, or an adverse cardiovascular problem.

Accordingly, due to their efficacy in disrupting actin, compound of Formula (1) are suitable, either alone or in combination, for preparation of a medicament for treating and/or mitigating one or more of cancer, actin-related disorder, malaria, inflammatory lung disease, stroke, or an adverse cardiovascular problem.

In some embodiments of combination therapy, a first compound is of Formula (1). In other embodiments, the second compound is an antineoplastic agent that is not of Formula (1). Known antineoplastic agents that may be suitable in a combination therapy according to the invention include, but are not limited to anthracyclines (e.g., doxorubicin, daunorubicin), other antibiotic agents (e.g, the HSP90 inhibitor 17-AAG), Vinca alkaloids (e.g., vinblastine, vincristine), epipodophyllotoxins (e.g., etoposide, teniposide), pyrimidine analogs (e.g., gemcitabine, 5-fluorouracil, cytarabine), taxanes (e.g., paclitaxel), platinum-based cancer drugs (e.g., cisplatin), monoclonal antibodies (e.g., TZ/Herceptin), and equivalents thereof.

Compounds of the invention can be formulated to ensure proper distribution in vivo. For example, therapeutic compounds of the invention can be formulated in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., Ranade, V. V. *J. Clin. Pharmacol.* (1989) 29(8):685-94). Exemplary targeting moieties include folate and biotin (see, e.g., U.S. Pat. No. 5,416,016 to Low et al.); mannosides (Umezawa et al., *Biochem. Biophys. Res. Commun.* (1988) 153(3):1038-44; antibodies (Bloeman et al., *FEBS Lett.* (1995) 357:140; Owais et al., *Antimicrob. Agents Chemother.* (1995) 39(1):180-4); and surfactant protein A receptor (Briscoe et al., *Am. J. Physiol.* (1995) 268(3 Pt 1): L374-80). Liposomal formulations of actin inhibitors may include a targeting moiety.

Delivery and in vivo distribution can also be affected by alteration of an anionic group of compounds of the invention. For example, anionic groups such as phosphonate or carboxylate can be esterified to provide compounds with desirable pharmacokinetic, pharmacodynamic, biodistributive, or other properties.

To administer a therapeutic compound by other than parenteral administration, it may be necessary to coat the compound with, or co-administer the compound with, a material to prevent its inactivation. For example, the therapeutic compound may be administered to a subject in an appropriate vehicle, for example, liposomes, or a diluent. Pharmaceutically acceptable diluents include saline and aqueous buffer solutions. Liposomes include water-in-oil-in-water CGF emulsions as well as conventional liposomes (Strejan et al., *Prog. Clin. Biol. Res.* (1984) 146: 429-34).

The therapeutic compound may also be administered ocularly, topically, intravaginally, as well as parenterally (e.g., intramuscularly, intravenously, intraperitoneally, intraspinally, intrathecally, or intracerebrally). Dispersions can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g. vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

Solid dosage forms for oral administration include ingestible capsules, tablets, pills, lollipops, powders, granules, elixirs, suspensions, syrups, wafers, buccal tablets, troches, and the like. In such solid dosage forms the active compound is mixed with at least one inert, pharmaceutically acceptable excipient or diluent or assimilable edible vehicle such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the therapeutic compound in the compositions and preparations may, of course, be varied. The amount of the therapeutic compound in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Therapeutic compounds can be administered in timerelease or depot form, to obtain sustained release of the therapeutic compounds over time. The therapeutic compounds of the invention can also be administered transdermally (e.g., by providing the therapeutic compound, with a suitable vehicle, in patch form).

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of neurological conditions in subjects.

Therapeutic compounds according to the invention are administered at a therapeutically effective dosage sufficient to achieve the desired therapeutic effect, e.g. to prevent the spread of cancer and/or kill cancerous cells. Actual dosage levels of active ingredients in the pharmaceutical compositions of this invention may be varied so as to obtain an amount of the active compound(s) that is effective to achieve and maintain the desired therapeutic response for a particular subject, composition, and mode of administration. The selected dosage level will depend upon the activity of the particular compound, the route of administration, frequency of administration, the severity of the condition being treated, the condition and prior medical history of the subject being treated, the age, sex, weight and genetic profile of the subject, and the ability of the therapeutic compound to produce the desired therapeutic effect in the subject. Dosage regimens can be adjusted to provide the optimum therapeutic response. For example, several divided doses may be administered daily or the dose may be proportionally reduced as indicated by the exigencies of the therapeutic situation.

However, it is well known within the medical art to determine the proper dose for a particular patient by the dose titration method. In this method, the patient is started with a dose of the drug compound at a level lower than that required to achieve the desired therapeutic effect. The dose is then gradually increased until the desired effect is achieved. Starting dosage levels for an already commercially available therapeutic agent of the classes discussed above can be derived from the information already available on the dosages employed. Also, dosages are routinely determined through preclinical ADME toxicology studies and subsequent clinical trials as required by the FDA or equivalent agency. The ability of an actin inhibitor to produce the desired therapeutic effect may be demonstrated in various well known models for the various conditions treated with these therapeutic compounds.

Using human epidermal growth factor receptor HER2+ tumor models with high rates of metastasis, sensitivity to the actin-targeting natural product MycB was determined. Myc B showed cytotoxicity in multiple cancer cell lines, and showed significant inhibition of cell motility and invasiveness at sub-lethal doses (low nM). In a proof-of-principle study, treatments with MycB alone, or in combination with TZ, led to reduced growth of SKOV3 tumors in a xenograft model (FIG. 3). Several simplified synthetic analogues of MycB show similar potency as MycB in disrupting polymerization of purified actin, and were also able to disrupt F-actin in metastatic cancer cells. The most potent of the simplified analogues disrupted the actin cytoskeleton in live HER2+ cells expressing GFP-tagged LifeAct (FIG. 2), and there was evidence of correlation between cytotoxicity in cultured tumor cells (FIG. 8) and potency against actin polymerization in vitro (FIG. 4). Assessment of the effects of these analogues on HER2+ cell migration and invasion also showed measurable reductions in this actin-driven process (FIGS. 5 to 7), albeit with lower potency than MycB. Based on these assays, the most active analogs are 4f (2534)>4g (2453)>4h (2415).

The following working examples further illustrate the present invention and are not intended to be limiting in any respect.

WORKING EXAMPLES

Materials and Methods

All reactions were carried out in flame-dried glassware under an atmosphere of argon using anhydrous solvent. Dichloromethane, tetrahydrofuran (THF), diethyl ether and toluene were dried by passage through activated alumina columns. DMF was dried by passage through activated 5 Å molecular sieves. Triethylamine and dimethylethylamine were distilled from calcium hydride and stored over sodium hydroxide. DBU, 2,6-lutidine and pyridine were distilled from calcium hydride and stored over 4 Å molecular sieves. Isobutyraldehyde was passed through a plug of basic alumina and distilled immediately before use. All other reagents were purchased from Acros, Aldrich, Alfa Aesar, Combi-Blocks, Strem or TCI and used as received unless otherwise stated. Thin layer chromatography (TLC) was performed on EMD Chemicals Inc. (Gibbstown, N.J., USA) 60 $F_{254}$ precoated silica gel plates. Visualisation was accomplished with a UV light, ceric ammonium nitrate solution and/or iodine. Flash chromatography was performed using EMD Chemicals Inc. Silica Gel 60 (0.04-0063 mm particle size). The melting points were obtained from a Büchi Melting Point Apparatus. Solvents for extraction and flash chromatography were reagent grade. Ethyl acetate for flash chromatography was distilled before use. Optical rotations ($[\alpha]_D^{\circ\ C.}$) were measured on an Anton Parr MCP 200 polarimeter with a tungsten halogen lamp (589 nm) at the stated temperature (indicated in ° C. as superscript) using a 0.7 mL quartz cell of 100 mm length; solution concentrations (c) are given in g/100 mL. Infrared spectra were obtained on an Agilent Technologies Cary 630 FT-IR (ATR) spectrometer. Peaks are reported in $cm^{-1}$ with the following relative intensities: vs (very strong), s (strong), m (medium), w (weak) and br (broad). Mass spectra were performed at the Queen's University Mass Spectrometry and Proteokcs Services Unit. $^1$H and $^{13}$C NMR were recorded on a Bruker AV 400 MHz NMR spectrometer in $CDCl_3$, which was obtained from Cambridge Isotope Labs or Sigma Aldrich. NMR data were calibrated using the signal of residual undeuterated solvent as an internal reference ($CHCl_3$, $\delta_H$=7.26 ppm, $\delta_C$=77.16 ppm). $^1$H NMR data are reported as follows: chemical shift (multiplicity, $1^{st}$ order spin system if available, coupling constant and integration). Coupling constants (J) are reported in Hz and apparent splitting patterns are designated using the following abbreviations: s (singlet), d (doublet), t (triplet), q (quartet), quintet, sextet, m (multiplet), br. (broad), app. (apparent) and combinations thereof. $^{13}$C NMR spectra with complete proton decoupling were described with the aid of an APT sequence, separating methylene and quaternary carbons (e, even), from methyl and methine carbons (o, odd). For N-methylformamides existing as mixtures of rotamers, distinguishable resonances of the minor rotamer are denoted with an asterisk.

Example 1

Synthesis of tert-butyl(((3R,5S,6S)-5-methoxy-6-methyloct-7-en-3-yl)oxy)dimethylsilane Scheme 1. Synthesis of tert-butyl(((3R,5S,6S)-5-methoxy-6-methyloct-7-en-3-yl)oxy)dimethylsilane and tert-butyl(((3S,5S,6S)-5-methoxy-2,6-dimethyloct-7-en-3-ly)oxy)dimethylsilane

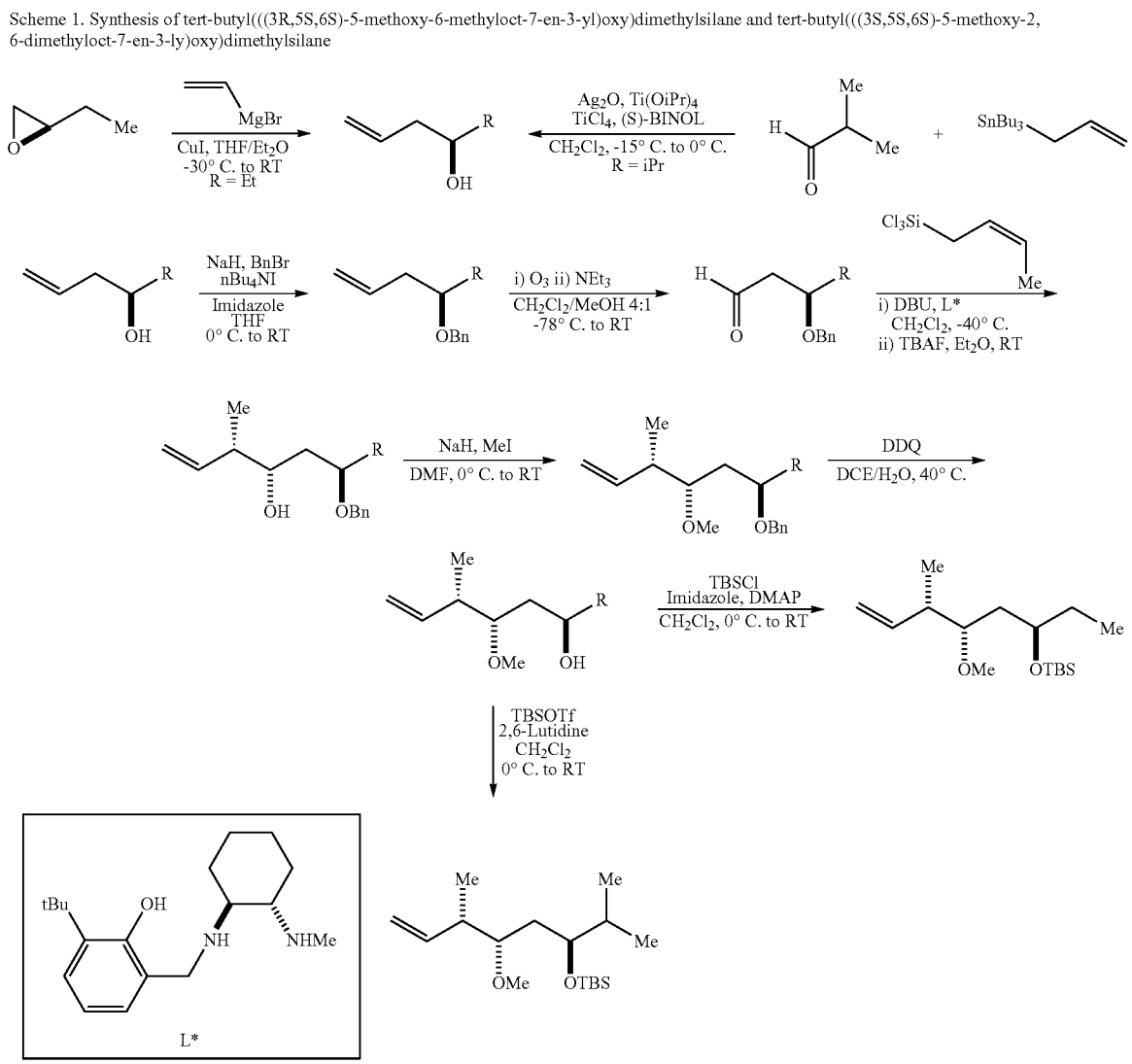

Step 1A. Synthesis of (R)-[(Hex-5-en-3-yloxy) methyl]benzene

To a stirred solution of copper(I) iodide (2.16 g, 11.3 7 mmol, 0.2 equiv.) in diethyl ether (25 mL) at −30° C. was slowly added a solution of vinyl magnesium bromide (85.0 mL, 85.0 mmol; 1.0 M solution in THF, 1.5 equiv.). The dark suspension was stirred at this temperature for 30 minutes and then a solution of (R)-2-ethyloxirane (4.88 mL, 56.87 mmol, 1.0 equiv.) in diethyl ether (13 mL) was added slowly. The mixture was stirred at −30° C. for 30 minutes and then warmed to ambient temperature over 90 minutes. The reaction was quenched with saturated $NH_4Cl$ solution (100 mL) at 0° C. and partitioned with diethyl ether. The organic phase was washed with saturated $NH_4Cl$ solution and aqueous NaCl solution, dried (anhyd. $Na_2SO_4$) and filtered. The diethyl ether was removed on a rotary evaporator at atmospheric pressure and the bulk of the THF was removed by distillation through a vigreux column at atmospheric pressure. The crude alcohol was used directly in the next step without further purification.

Example 2

General Alcohol Benzylation Procedure for the Synthesis of (R)-[(Hex-5-en-3-yloxy)methyl]benzene To a suspension of sodium hydride (washed 3× with anhyd. diethyl ether) (24.5 g, 582 mmol, 57% dispersion in mineral oil, 10 equiv.) in THF (195 mL) at 0° C. was added the crude alcohol prepared in Example 1. Imidazole (198 mg, 2.91 mmol, 0.05 equiv.) was added and the mixture was stirred with the cold bath in place for 30 minutes. Benzyl bromide (6.92 mL, 58.2 mmol, 1.0 equiv.) and tetra-n-butylammonium iodide (2.15 g, 5.82 mmol, 0.1 equiv.) were added and the reaction was slowly warmed to ambient temperature overnight. The reaction was carefully quenched with water (200 mL) at 0° C. and partitioned with ethyl acetate. The organic phases were combined, washed with saturated aqueous NaCl solution, dried (anhyd. $Na_2SO_4$) and filtered. The reaction mixture was concentrated in vacuo and the crude product was purified via flash chromatography ($SiO_2$, gradient elution with 99.5:0.5 to 98:2 pentane/diethyl ether) to furnish the benzyl ether (6.42 g, 59% over two steps). Characterization results were as expected (see D. Becker, U. Kazmaier *Eur. J. Org. Chem.* 2015, 4198).

Example 3

General Ozonolysis Procedure for the Synthesis of (R)-3-(Benzyloxy)pentanal Dry ozone was bubbled through a solution of the olefin (6.03 g, 31.7 mmol, 1.0 equiv.) (prepared using the conditions described in the General Alcohol Benzylation Procedure from Example 2) in dichloromethane/methanol 4:1 (200 mL) at −78° C. until the blue color persisted. Triethylamine (8.83 mL, 63.4 mmol, 2.0 equiv.) was added and the mixture was stirred at −78° C. for 30 minutes and then at ambient temperature overnight. The reaction mixture was concentrated in vacuo and the crude product was purified via flash chromatography ($SiO_2$, gradient elution with 97.5:2.5 to 92.5:7.5 pentane/ethyl acetate) to furnish the aldehyde (3.40 g, 56%). Characterization results were as expected (see S. Motodate, et al., *Chem. Asian J.* 2010, 5, 2221-2230).

Example 4

General Cis Crotylation Procedure for the Synthesis of (3S,4S,6R)-6-(Benzyloxy)-3-methyloct-1-en-4-ol Distilled DBU (5.01 mL, 33.2 mmol, 3.3 equiv.) was added to a solution of the diamine ligand L* (3.22 g, 11.07 mmol, 1.1 equiv.) in dichloromethane (37 mL) at 0° C. (Z)-But-2-en-1-yltrichlorosilane (1.85 mL, 12.1 mmol, 1.2 equiv.) was added slowly and then the cold bath was removed and the mixture was stirred at ambient temperature for 1 hour. The solution was cooled to −40° C., the aldehyde (10.1 mmol, 1 equiv.) (prepared using the conditions described in the General Ozonolysis Procedure from Example 3) was added and the mixture was maintained at this temperature for 15 hours. The mixture was concentrated in vacuo and the residue was taken up in diethyl ether (58 mL) and stirred vigorously at ambient temperature for 20 minutes. The precipitated salts were removed via filtration and the filter cake was washed with diethyl ether. TBAF (11.2 mL, 11.2 mmol, 1.0 M solution in THF, 1.1 equiv.) was added to the filtrate and the mixture was stirred for 2 hours at ambient temperature. The reaction was quenched with 1 N hydrochloric acid solution (50 mL) and partitioned with diethyl ether. The organic phases were combined, washed with water and saturated sodium bicarbonate solution, dried (anhyd. $Na_2SO_4$) and filtered. The reaction mixture was concentrated in vacuo and purified via flash chromatography ($SiO_2$, gradient elution with 95:5 to 92:8 pentane/ethyl acetate) to provide the homoallylic alcohol (1.71 g, 68%, dr 14:1).

Example 5

General Alcohol Methylation Procedure for the Synthesis of {[((3R,5S,6S)-5-Methoxy-6-methyloct-7-en-3-yl)oxy]methyl}benzene Sodium hydride (washed with anhydrous diethyl ether) (1.53 g, 36.2 mmol, 57% dispersion in mineral oil, 5.0 equiv) was suspended in N,N-dimethylformamide (18 mL) and cooled to 0° C. A solution of the alcohol (7.25 mmol, 1.0 equiv.) (prepared using the conditions described in the General Cis Crotylation Procedure from Example 4) in N,N-dimethylformamide (36 mL) was added dropwise via syringe and the suspension was stirred at 0° C. for 10 minutes. Iodomethane (2.27 mL, 36.2 mmol, 5.0 equiv.) was added and the cooling bath was removed. The mixture was stirred at ambient temperature for 3 hours and then cooled to 0° C. and carefully quenched with water (150 mL) and partitioned with diethyl ether. The organic phases were combined, washed with water and saturated sodium chloride solution, dried (anhyd. $Na_2SO_4$) and filtered. The reaction mixture was concentrated in vacuo and purified via flash chromatography ($SiO_2$, gradient elution, pentane/ethyl acetate 98:2 to 97:3) to provide the methyl ether as a clear oil (1.87 g, 92%).

Example 6

General Procedure for Deprotection of Secondary Benzyl Alcohols with DDQ (3R,5S,6S)-5-Methoxy-6-methyloct-7-en-3-ol The benzyl ether (7.05 mmol, 1.0 equiv.) (prepared using the conditions described in the General Alcohol Methylation Procedure from Example 5) was dissolved in DCE/water 9:1 and DDQ (2.08 g, 9.17 mmol, 1.3 equiv.) was added. The suspension was stirred overnight in a 40° C. oil bath and then cooled to ambient temperature. The reaction was quenched with saturated sodium bicarbonate solution (400 mL) and partitioned with dichloromethane. The organic phases were combined, dried (anhyd. $Na_2SO_4$) and filtered. The reaction mixture was concentrated in vacuo and purified via flash chromatography ($SiO_2$, gradient elution, pentane/diethyl ether 90:10 to 50:50) to afford the secondary alcohol (1.07 g, 88%).

Example 7

Synthesis of tert-Butyl(((3R,5S,6S)-5-methoxy-6-methyloct-7-en-3-yl)oxy)dimethylsilane DMAP (36.6 mg, 0.300 mmol 0.12 equiv.), imidazole (404 mg, 5.94 mmol, 2.4 equiv.) and tert-butyldimethylsilyl chloride (512 mg, 3.39 mmol, 1.4 equiv.) were added in quick succession to a solution of the alcohol (430 mg, 2.50 mmol, 1.0 equiv.) (prepared using the conditions described in the General Procedure for Deprotection of Secondary Benzyl Alcohols from Example 6) in dichloromethane (2.9 mL) at 0° C. The mixture was stirred with the cold bath in place for 30 minutes and then at ambient temperature overnight. The reaction was quenched with saturated sodium bicarbonate solution (20 mL) and partitioned with dichloromethane. The organic phases were combined, dried (anhyd. $Na_2SO_4$) and filtered. The reaction mixture was concentrated in vacuo and purified via flash chromatography ($SiO_2$, pentane/diethyl ether 98:2) to provide the title compound as a clear oil (491 mg, 70%).

Example 8

Synthesis of tert-Butyl(((3S,5S,6S)-5-methoxy-2,6-dimethyloct-7-en-3-yl)oxy)dimethylsilane Example 8A Synthesis of (S)-{[(2-Methylhex-5-en-3-yl)oxy]methyl}benzene Titanium(IV) isopropoxide (0.61 mL, 2.08 mmol, 0.15 equiv.) was added to a solution of titanium(IV) chloride (0.69 mL, 0.69 mmol; 1.0 M solution in dichloromethane, 0.05 equiv.) in dichloromethane (14 mL) at 0° C.). After 10 minutes the cold bath was removed and the mixture was stirred at ambient temperature for 2 h. Silver(I) oxide (321 mg, 1.39 mmol, 0.1 equiv.) was added and the mixture was stirred vigorously at ambient temperature in the dark for an additional 5 hours. The mixture was diluted with dichloromethane (28 mL) and (S)-BINOL (794 mg, 2.77 mmol, 0.2 equiv.) was added. The mixture was stirred at ambient temperature for 2 hours and then cooled to −15° C. Isobutyraldehyde (1.27 mL, 13.9 mmol, 1.0 equiv.) and allyltri-n-butyltin (8.60 mL, 27.7 mmol, 2.0 equiv.) were added in quick succession and the mixture was warmed to 0° C. Stirring was continued for ca. 24 hours and then the reaction was quenched with saturated sodium bicarbonate solution (70 mL) and partitioned with diethyl ether. The organic phases were combined, dried (anhyd. $Na_2SO_4$) and filtered. The reaction mixture was concentrated in vacuo and the crude product was purified via flash chromatography ($SiO_2$, gradient elution with 90:10 to 80:20 pentane/diethyl ether) to provide the homoallylic alcohol of sufficient purity for use in further synthesis. The homoallylic alcohol was subjected to the General Alcohol Benzylation Procedure to provide the title compound as a yellow oil (669 mg, 24% over two steps).

Example 9

Synthesis of (S)-3-(Benzyloxy)-4-methylpentanal

The title compound was prepared using the conditions described in the General Ozonolysis Procedure from Example 3 wherein the reactant was (S)-{[(2-methylhex-5-en-3-yl)oxy]methyl}benzene. 475 mg, 66%

Example 10

Synthesis of (3S,4S,6S)-6-(Benzyloxy)-3,7-dimethyloct-1-en-4-ol

The title compound was prepared using the conditions described in the General Cis Crotylation Procedure from Example 4 wherein the reactant was (S)-3-(benzyloxy)-4-methylpentanal. 303 mg, 78%, dr 19:1

Example 11

Synthesis of {[((3S,5S,6S)-5-Methoxy-2,6-dimethyloct-7-en-3-yl)oxy]methyl}benzene The title compound was prepared using the conditions described in the General Alcohol Methylation Procedure from Example 5 wherein the reactant was (3S,4S,6S)-6-(benzyloxy)-3,7-dimethyloct-1-en-4-ol. 367 mg, 93%

Example 12

Synthesis of (3S,5S,6S)-5-Methoxy-2,6-dimethyloct-7-en-3-ol

The title compound was prepared using the conditions described in the General Procedure for Deprotection of Secondary Benzyl Alcohols with DDQ from Example 6 wherein the reactant was {[((3S,5S,6S)-5-methoxy-2,6-dimethyloct-7-en-3-yl)oxy]methyl}benzene. 176 mg, 73%

Example 13

Synthesis of tert-Butyl(((3S,5S,6S)-5-methoxy-2,6-dimethyloct-7-en-3-yl)oxy)dimethylsilane 2,6-Lutidine (0.98 mL, 8.37 mmol, 8.0 equiv.) followed by tert-butyldimethylsilyl trifluoromethanesulfonate (0.96 mL, 4.19 mmol, 4.0 equiv.) were added to a solution of the alcohol (195 mg, 1.05 mmol, 1.0 equiv.) (prepared using the conditions described in the General Procedure for Deprotection of Secondary Benzyl Alcohols from Example 6) in dichloromethane (2.6 mL) at 0° C. The reaction was slowly warmed to ambient temperature over 1 hour and then quenched with saturated ammonium chloride solution and partitioned with dichloromethane. The organic phases were combined, dried (anhyd. $Na_2SO_4$) and filtered. The reaction mixture was concentrated in vacuo and purified via flash chromatography (SiO₂, gradient elution pentane/diethyl ether 99:1 to 98:2) to provide the title compound as a clear oil (275 mg, 87%).

Example 14

Synthesis of (3R,4S,5R,6R)-7-(benzyloxy)-5-methoxy-4,6-dimethylhept-1-en-3-ol and (3S,4S,5R,6R)-7-(benzyloxy)-5-methoxy-4,6-dimethylhept-1-en-3-ol

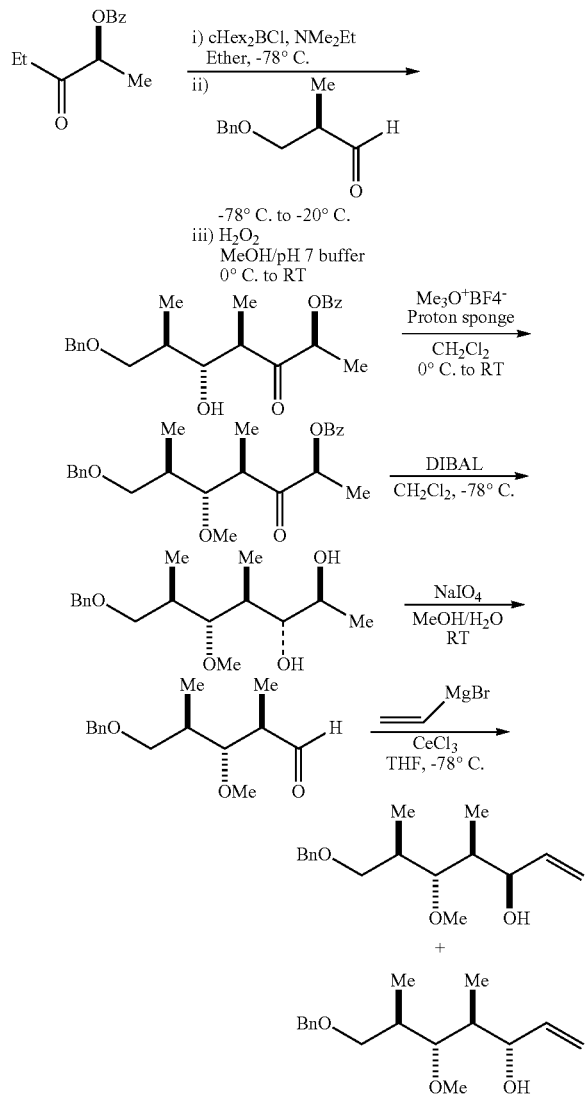

Example 14A

Synthesis of (2S,4R,5R,6R)-7-(Benzyloxy)-5-methoxy-4,6-dimethyl-3-oxoheptan-2-yl benzoate Dimethylethylamine (0.76 mL, 6.98 mmol, 1.8 equiv.) was added to a solution of chlorodicyclohexylborane (1.28 mL, 5.82 mmol, 1.5 equiv.) in diethyl ether (32 mL) at −78° C. (S)-3-Oxopentan-2-yl benzoate (I. Paterson, et al., *Tetrahedron* 2011, 67, 10119)(0.80 g, 3.88 mmol, 1.0 equiv.) was added via syringe and the white suspension was stirred at −78° C. for 10 minutes and then at 0° C. for 2 hours. The mixture was recooled to −78° C. and a solution of freshly prepared (R)-3-(benzyloxy)-2-methylpropanal (L. A. Paquette, et al., *J. Org. Chem.* 2003, 68, 6096)(1.00 g, 5.62 mmol, 1.45 equiv.) in diethyl ether (8 mL) was added dropwise via syringe. The reaction was maintained at −78° C. for 2 hours and then the flask was sealed with plastic paraffin film (PARAFILM™) and kept in a −20° C. freezer for 14 hours. The reaction was quenched with methanol (15 mL), pH 7 buffer solution (15 mL) and 35% aqueous hydrogen peroxide solution (15 mL) at 0° C. The mixture was stirred at ambient temperature for 2 hours and then partitioned between water and dichloromethane. The organic phases were combined, dried (anhyd. MgSO₄) and filtered. The reaction mixture was concentrated in vacuo and purified via flash chromatography (SiO₂, gradient elution diethyl ether/dichloromethane 98:2 to 95.5:4.5) to provide the title compound as a light yellow oil of sufficient purity for use in further synthesis.

To a solution of the β-hydroxy ketone in dichloromethane (17 mL) at 0° C. was added proton sponge (2.01 g, 9.38 mmol, 3.5 equiv.) and trimethyloxonium tetrafluoroborate (0.873 g, 5.90 mmol, 2.2 equiv.). The mixture was stirred with the cold bath in place for 30 minutes and then at ambient temperature overnight. The reaction was diluted with ethyl acetate (15 mL) and filtered through a pad of celite, washing thoroughly with ethyl acetate. The combined organic phases were washed with water, 10% aqueous citric acid solution and brine, dried (anhyd. Na₂SO₄) and filtered. The reaction mixture was concentrated in vacuo and purified via flash chromatography (SiO₂, gradient elution pentane/ethyl acetate 95:5 to 90:10) to provide the title compound as a light yellow oil (0.773 g, dr 9:1, 50% over two steps)

Example 15

Synthesis of (2S,4S,5R,6R)-7-(Benzyloxy)-5-methoxy-4,6-dimethylheptane-2,3-diol

DIBAL (123 mL, 123 mmol; 1.0 M solution in hexanes, 4.0 equiv.) was slowly added to a solution of the ketone (12.3 g, 30.8 mmol) in dichloromethane (615 mL) at −78° C. The reaction was stirred at −78° C. for 1 hour and then diluted with diethyl ether and transferred to an ice bath before being carefully quenched with water (4.9 mL), 15% aqueous sodium hydroxide solution (4.9 mL) and water (12.3 mL). The vigorously stirring mixture was warmed to ambient temperature and stirred for 15 minutes. Anhyd. MgSO₄ was added and stirring was continued for an additional 15 minutes. The mixture was filtered and the filter cake was washed thoroughly with diethyl ether. The filtrate was concentrated in vacuo and purified via flash chromatography (SiO₂, gradient elution diethyl ether/dichloromethane 90:10 to 5:95) to provide the title compound as a light yellow oil (5.04 g, 55%) as a mixture of four diastereomers that was used without further purification.

Example 16

Synthesis of (3R,4S,5R,6R)-7-(Benzyloxy)-5-methoxy-4,6-dimethylhept-1-en-3-ol and (3S,4S,5R,6R)-7-(benzyloxy)-5-methoxy-4,6-dimethylhept-1-en-3-ol Sodium periodate (368 mg, 17.21 mmol, 6.0 equiv.) was added to a solution of the diol (850 mg, 2.87 mmol, 1.0 equiv.) in methanol/water 3:1 (29 mL). The mixture was stirred at ambient temperature for 30 minutes and then quenched with water (65 mL) and partitioned with diethyl ether. The combined organic phases were dried (anhyd. MgSO$_4$), filtered and concentrated in vacuo to provide the crude aldehyde that was used without further purification.

THF (20 mL) was added to anhyd. cerium(III) chloride (1.27 g, 5.15 mmol, 2.13 equiv.) at 0° C. with vigorous stirring. The mixture was stirred at ambient temperature for 2.5 hours and then cooled to −78° C. and treated with vinyl bromide (4.84 mL, 4.84 mmol; 1.0 M solution in THF, 2.0 equiv.). The yellow suspension was stirred at −78° C. for 2 hours and then a solution of the crude aldehyde (606 mg, 2.42 mmol, 1.0 equiv.) in THF (13 mL) was added dropwise via syringe. Stirring was continued at −78° C. for 2 hours and then the reaction was quenched with saturated ammonium chloride solution (100 mL) and partitioned with ethyl acetate. The organic phases were combined, washed with saturated aqueous NaCl solution, dried (anhyd. Na$_2$SO$_4$) and filtered. The reaction mixture was concentrated in vacuo and the crude product was purified via flash chromatography (SiO$_2$, gradient elution with 95:5 to 90:10 pentane/ethyl acetate) (3R,4S,5R,6R)-7-(Benzyloxy)-5-methoxy-4,6-dimethylhept-1-en-3-ol 273 mg, 40%

Color and State: Clear oil.

(3S,4S,5R,6R)-7-(Benzyloxy)-5-methoxy-4,6-dimethylhept-1-en-3-ol 158 mg, 23%.

Color and State: Clear oil.

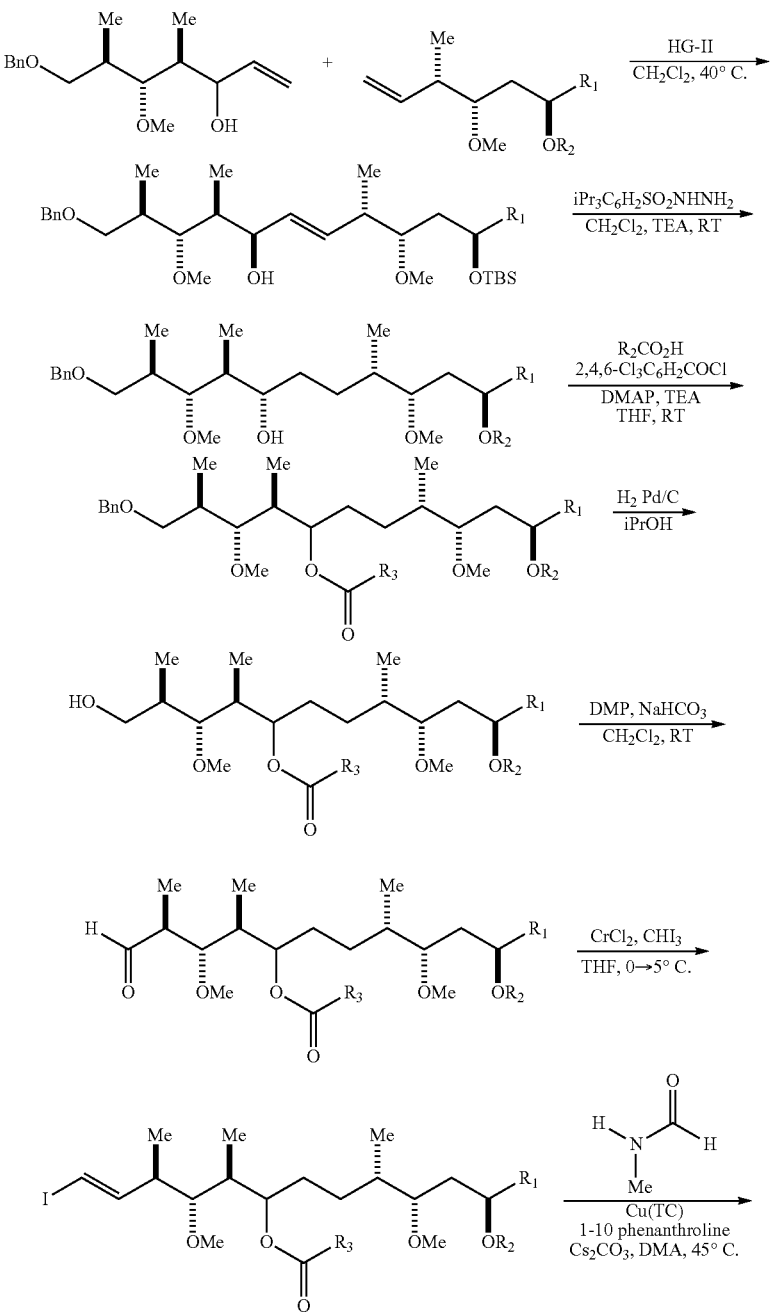

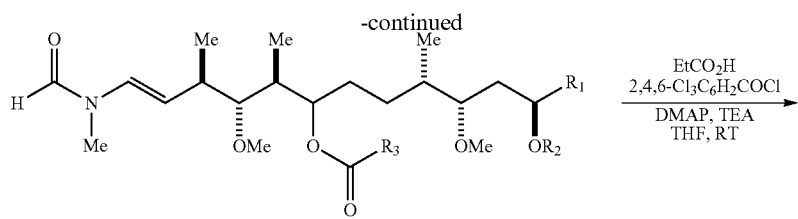

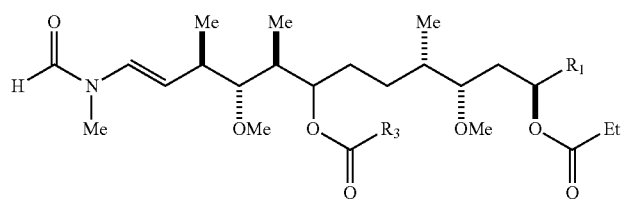

$R_2 = H$

Example 17

Synthesis of (3R,5S,6S,9R,10S,11R,12R,E)-5,11-dimethoxy-6,10,12-trimethyl-14-(N-methylformamido)tetradec-13-ene-3,9-diyldipropionate (7)

Example 17A

Synthesis of (2R,3R,4S,5R,8S,9S,11R)-1-(Benzyloxy)-11-((tert-butyldimethylsilyl)oxy)-3,9-dimethoxy-2,4,8-trimethyltridecan-5-ol General Procedure for Olefin Metathesis Hoveyda-Grubbs second generation catalyst (16.9 mg, 0.027 mmol, 0.1 equiv.) was added to a solution of the allylic alcohol (0.269 mmol, 1.0 equiv.) (prepared in Example 16) and homoallylic ether (0.674-1.08 mmol, 2.5-4.0 equiv.) under an atmosphere of argon. The solution was gently refluxed for ca. 6 hours and then concentrated in vacuo to afford the crude product. Purification by flash chromatography ($SiO_2$, gradient elution with 98:2 to 90:10 pentane/ethyl acetate) furnished the products. In most cases flash chromatography afforded mixtures of the product and catalyst that were carried forward General Procedure for Double Bond Reduction 2,4,6-Triisopropylbenzenesulfonohydrazide (N. Cusack, et al., *Tetrahedron* 1976, 32, 2157)(544 mg, 1.82 mmol, 10.0 equiv.) was added to a solution of the olefin (0.182 mmol, 1.0 equiv.) (prepared using the conditions described in the General Procedure for Olefin Metathesis) in dichloromethane (4.55 mL) under argon. Anhyd. triethylamine (802 µL, 5.76 mmol, 31.6 equiv.) was added and the solution was stirred overnight at ambient temperature. The reaction was quenched with saturated sodium bicarbonate solution (50 mL) and partitioned with hexanes/diethyl ether 1:1. The organic phases were combined, dried (anhyd. $Na_2SO_4$) and filtered. The reaction mixture was concentrated in vacuo and the crude product was purified via flash chromatography ($SiO_2$, gradient elution with 98:2:0.5 to 92:8:0.5 pentane/ethyl acetate/triethylamine) to provide the saturated alcohol (74.1 mg, 51% over two steps).

Example 18

General Procedure A for Yamaguchi Esterification (2R,3R,4S,5R,8S,9S,11R)-1-(Benzyloxy)-11-((tert-butyldimethylsilyl)oxy)-3,9-dimethoxy-2,4,8-trimethyltridecan-5-yl propionate Anhyd. triethylamine (57.5 µL, 0.413 mmol, 3.0 equiv.) and 2,4,6-trichlorobenzoyl chloride (64.5 µL, 0.413 mmol, 3.0 equiv.) were added to a solution of the carboxylic acid (0.413 mmol, 3.0 equiv.) in THF (1.4 mL) and the mixture was stirred at RT for ca. 2 hours. Using a syringe tip filter to remove the precipitated salts, the mixed anhydride solution was then added to a solution of the secondary alcohol (0.138 mmol, 1.0 equiv.) (prepared using the conditions described in the General Procedure for Double Bond Reduction from Example 17) and DMAP (33.6 mg, 0.275 mmol, 2.0 equiv.) in THF (2.1 mL) at 0° C. The mixture was stirred at ambient temperature overnight and then concentrated in vacuo to afford the crude product. Purification by flash chromatography ($SiO_2$, gradient elution with 97.5:2.5 to 90:10 pentane/ethyl acetate) furnished the ester (76.1 mg, 93%).

Example 19

General Procedure for Deprotection of Primary Benzyl Alcohols (2R,3R,4S,5R,8S,9S,11R)-11-((tert-Butyldimethylsilyl)oxy)-1-hydroxy-3,9-dimethoxy-2,4,8-trimethyltridecan-5-yl propionate 10% Palladium on charcoal (21.3 mg, 0.18 equiv.) was added to a solution of the benzyl ether (0.111 mmol, 1.0 equiv.) (prepared using the conditions described in the General Procedure A for Yamaguchi Esterification from Example 18) in isopropanol (8.5 mL). The flask was evacuated, backfilled with hydrogen and stirred overnight under an atmosphere of hydrogen. The mixture was filtered through a pad of celite to remove the catalyst and the filter cake was washed with ethyl acetate. The filtrate was concentrated in vacuo to afford the crude product. Purification by flash chromatography (SiO$_2$, gradient elution with 90:10 to 75:25 pentane/ethyl acetate) furnished the primary alcohol (41.4 mg, 74%).

Example 20

General Procedure for Alcohol Oxidation

In the glove box sodium bicarbonate (76.0 mg, 0.900 mmol, 11.2 equiv.) and Dess-Martin Periodinane (75.0 mg, 0.177 mmol, 2.2 equiv.) were added to a solution of the primary alcohol (0.081 mmol) (prepared using the conditions described in the General Procedure for Deprotection of Primary Benzyl Alcohols from Example 19) in dichloromethane (1.6 mL). The mixture was stirred at RT in the glove box for 2 hours and then removed from the glove box and quenched with saturated sodium bicarbonate/saturated sodium thiosulfate 1:1 (12 mL) and partitioned with hexanes/diethyl ether 9:1. The organic phases were combined, dried (anhyd. Na$_2$SO$_4$) and filtered. The reaction mixture was concentrated in vacuo to afford the crude product that was used directly in the next step.

Example 21

General Procedure for Takai Olefination and TBS Deprotection (3R,4R,5S,6R,9S,10S,12R,E)-12-Hydroxy-1-iodo-4, 10-dimethoxy-3,5,9-trimethyltetradec-1-en-6-yl propionate Anhydrous THF (4.6 mL) was added to a mixture of the crude aldehyde (0.067 mmol, 1.0 equiv.) (prepared using the conditions described in the General Procedure for Alcohol Oxidation from Example 20) and iodoform (156 mg, 0.397 mmol, 5.9 equiv.). The solution was transferred via syringe to a Schlenk flask containing anhyd. chromium(III) chloride (138 mg, 1.12 mmol, 16.7 equiv.) at 0° C. The mixture was stirred for 2 hours, during which time the temperature was allowed to increase to 5° C. The reaction was quenched with sodium bicarbonate/saturated sodium thiosulfate 4:1 and partitioned with ethyl acetate. The organic phases were combined, dried (anhyd. Na$_2$SO$_4$) and filtered. If necessary, TBS deprotection was completed by dissolving the residue in ethanol/3 N HCl 4:1 (38 mL/mmol) and stirring at room temperature for ca. 90 minutes (TLC control). The reaction was quenched with saturated sodium bicarbonate solution and partitioned with ethyl acetate. The organic phases were combined, dried (anhyd. Na$_2$SO$_4$) and filtered. The reaction mixture was concentrated in vacuo and the crude product was purified via flash chromatography (SiO$_2$, gradient elution with 90:10 to 75:25 pentane/ethyl acetate) to furnish the vinyl iodide (4.2 mg, 32% over three steps).

Example 22

General Procedure for the Goldberg Reaction (3R,4R,5S,6R,9S,10S,12R,E)-12-Hydroxy-4,10-dimethoxy-3,5,9-trimethyl-1-(N methylformamido) tetradec-1-en-6-yl propionate (1)

In the glove box N-methylformamide (55.3 mg, 0.937 mmol, 50 equiv.), cesium carbonate (10.9 mg, 33.5 μmol, 1.8 equiv.), 1,10-phenanthroline (13.5 mg, 74.9 μmol, 4.0 equiv.) and copper(I) thiophene-2-carboxylate (7.1 mg, 37 μmol, 2.0 equiv.) were added to a solution of the vinyl iodide (19 μmol, 1.0 equiv.) (prepared using the conditions described in the General Procedure for Takai Olefination and Deprotection from Example 21) in N,N-dimethylacetamide (0.42 mL). The flask was fitted with a septa, removed from the glove box and evacuated and backfilled with argon. The mixture was stirred overnight in a 45° C. oil bath. The reaction was quenched with pH 7 buffer solution (5 mL) and partitioned with diethyl ether. The organic phases were combined, washed with saturated sodium chloride solution, dried (anhyd. Na$_2$SO$_4$) and filtered. The reaction mixture was concentrated in vacuo and the crude product was purified via flash chromatography (neutralized SiO$_2$, gradient elution with 60:40 to 10:90 pentane/ethyl acetate) to furnish the vinyl formamide (4.6 mg, 55%).

(3R,5S,6S,9R,10S,11R,12R,E)-5,11-dimethoxy-6,10, 12-trimethyl-14-(N-methylformamido)tetradec-13-ene-3,9-diyl dipropionate (7)

Prepared using the conditions described in the General Procedure A for Yamaguchi Esterification from Example 18 wherein the reactants were (3R,4R,5S,6R,9S,10S,12R,E)-12-hydroxy-4,10-dimethoxy-3,5,9-trimethyl-1-(N methylformamido)tetradec-1-en-6-yl propionate and propionic acid. 2.7 mg, 42%.

Example 23

Synthesis of (3R,5S,6S,9S,10S,11R,12R,E)-5,11-Dimethoxy-6,10,12-trimethyl-14-(N-methylformamido)tetradec-13-ene-3,9-diyldipropionate (8)

(2R,3R,4S,5S,8S,9S,11R)-1-(Benzyloxy)-11-((tert-butyldimethylsilyl)oxy)-3,9-dimethoxy-2,4,8-trimethyltridecan-5-ol The title compound was prepared using the conditions described in the General Procedure for Olefin Metathesis and Double Bond Reduction from Example 17 wherein the reactants were (3S,4S,5R,6R)-7-(benzyloxy)-5-methoxy-4, 6-dimethylhept-1-en-3-ol (1 equiv.) and tert-butyl(((3R,5S, 6S)-5-methoxy-6-methyloct-7-en-3-yl)oxy)dimethylsilane (4 equiv.). 73.6 mg, 38% over two steps.

(2R,3R,4S,5S,8S,9S,11R)-1-(Benzyloxy)-11-((tert-butyldimethylsilyl)oxy)-3,9-dimethoxy-2,4,8-trimethyltridecan-5-yl propionate The title compound was prepared using the conditions described in the General Procedure A for Yamaguchi Esterification from Example 18 wherein the reactant were (2R, 3R,4S,5S,8S,9S,11R)-1-(benzyloxy)-11-((tert-butyldimethylsilyl)oxy)-3,9-dimethoxy-2,4,8-trimethyltridecan-5-ol and propionic acid. 56.5 mg, 72%.

(2R,3R,4S,5S,8S,9S,11R)-11-((tert-Butyldimethylsilyl)oxy)-1-hydroxy-3,9-dimethoxy-2,4,8-trimethyltridecan-5-yl propionate The title compound was prepared using the conditions described in the General Procedure for Deprotection of Primary Benzyl Alcohols from Example 19 wherein the reactant was (2R,3R,4S,5S,8S,9S,11R)-1-(benzyloxy)-11-((tert-butyldimethylsilyl)oxy)-3,9-dimethoxy-2,4,8-trimethyltridecan-5-yl propionate. 40.7 mg, 84%.

(3R,4R,5S,6S,9S,10S,12R,E)-12-Hydroxy-1-iodo-4,10-dimethoxy-3,5,9-trimethyltetradec-1-en-6-yl propionate The title compound was prepared using the conditions described in the General Procedures for Alcohol Oxidation, Takai Olefination and TBS Deprotection from Examples 20 and 21 wherein the reactant was (2R,3R,4S,5S,8S,9S,11R)-11-((tert-butyldimethylsilyl)oxy)-1-hydroxy-3,9-dimethoxy-2,4,8-trimethyltridecan-5-yl propionate. 6.2 mg, 46% over three steps.

(3R,4R,5S,6S,9S,10S,12R,E)-12-Hydroxy-4,10-dimethoxy-3,5,9-trimethyl-1-(N-methylformamido)tetradec-1-en-6-yl propionate (2)

The title compound was prepared using the conditions described in the General Procedure for the Goldberg Reaction from Example 22 wherein the reactant was (3R,4R,5S,6S,9S,10S,12R,E)-12-hydroxy-1-iodo-4,10-dimethoxy-3,5,9-trimethyltetradec-1-en-6-yl propionate.
7.3 mg, 67%.

(3R,5S,6S,9S,10S,11R,12R,E)-5,11-Dimethoxy-6,10,12-trimethyl-14-(N-methylformamido)tetradec-13-ene-3,9-diyldipropionate (8)

The title compound was prepared using the conditions described in the General Procedure A for Yamaguchi Esterification from Example 18 wherein the reactants were (3R,4R,5S,6S,9S,10S,12R,E)-12-Hydroxy-4,10-dimethoxy-3,5,9-trimethyl-1-(N-methylformamido)tetradec-1-en-6-yl propionate and propionic acid. 2.1 mg, 52%.

Example 25

Synthesis of (3R,4R,5S,6R,9S,10S,12S,E)-4,10-Dimethoxy-3,5,9,13-tetramethyl-1-(N-methylformamido)-12-(propionyloxy)tetradec-1-en-6-yl isobutyrate (10)

(2R,3R,4S,5R,8S,9S,11S)-1-(Benzyloxy)-11-((tert-butyldimethylsilyl)oxy)-3,9-dimethoxy-2,4,8,12-tetramethyltridecan-5-ol The title compound was prepared using the conditions described in the General Procedure for Olefin Metathesis and Double Bond Reduction from Example 17 wherein the reactants were (3R,4S,5R,6R)-7-(benzyloxy)-5-methoxy-4,6-dimethylhept-1-en-3-ol (1 equiv.) and tert-butyl(((3S,5S,6S)-5-methoxy-2,6-dimethyloct-7-en-3-yl)oxy)dimethylsilane (2.5 equiv.).
17.9 mg, 53% over two steps.

(2R,3R,4S,5R,8S,9S,11S)-1-(Benzyloxy)-11-((tert-butyldimethylsilyl)oxy)-3,9-dimethoxy-2,4,8,12-tetramethyltridecan-5-yl isobutyrate The title compound was prepared using the conditions described in the General Procedure A for Yamaguchi Esterification from Example 18 wherein the reactants were 2R,3R,4S,5R,8S,9S,11S)-1-(benzyloxy)-11-((tert-butyldimethylsilyl)oxy)-3,9-dimethoxy-2,4,8,12-tetramethyltridecan-5-ol and isobutyric acid.
26.2 mg, 87%.

(2R,3R,4S,5R,8S,9S,11S)-11-((tert-Butyldimethylsilyl)oxy)-1-hydroxy-3,9-dimethoxy-2,4,8,12-tetramethyltridecan-5-yl isobutyrate The title compound was prepared using the conditions described in the General Procedure for Deprotection of Primary Benzyl Alcohols from Example 19 wherein the reactant was (2R,3R,4S,5R,8S,9S,11S)-1-(benzyloxy)-11-((tert-butyldimethylsilyl)oxy)-3,9-dimethoxy-2,4,8,12-tetramethyltridecan-5-yl isobutyrate.
21.7 mg, 97%.

(3R,4R,5S,6R,9S,10S,12S,E)-12-Hydroxy-1-iodo-4,10-dimethoxy-3,5,9,13-tetramethyltetradec-1-en-6-ylisobutyrate The title compound was prepared using the conditions described in the General Procedures for Alcohol Oxidation, Takai Olefination and TBS Deprotection from Examples 20 and 21 wherein the reactant was (2R,3R,4S,5R,8S,9S,11S)-11-((tert-butyldimethylsilyl)oxy)-1-hydroxy-3,9-dimethoxy-2,4,8,12-tetramethyltridecan-5-yl isobutyrate.
8.8 mg, 38% over three steps.

(3R,4R,5S,6R,9S,10S,12S,E)-12-Hydroxy-4,10-dimethoxy-3,5,9,13-tetramethyl-1-(N-methylformamido)tetradec-1-en-6-yl isobutyrate (4)

The title compound was prepared using the conditions described in the General Procedure for the Goldberg Reaction from Example 22 wherein the reactant was (3R,4R,5S,6R,9S,10S,12S,E)-12-hydroxy-1-iodo-4,10-dimethoxy-3,5,9,13-tetramethyltetradec-1-en-6-yl isobutyrate. 3.0 mg, 65%.

(3R,4R,5S,6R,9S,10S,12S,E)-4,10-Dimethoxy-3,5,9,13-tetramethyl-1-(N-methylformamido)-12-(propionyloxy)tetradec-1-en-6-yl isobutyrate (10)

The title compound was prepared using the conditions described in the General Procedure A for Yamaguchi Esterification from Example 18 wherein the reactants were 3R,4R,5S,6R,9S,10S,12S,E)-12-hydroxy-4,10-dimethoxy-3,5,9,13-tetramethyl-1-(N-methylformamido)tetradec-1-en-6-yl isobutyrate and propionic acid. 2.7 mg, 60%.

Example 26

Synthesis of (3R,4R,5S,6R,9S,10S,12R,E)-4,10-Dimethoxy-3,5,9-trimethyl-1-(N-methylformamido)-12-propoxytetradec-1-en-6-yl isobutyrate (5)

(2R,3R,4S,5R,8S,9S,11R,E)-1-(Benzyloxy)-3,9-dimethoxy-2,4,8-trimethyl-11-propoxytridec-6-en-5-ol The title compound was prepared using the conditions described in the General Procedure for Olefin Metathesis from Example 17 wherein the reactants were (3R,4S,5R,6R)-7-(benzyloxy)-5-methoxy-4,6-dimethylhept-1-en-3-ol (1 equiv.) and (3S,4S,6R)-4-methoxy-3-methyl-6-propoxyoct-1-ene (2.5 equiv.). 43.3 mg, 65%

(2R,3R,4S,5R,8S,9S,11R)-1-(Benzyloxy)-3,9-dimethoxy-2,4,8-trimethyl-11-propoxytridecan-5-ol The title compound was prepared using the conditions described in the General Procedure for Double Bond Reduction from Example 17 wherein the reactant was (2R,3R,4S, 5R,8S,9S,11R,E)-1-(benzyloxy)-3,9-dimethoxy-2,4,8-trimethyl-11-propoxytridec-6-en-5-ol. 33.5 mg, 87%.

(2R,3R,4S,5R,8S,9S,11R)-1-(Benzyloxy)-3,9-dimethoxy-2,4,8-trimethyl-11-propoxytridecan-5-yl isobutyrate The title compound was prepared using the conditions described in the General Procedure A for Yamaguchi Esterification from Example 18 wherein the reactants were (2R,3R,4S,5R,8S,9S,11R)-1-(Benzyloxy)-3,9-dimethoxy-2,4,8-trimethyl-11-propoxytridecan-5-ol and isobutyric acid. 34.4 mg, 90%.

(2R,3R,4S,5R,8S,9S,11R)-1-hydroxy-3,9-dimethoxy-2,4,8-trimethyl-11-propoxytridecan-5-yl isobutyrate The title compound was prepared using the conditions described in the General Procedure for Deprotection of Primary Benzyl Alcohols from Example 19 wherein the reactant was (2R,3R,4S,5R,8S,9S,11R)-1-(benzyloxy)-3,9-dimethoxy-2,4,8-trimethyl-11-propoxytridecan-5-yl isobutyrate. 25.0 mg, 90%.

(3R,4R,5S,6R,9S,10S,12R,E)-1-Iodo-4,10-dimethoxy-3,5,9-trimethyl-12-propoxytetradec-1-en-6-yl isobutyrate The title compound was prepared using the conditions described in the General Procedures for Alcohol Oxidation and Takai Olefination from Examples 20 and 21 wherein the reactant was (2R,3R,4S,5R,8S,9S,11R)-1-hydroxy-3,9-dimethoxy-2,4,8-trimethyl-11-propoxytridecan-5-yl isobutyrate. 18.0 mg, 54% over two steps.

(3R,4R,5S,6R,9S,10S,12R,E)-4,10-Dimethoxy-3,5,9-trimethyl-1-(N-methylformamido)-12-propoxytetradec-1-en-6-yl isobutyrate (5)

The title compound was prepared using the conditions described in the General Procedure for the Goldberg Reaction from Example 22 wherein the reactant was (3R,4R,5S,6R,9S,10S,12R,E)-1-iodo-4,10-dimethoxy-3,5,9-trimethyl-12-propoxytetradec-1-en-6-yl isobutyrate. 4.8 mg, 78%.

Example 27

Synthesis of (3R,4R,5S,6R,9S,10S,12R,E)-4,10-Dimethoxy-3,5,9-trimethyl-1-(N-methylformamido)-12-(propionyloxy)tetradec-1-en-6-yl isobutyrate (9)

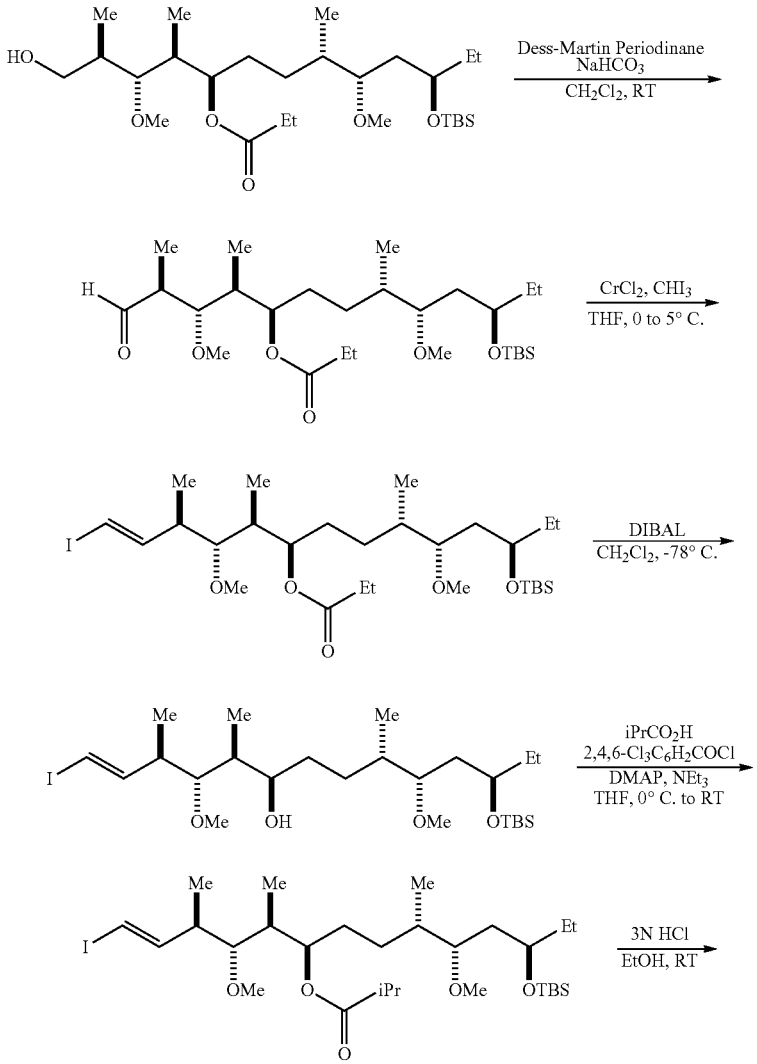

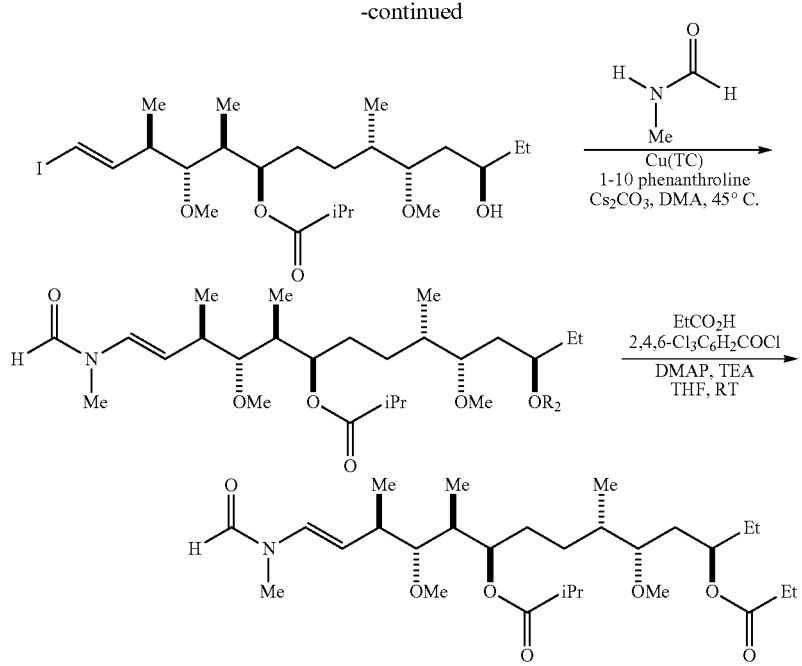

General Procedure for Takai Olefination

To obtain OTBS vinyl iodides, the General Procedure for Takai Olefination from Example 21 was modified slightly to prevent TBS deprotection. The reaction was quenched with saturated sodium bicarbonate and partitioned with hexanes/ethyl acetate 95:5. The organic phases were combined, dried (anhyd. $Na_2SO_4$) and filtered. The reaction mixture was concentrated in vacuo and the crude product was purified via flash chromatography (neutralized $SiO_2$, gradient elution with 98.5:1.5 to 97.5:2.5 pentane/ethyl acetate) to afford the OTBS vinyl iodide. (3R,4R,5S,6R,9S,10S,12R,E)-12-((tert-Butyldimethylsilyl)oxy)-1-iodo-4,10-dimethoxy-3,5,9-trimethyltetradec-1-en-6-yl propionate 3.6 mg, 35% over two steps.

(3R,4R,5S,6R,9S,10S,12R,E)-12-((tert-Butyldimethylsilyl)oxy)-1-iodo-4,10-dimethoxy-3,5,9-trimethyltetradec-1-en-6-ol DIBAL (80 µL, 0.08 mmol; 1.0 M solution in hexanes, 2.0 equiv.) was diluted with dichloromethane (0.5 mL) and added dropwise via syringe to a solution of the ester (25.0 mg, 0.04 mmol, 1.0 equiv.) in dichloromethane at −78° C. The mixture was maintained at this temperature for 10 minutes and then quenched with methanol (1 mL) and saturated Rochelle's salt solution (5 mL). The vigorously stirred mixture was warmed to ambient temperature and partitioned with dichloromethane. The organic phases were combined, dried (anhyd. $Na_2SO_4$) and filtered. The reaction mixture was concentrated in vacuo and the crude product was purified via flash chromatography ($SiO_2$, gradient elution with 95:5 to 85:15 pentane/ethyl acetate) to furnish the title compound as a clear oil (18.2 mg, 80%)

(3R,4R,5S,6R,9S,10S,12R,E)-12-((tert-Butyldimethylsilyl)oxy)-1-iodo-4,10-dimethoxy-3,5,9-trimethyltetradec-1-en-6-yl isobutyrate The title compound was prepared using the conditions described in the General Procedure A for Yamaguchi Esterification from Example 18 wherein the reactants were (3R,4R,5S,6R,9S,10S,12R,E)-12-((tert-butyldimethylsilyl)oxy)-1-iodo-4,10-dimethoxy-3,5,9-trimethyltetradec-1-en-6-ol and isobutyric acid. 6.2 mg, 97%

(3R,4R,5S,6R,9S,10S,12R,E)-12-Hydroxy-1-iodo-4,10-dimethoxy-3,5,9-trimethyltetradec-1-en-6-yl isobutyrate 3 N HCl solution (0.33 mL, 0.99 mmol, 21.1 equiv.) was added to a solution of the silyl ether (30.0 mg, 46.8 µmol, 1.0 equiv.) and the mixture was stirred at ambient temperature for 90 minutes. The reaction was quenched with saturated sodium bicarbonate solution (2 mL) and partitioned with ethyl acetate. The organic phases were combined, dried (anhyd. $Na_2SO_4$) and filtered. The reaction mixture was concentrated in vacuo and the crude product was purified via flash chromatography ($SiO_2$, gradient elution with 90:10 to 75:25 pentane/ethyl acetate) to furnish the title compound as a yellow oil (22.2 mg, 90%).

(3R,4R,5S,6R,9S,10S,12R,E)-12-Hydroxy-4,10-dimethoxy-3,5,9-trimethyl-1-(N-methylformamido)tetradec-1-en-6-yl isobutyrate (3)

The title compound was prepared using the conditions described in the General Procedure for the Goldberg Reaction from Example 22 wherein the reactant was (3R,4R,5S,6R,9S,10S,12R,E)-12-hydroxy-1-iodo-4,10-dimethoxy-3,5,9-trimethyltetradec-1-en-6-yl isobutyrate. 17.7 mg, 73%.

(3R,4R,5S,6R,9S,10S,12R,E)-4,10-Dimethoxy-3,5,9-trimethyl-1-(N-methylformamido)-12-(propionyloxy)tetradec-1-en-6-yl isobutyrate (9)

The title compound was prepared using the conditions described in the General Procedure A for Yamaguchi Esterification from Example 18 wherein the reactants were (3R,4R,5S,6R,9S,10S,12R,E)-12-hydroxy-4,10-dimethoxy-3,5, 9-trimethyl-1-(N-methylformamido)tetradec-1-en-6-yl isobutyrate and propionic acid. 3.8 mg, 99%.

Example 28

Synthesis of (R)-(3R,4R,5S,6R,9S,10S,12R,E)-4,10-Dimethoxy-3,5,9-trimethyl-1-(N-methylformamido)-12-(propionyloxy)tetradec-1-en-6-yl 2-methoxypropanoate (11)

Using a syringe tip filter to remove the precipitated salts, the mixed anhydride solution was then added to a flask containing the secondary alcohol (10.0 mg, 17.5 µmol 1.0 equiv.) and DMAP (6.2 mg, 51 µmol, 2.9 equiv.) at 0° C. The mixture was stirred at ambient temperature overnight and then concentrated in vacuo to afford the crude product. Purification by flash chromatography (SiO₂, gradient elution with 98:2 to 90:10 pentane/ethyl acetate) furnished the title compound as a clear oil (10.7 mg, 93%).

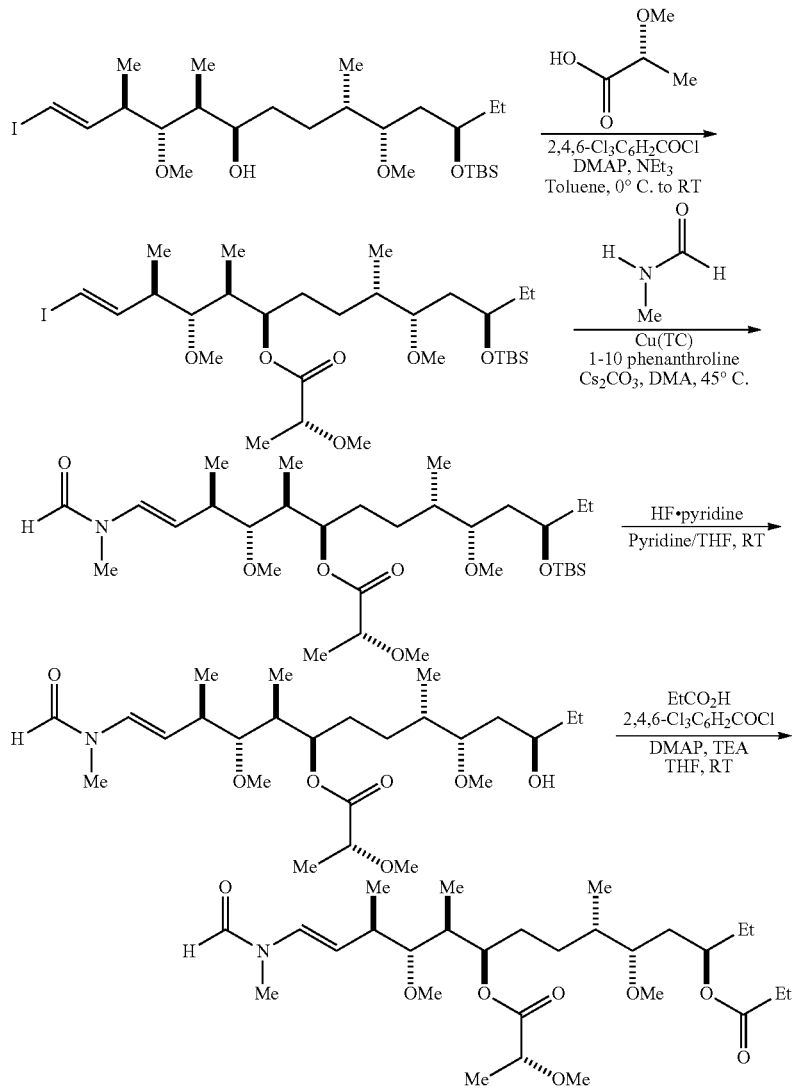

(R)-(3R,4R,5S,6R,9S,10S,12R,E)-12-((tert-Butyldimethylsilyl)oxy)-1-iodo-4,10-dimethoxy-3,5,9-trimethyltetradec-1-en-6-yl 2-methoxypropanoate General Procedure B for Yamaguchi Esterification Anhyd. triethylamine (11.7 µL, 83.9 µmol, 4.8 equiv.) and 2,4,6-trichlorobenzoyl chloride (6.6 µL, 42 µmol, 2.4 equiv.) were added to a solution of (R)-2-methoxypropanoic acid (Barrett, A. G. M. et al. *J. Org. Chem.* (1998) 63: 5818) (5.8 mg, 42 µmol, 2.4 equiv) in THF (0.24 mL) and the mixture was stirred at RT for ca. 2 hours. The THF was removed in vacuo and the residue was diluted with toluene (0.60 mL).

(R)-(3R,4R,5S,6R,9S,10S,12R,E)-12-((tert-Butyldimethylsilyl)oxy)-4,10-dimethoxy-3,5,9-trimethyl-1-(N-methylformamido)tetradec-1-en-6-yl 2-methoxypropanoate The title compound was prepared using the conditions described in the General Procedure for the Goldberg Reaction from Example 22 wherein the reactant was (R)-(3R,4R,5S,6R,9S,10S,12R,E)-12-((tert-butyldimethylsilyl)oxy)-1-iodo-4,10-dimethoxy-3,5,9-trimethyltetradec-1-en-6-yl 2-methoxypropanoate. 8.8 mg, 92%.

39

(R)-(3R,4R,5S,6R,9S,10S,12R,E)-12-Hydroxy-4,10-dimethoxy-3,5,9-trimethyl-1-(N-methylformamido)tetradec-1-en-6-yl 2-methoxypropanoate (6)

A stock solution of HF-pyridine was prepared from THF (2.2 mL), pyridine (1.2 mL) and HF-pyridine (0.51 mL, 70% HF). The TBS ether (8.8 mg, 15 µmol) was treated with the stock solution (0.82 mL) and the mixture was stirred at ambient temperature for ca. 6 hours. The reaction was quenched with saturated sodium bicarbonate solution (6 mL) followed by solid sodium bicarbonate and partitioned with ethyl acetate. The organic phases were combined, dried (anhyd. $Na_2SO_4$) and filtered. The reaction mixture was concentrated in vacuo and the crude product was purified via flash chromatography (neutralized $SiO_2$, gradient elution with 50:50 to 10:90 pentane/ethyl acetate) to furnish the title compound as a colorless oil (5.1 mg, 71%).

40

(R)-(3R,4R,5S,6R,9S,10S,12R,E)-4,10-Dimethoxy-3,5,9-trimethyl-1-(N-methylformamido)-12-(propionyloxy)tetradec-1-en-6-yl 2-methoxypropanoate (11)

Prepared using the conditions described in the General Procedure A for Yamaguchi Esterification from Example 18 wherein the reactants were (R)-(3R,4R,5S,6R,9S,10S,12R,E)-12-hydroxy-4,10-dimethoxy-3,5,9-trimethyl-1-(N-methylformamido)tetradec-1-en-6-yl 2-methoxypropanoate and propionic acid. 3.5 mg, 65%.

Example 29

Synthesis of (12R,14S,15S,18R,19S,20R,21R,E)-12-Ethyl-14,20-dimethoxy-15,19,21,24-tetramethyl-10,25-dioxo-1,1,1-triphenyl-5,8,11-trioxa-2-thia-24-azapentacos-22-en-18-yl isobutyrate (12)

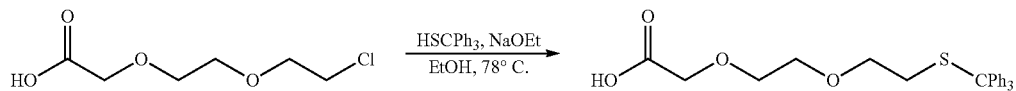

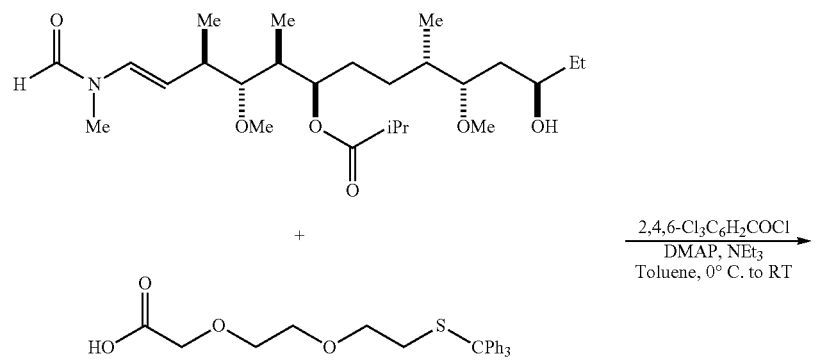

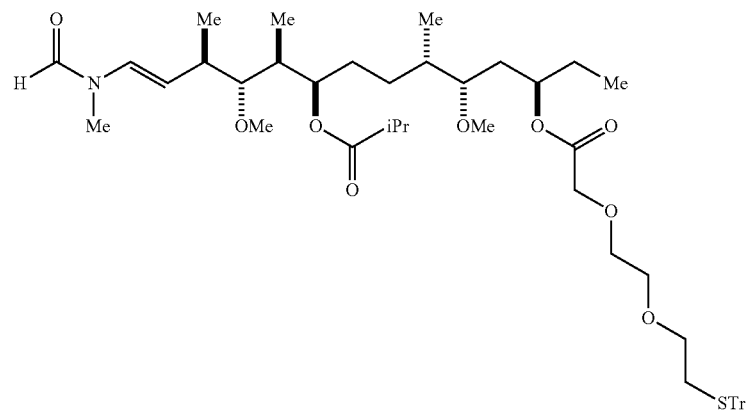

2-(2-(2-(Tritylthio)ethoxy)ethoxy)acetic acid

Triphenylmethanethiol (283 mg, 1.02 mmol, 1.1 equiv.) was added in one portion to a solution of sodium ethoxide (8.46 mL, 1.86 mmol; 0.22 M solution in ethanol, 2.0 equiv.) at 0° C. The mixture was stirred at ambient temperature for 30 minutes and then 2-(2-(2-chloroethoxy)ethoxy)acetic acid (Kato, H. et. al *Eur. J. Org. Chem.* (2007) 2659) (170.0 mg, 0.931 mmol, 1.0 equiv.) was added via syringe. The mixture was refluxed overnight and then cooled to ambient temperature, and quenched with water (17 mL). The solution was acidified with 2 N HCl solution and partitioned with dichloromethane. The organic phases were combined, dried (anhyd. MgSO$_4$) and filtered. The reaction mixture was concentrated in vacuo and the crude product was purified via flash chromatography (SiO2, gradient elution with 95:5:0.5 to 90:10:0.5 dichloromethane/methanol/acetic acid) to furnish the title compound (330 mg, 84%) as light yellow needles; mp (ethyl acetate/hexanes)=108-110° C.

(12R,14S,15S,18R,19S,20R,21R,E)-12-Ethyl-14,20-dimethoxy-15,19,21,24-tetramethyl-10,25-dioxo-1,1,1-triphenyl-5,8,11-trioxa-2-thia-24-azapentacos-22-en-18-yl isobutyrate (12)

The title compound was prepared using the conditions described in the General Procedure B for Yamaguchi Esterification from Example 28 wherein the reactants were (3R,4R,5S,6R,9S,10S,12R,E)-12-hydroxy-4,10-dimethoxy-3,5,9-trimethyl-1-(N-methylformamido)tetradec-1-en-6-yl isobutyrate and 2-(2-(2-(tritylthio)ethoxy)ethoxy)acetic acid. 17.5 mg, 77%

Synthesized actin-targeting agents have been shown to be equipotent with natural products in several in vitro and in vivo assays. Next steps include attaching them to tumor specific antibodies.

Example 30

Actin Polymerization Inhibition Concentration Dependence

Actin polymerization reactions were performed as follows: 63 µL of 9 µM (final concentration) 30% pyrene actin in G-buffer was mixed with 1.4 µL of 0-1000 µM solutions of toxin in DMSO in a fluorimeter cuvette at 25° C. After 50 s incubation, actin polymerization reactions were initiated by the addition of 7 µL of actin polymerization buffer (APB) (100 mM Tris-HCl pH 7.5, 500 mM KCl, 20 mM MgCl$_2$ and 10 mM ATP) to pyrene actin—toxin mixture (Allingham et al., 2005, Proc. Nat. Acad. Sci., 102(4): 14527-14532). Fluorescence emission at 406 nm was measured using a Lifetime Fluorimeter (ISS, Inc.) with an excitation wavelength of 365 nm, for a period of time 600 s.

Rate of polymerization was calculated as an increase in fluorescent intensity between time points 250 s and 300 s and divided on 50 s. Polymerization rate of actin in absence of toxin was set as 100%. The rate of polymerization in present of a toxin was expressed as a percentage relative to no toxin value and was plotted versus concentration of a toxin. From this plot IC$_{50}$ value was deduced as concentration of toxin at which 50% rate of polymerization was observed. See FIGS. 1A-D for plots from this study.

Example 31

Effect of Analogs on the Actin Cytoskeleton

To visualize effects of analogs on cellular F-actin dynamics, several cancer cell lines were transduced with a lentivirus expressing a green fluorescent protein (GFP) fusion with LifeAct, a 17 amino-acid protein containing the actin-binding domain of a yeast protein. To produce this lentivirus, 500,000 HEK293T cells were seeded on a 6-well plate coated with 0.01 mg/ml of poly-lysine solution. 24 hours later viral packing plasmids Pax2 (1 ug) and MD2G (0.5 ug) were mixed in serum free media with 1 ug of pLenti.PGK.LifeAct-GFP.W (Addgene Catalogue No. 51010), and 10 uL of Xtreme-Gene (Roche, Germany) were then added to the master mix. The mix was vortexed and incubated at room temperature for 15 minutes before being added in a drop-wise manner to HEK293T cells. After 24 hours, HCC1954, SKBR3 or SKOV3 cells were seeded in a 6-well plate and incubated at 37° C. for 24 hours. The virus-containing media from the HEK293T cells media was collected and filtered (0.45 µm). HCC1954, SKBR3 or SKOV3 cells were incubated with 0.5 mL virus-containing media, and incubated at 37° C. for 2-3 days. Efficiency of transduction was determined by visualizing GFP positive cells using fluorescence microscopy.

To visualize F-actin dyanimcs in live cell HCC1954, SKBR3 or SKOV3 cells expressing LifeAct-GFP were seeded on a sterilized live cell imaging chamber coated with 10 µg/ml of human fibronectin. After 24 at 37° C. the chamber was moved into the environment controlled conditions of a Quorum Wave FX-X1 Spinning Disc Confocal live cell imaging system (Quorum Technologies Inc., Guelph). After initial images were captured at time 0, media with 2 times the concentration of treatment was added and images were captured every 10 minutes following. Time lapse videos were then created using ImageJ Software (NIH).

See FIG. 2 for images from these studies.

Example 32

IncuCyte Scratch Wound Assay

Effects of analogs on cellular motility including invasion and migration were evaluated using the IncuCyte Live Cell System. 25,000 SKOV3 cells were plated on a 96-well ImageLock coated with 10 µg/ml of human fibronectin. Once the cells reached approximately 90% confluence a scratch/wound is induced using the IncuCyte Woundmaker (a 96-pin would making tool). The cells were then rinsed with sterile PBS then media, with or without treatment were added. To evaluate invasion 5% Matrigel was added. The plate was then inserted into the IncuCyte Zoom Live Cell Analysis System and imaged at 10× magnification every 2-3 hours following until wound closure or 48 hours.

The percentage of wound confluence, for migration, or would density, for invasion, was determined through the IncuCyte ZOOM Scratch Wound Analysis tool adjusted to cell line dependent processing definitions. See FIGS. 5 to 6 for images and graphical results.

Example 33

IncuCyte PI Uptake Assay of Cytotoxicity

The cytotoxicity of analogs was determined by using a PI uptake assay. HCC1954, SKBR3 or SKOV3 cells (2,000) were seeded in a 96-well plate. Treatments were prepared in 2% FBS containing media with 1 µM PI, and imaged using the IncuCyte Zoom Live Cell Analysis System equipped with a 10× objective. Phase contrast and fluorescent images were acquired every 2-3 hours for 48 hours. Several parameters are available upon analysis utilizing the IncuCyte Zoom Analysis tools including number of PI positive cells and cell confluence. See FIG. 8 for plots of SKOV3 cell analog cytotoxicity and HCC1954 cell analog cytotoxicity for specified treatments.

Example 34

Spheroid Reattachment Invasion/Migration Assay

A three-dimensional (3D) spheroid reattachment assay was performed to further evaluate analog effects on migration and invasion. A round bottom 96-well was coated with polyhydroxyehylmethacrylate (poly-hema) to create a non-adhesive conditions upon which cancer cells can form a 3D spheroid. SKOV3 cells (1,000) were seeded in each poly-hema coated well. 72 hours later this spheroid was removed by carefully pipetting it out and placing into a round bottom 96-well. To evaluate invasion the treatment included 5% Matrigel. The spheroid were spun to the bottom and center of these wells using a plate spinner at 350 for 5 minutes. These spheroids will attach to the bottom of the well to migrate or invade outward.

The percentage of migration/invasion was calculated using ImageJ (NIH) by measuring the area of migration or invasion and subtracting the intial size of the spheroid. See FIG. 7 for plots and images from this study.

Example 35

SKOV3 Tumor Study

Using a HER2+ SKOV3 subcutaneous tumor xenograft model, anti-tumor effects of MycB on tumor volume and mass were demonstrated. This study also showed the potential improvement when combined with TZ (Herceptin) on limiting tumor growth and metastasis in this model. Although MycB analogs have not been tested in this model at this time, the most potent analogs are expected to yield similar anticancer effects. The anti-tumor effects of MycB analogs are also expected to extend to other cancer types with selection of appropriate antibodies for these tumor types with novel ADC formulations.

Example 36

Growth Suppression of HER2 Cancer Cells by Select Myc B Analogs

Growth suppression of HER2 cancer cells by select Myc B analogs was studied to determine rate of growth of HER2 cancer cells (SKOV3 (ovarian) and HCC1954 (breast)) as measured using a live cell imaging system. Findings are shown in FIGS. 9A and 9B, SKOV3 Ovarian cancer and HCC1954 Breast cancer cells were incubated with DMSO (1%), Myc B (25 nM), or the indicated analogs (25 µM), or with HER2 inhibitor Lapatinib (25 µM) in DMEM supplemented with 2% FBS and PI (1 µM) using an IncuCyte Zoom Live Cell Analysis System for 48 hours. Graphs depict the percent change in confluence at 48 hours compared to time zero (significant differences from DMSO *p<0.05, p<0.01, *p<0.001). Notably, in these studies, a potent analog was seen in 4f (2534), with comparable effects of the HER2 inhibitor Lapatinib.

Example 37

Cytotoxicity Effects of Myc B and Analogs in HER2 Cancer Cells

Cytotoxicity effects of Myc B and analogs in HER2 cancer cells was studied. Specifically, SKOV3 (ovarian) and HCC1954 (breast) cells were incubated with DMSO (1%) or analog (12.5-50 µM) in DMEM supplemented with 2% FBS and PI (1 µM) using an IncuCyte Zoom Live Cell Analysis System for 48 hours. As shown in FIGS. 10A-Q, graphs depict the number of PI positive for SKOV3 cells (left) and HCC1954 cells (right) over 48 hours of treatment with DMSO or indicated analog (12.5-50 µM).

Example 38

Actin Cytoskeletal Disruption by Myc B Analogs in SKOV3 Cells Expressing Life-Act-GFP Disruption of filamentous actin (F-actin) in HER2 cancer cells was measured using live cell confocal imaging of LifeAct-GFP reporter. The LifeAct-GFP signal in DMSO control conditions indicates the localization of F-actin structures in SKOV3 cells. Treatment with Myc B (25 nM) shows a time-dependent collapse of F-actin into large aggregates near the cell periphery. Treatments with analogs 4h (also known as 2415) and 4g (also known as 2453) at 10 µM dose resulted in similar collapse of F-actin structures. Analog 4f (also known as 2534) had limited effects at early time points.

It will be understood by those skilled in the art that this description is made with reference to certain embodiments and that it is possible to make other embodiments employing the principles of the invention which fall within its spirit and scope as defined by the claims.

TABLE 1

Analogs of Mycalolide B

| Nickname | Structural Formula |
|---|---|
| 4a also referred to herein as 2295 | |

TABLE 1-continued

Analogs of Mycalolide B

| Nickname | Structural Formula |
|---|---|
| 4b also referred to herein as 2222 | (structure) |
| 4c also referred to herein as 2358 | (structure) |
| 4d also referred to herein as 2298 | (structure) |
| 4e also referred to herein as 2319 | (structure) |
| 4f also referred to herein as 2534 | (structure) |
| 4g also referred to herein as 2453 | (structure) |
| 4h also referred to herein as 2415 | (structure) |

TABLE 1-continued

Analogs of Mycalolide B

| Nickname | Structural Formula |
| --- | --- |
| 11 | |
| 12 | |
| MA-02-058 | |
| MA-02-047 | |
| MA-02-044 | |

TABLE 1-continued

Analogs of Mycalolide B

| Nickname | Structural Formula |
|---|---|
| MA-02-046 | 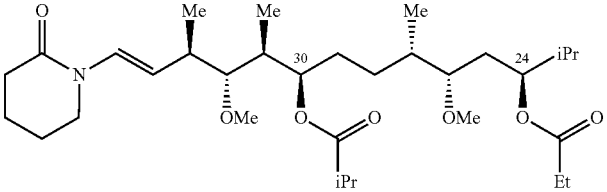 [SMILES: CCC(=O)O[C@@H](C[C@H](OC)[C@@H](C)CC[C@@H](OC(=O)C(C)C)[C@H](C)[C@H](OC)[C@H](C)/C=C/N1CCCCC1=O)C(C)C] |

TABLE 2

Structure and Characterization Data

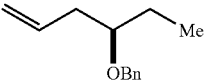

Color and State: Clear oil.
Chiral HPLC analysis: 25 cm × 4.6 mm Chiralcel OJ column, 99:1 hexane-isopropanol at 0.3 ml/min. flow rate, 210 nm, 25° C.; $t_R$(minor) 17.7 min., $t_R$(major) 19.4 min., 94% ee.
$^1$H NMR (400 MHz, CDCl$_3$) δ 7.37-7.32 (m, 4H), 7.29-7.26 (m, 1H), 5.87 (ddt, J = 17.2, 10.1, 7.1 Hz, 1H), 5.10 (d, J = 18.1 Hz, 1H), 5.06 (d, J = 10.2 Hz, 1H), 4.57 (d, A of AB, $J_{AB}$ = 11.6 Hz), 4.51 (d, B of AB, $J_{AB}$ = 11.6 Hz), 3.39 (app. quintet, J = 5.8 Hz, 1H), 2.37 (dd, J = 14.1, 5.9 Hz, 1H), 2.30 (dd, J = 13.8, 6.5 Hz, 1H), 1.58 (app. quintet, J = 7.0 Hz, 2H), 0.94 (t, J = 7.4 Hz, 3H).
IR (neat) 3067 (w), 3029 (w), 2964 (w), 2930 (w), 2861 (w), 1639 (w), 1495 (w), 1092 (s), 1064 (s), 910 (s), 732 (s), 695 (vs) cm$^{-1}$.

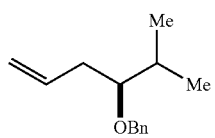

Color and State: Light yellow oil.
Chiral HPLC analysis: 25 cm × 4.6 mm Chiralcel OJ column 99.5:0.5 hexane-isopropanol at 1.0 mL/min. flow rate, 210 nm, 25° C; $t_R$(minor) 5.1 min., $t_R$(major) 5.3 min., 99% ee.
$^1$H NMR (400 MHz, CDCl$_3$) δ 7.37-7.31 (m, 4H), 7.29-7.25 (m, 1H), 5.89 (ddt, J = 17.2, 10.1, 7.0 Hz, 1H), 5.10 (ddd, J = 17.2, 3.5, 1.6 Hz, 1H), 5.05 (app. dt, J = 10.1, 1.0 Hz, 1H), 4.58 (d, A of AB, $J_{AB}$ = 11.6 Hz), 4.49 (d, B of AB, $J_{AB}$ = 11.5 Hz), 3.20 (app. q, J = 5.7 Hz, 1H), 2.32 (app. qt, J = 6.7, 1.4 Hz, 2H), 1.88 (d of septets, J = 12.4, 6.8 Hz, 1H), 0.95 (d, J = 6.8 Hz, 3H), 0.93 (d, J = 6.8 Hz, 3H).
IR (neat) 3066 (w), 3029 (w), 2958 (m), 2932 (w), 2892 (w), 2869 (w), 1639 (w), 1495 (w), 1091 (s), 1066 (s), 909 (m), 732 (s), 696 (vs) cm$^{-1}$.

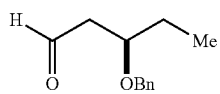

Color and State: Clear oil.
$[α]_D^{20}$ −26.3 (c = 0.55, CHCl$_3$)
Literature result for comparison $[α]_D^{15}$ (S enantiomer) +29.5 (c = 0.54, CHCl$_3$), S. Motodate, et al., Chem, Asian J. 2010, 5, 2221-2230.
IR (neat) 3030 (w), 2965 (w), 2932 (w), 2875 (w), 2726 (w), 1721 (s), 1454 (m), 1088 (s), 1060 (s), 735 (s), 696 (vs) cm$^{-1}$.

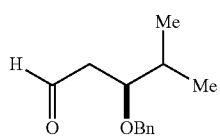

Color and State: Clear oil.
$[α]_D^{22}$ −38.4 (c = 0.96, CHCl$_3$)
{see S.-J. Jeon, et al., Org. Lett 2005, 7, 1729 for literature reference with $[α]_D^{22}$ −34.5 (c = 1.0, CHCl$_3$)}.
$^1$H NMR (400 MHz, CDCl$_3$) δ 9.81 (dd, J = 2.5, 1.9 Hz, 1H), 7.36-7.27 (m, 5H), 4.58 (d, A of AB, $J_{AB}$ = 11.4 Hz), 4.52 (d, B of AB, $J_{AB}$ = 11.4 Hz), 3.79 (ddd, J = 8.4, 4.8, 3.8 Hz, 1H), 2.64 (ddd, J = 16.4, 8.2, 2.6 Hz, 1H), 2.50 (ddd, J = 16.4, 3.8, 1.8 Hz, 1H), 2.05 (septet of d, J = 6.8, 5.1 Hz, 1H), 0.95 (d, J = 6.8 Hz, 3H), 0.95 (d, J = 6.8 Hz, 3H).
IR (neat) 3063 (w), 3030 (w), 2960 (m), 2933 (w), 2872 (w), 2724 (w), 1721 (s), 1454 (w), 1088 (s), 1063 (s), 735 (s), 696 (vs) cm$^{-1}$.

TABLE 2-continued

Structure and Characterization Data

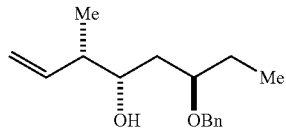 [SMILES: C=C[C@H](C)[C@@H](O)C[C@@H](CC)OCc1ccccc1]

Color and State: Clear oil.
[α]$_D^{24}$ −44.9 (c = 1.00, CHCl$_3$).
$^1$H NMR (400 MHz, CDCl$_3$) δ 7.35-7.31 (m, 4H), 7.30-7.26 (m, 1H), 5.76 (ddd, J = 16.9, 10.8, 7.7 Hz, 1H), 5.06 (dd, J = 8.0, 2.1, 0.9 Hz, 1H), 5.03 (d, J = 0.5 Hz, 1H), 4.59 (d, A of AB, J$_{AB}$ = 11.5 Hz), 4.51 (d, B of AB, J$_{AB}$ = 11.5 Hz), 3.75 (app. d of quintets, J = 6.4, 3.9 Hz, 1H), 3.66 (app. quintet of d, J = 5.5, 0.9 Hz, 1H), 2.70 (d, J = 4.0 Hz, 1H), 2.23 (app. sextet, J = 6.8 Hz, 1H), 1.73 (dqd, J = 13.5, 7.6, 5.9 Hz, 1H), 1.66 (dd, J = 4.1, 1.6 Hz, 1H), 1.64 (app. t, J = 3.8 Hz, 1H), 1.62-1.53 (m, 1H), 1.04 (d, J = 6.8 Hz, 3H), 0.91 (t, J = 7.5 Hz, 3H).
$^{13}$C NMR (100 MHz, CDCl$_3$) δ 141.23 (o), 138.60 (e), 128.56 (o), 128.00 (o), 127.82 (o), 115.06 (e), 78.50 (o), 71.67 (o), 71.33 (e), 44.16 (o), 36.52 (e), 26.16 (e), 15.39 (o), 9.87 (o).
IR (neat) 3451 (w, br.), 3065 (w), 3030 (w), 2963 (m), 2929 (w), 2874 (w), 1638 (w), 1495 (w), 1454 (m), 1062 (s), 1026 (s), 910 (s), 733 (s), 696 (vs) cm$^{-1}$.
HRMS (ESI, [M + Na]$^+$) calcd for C$_{16}$H$_{25}$O$_2$Na 249.1849, found 249.1838.

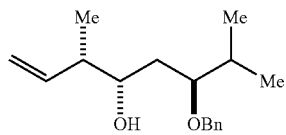 [SMILES: C=C[C@H](C)[C@@H](O)C[C@H](OCc1ccccc1)C(C)C]

Color and State: Clear oil.
[α]$_D^{23}$ −38.2 (c = 1.03, CHCl$_3$).
$^1$H NMR (400 MHz, CDCl$_3$) δ 7.38-7.32 (m, 4H), 7.31-7.26 (m, 1H), 5.77 (ddd, J = 16.9, 10.7, 7.7 Hz, 1H), 5.08 (ddd, J = 8.0, 1.9, 1.0, 1H), 5.04 (d, J = 0.6 Hz, 1H), 4.59 (d, A of AB, J$_{AB}$ = 11.4 Hz), 4.56 (d, B of AB, J$_{AB}$ = 11.4 Hz), 3.73 (dddd, J = 9.8, 6.7, 4.1, 2.4 Hz, 1H), 3.49 (ddd, J = 8.1, 6.0, 2.5 Hz, 1H), 2.60 (d, J = 4.3 Hz, 1H), 2.25 (app. sextet, J = 6.8 Hz, 1H), 2.04 (app. octet, J = 6.7 Hz, 1H), 1.67 (ddd, J = 14.7, 7.9, 2.3 Hz, 1H), 1.57 (ddd, J = 14.6, 9.5, 3.0 Hz, 1H), 1.06 (d, J = 6.8 Hz, 3H), 0.97 (d, J = 6.8 Hz, 3H), 0.91 (d, J = 6.8 Hz, 3H).
$^{13}$C NMR (100 MHz, CDCl$_3$) δ 141.17 (o), 138.63 (e), 128.49 (o), 128.02 (o), 127.75 (o), 115.06 (e), 82.18 (o), 72.09 (e), 71.79 (o), 44.22 (o), 33.26 (e), 30.48 (o), 19.17 (o), 17.70 (o), 15.33 (o).
IR (neat) 3457 (w, br.), 3067 (w), 3030 (w), 2958 (m), 2929 (m), 2872 (m), 1638 (w), 1495 (w), 1454 (m), 1063 (vs), 1027 (s), 911 (s), 733 (s), 696 (vs) cm$^{-1}$.
HRMS (ESI, [M + H]$^+$) calcd for C$_{17}$H$_{27}$O$_2$ 263.2006, found 263.2001.

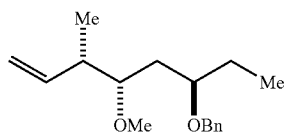

Color and State: Clear oil.
[α]$_D^{20}$ −45.0 (c = 1.01, CHCl$_3$).
$^1$H NMR (400 MHz, CDCl$_3$) δ 7.38-7.32 (m, 4H), 7.29-7.26 (m, 1H), 5.88-5.80 (m, 1H), 5.05 (s, 1H), 5.01 (dt, J = 5.7, 1.5 Hz, 1H), 4.60 (d, A of AB, J$_{AB}$ = 11.5 Hz), 4.55 (d, B of AB, J$_{AB}$ = 11.5 Hz), 3.58 (dddd, J = 8.3, 6.4, 5.2, 3.0 Hz, 1H), 3.33 (ddd, J = 9.9, 4.3, 2.9 Hz, 1H), 3.30 (s, 3H), 2.56-2.48 (m, 1H), 1.66-1.54 (m, 3H), 1.44 (ddd, J = 14.5, 10.1, 2.8 Hz, 1H), 1.00 (d, J = 6.9 Hz, 3H), 0.92 (t, J = 7.5 Hz, 3H).
$^{13}$C NMR (100 MHz, CDCl$_3$) δ 140.56 (o), 139.28 (e), 128.46 (o), 127.96 (o), 127.56 (o), 114.64 (e), 81.58 (o), 76.97 (o), 71.07 (e), 57.68 (o), 39.88 (o), 36.11 (e), 26.86 (e), 15.36 (o), 9.36 (o).
IR (neat) 3066 (w), 3029 (w), 2964 (m), 2926 (m), 2875 (m), 2817 (w), 1639 (w), 1495 (w), 1454 (m), 1091 (vs), 1065 (s), 910 (s), 733 (s), 696 (s) cm$^{-1}$.
HRMS (ESI, [M + H]$^+$) calcd for C$_{17}$H$_{27}$O$_2$ 263.2001, found 263.1995.

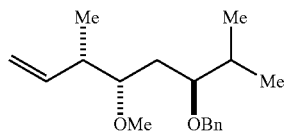 [SMILES: C=C[C@H](C)[C@H](C[C@H](OCc1ccccc1)C(C)C)OC]

Color and State: Clear oil.
[α]$_D^{23}$ −74.7 (c = 0.48, CHCl$_3$).
$^1$H NMR (400 MHz, CDCl$_3$) δ 7.38-7.32 (m, 4H), 7.29-7.25 (m, 1H), 5.88-5.80 (m, 1H), 5.05 (s, 1H), 5.01 (app. dt, J = 5.5, 1.4, 1H), 4.62 (d, A of AB, J$_{AB}$ = 11.5 Hz), 4.45 (d, B of AB, J$_{AB}$ = 11.5 Hz), 3.34-3.28 (m, 1H), 3.30 (s, 3H), 3.45 (ddd, J = 10.0, 4.4, 2.5 Hz, 1H), 2.58-2.49 (m, 1H), 2.00 (septet of d, J = 6.9, 4.5 Hz, 1H), 1.49 (ddd, J = 14.4, 10.1, 2.5 Hz, 1H), 1.39 (ddd, J = 14.4, 10.1, 2.5 Hz, 1H), 1.00 (d, J = 7.0 Hz, 3H), 0.92 (d, J = 6.9 Hz, 3H), 0.91 (d, J = 6.8 Hz, 3H).
$^{13}$C NMR (100 MHz, CDCl$_3$) δ 140.49 (o), 139.38 (e), 128.42 (o), 127.85 (o), 127.50 (o), 114.65 (e), 81.57 (o), 80.63 (o), 71.97 (e), 57.44 (o), 39.72 (o), 32.12 (e), 30.72 (o), 18.66 (o), 17.30 (o), 15.39 (o).
IR (neat) 3066 (w), 3029 (w), 2959 (m), 2930 (m), 2873 (m), 2822 (w), 1639 (w), 1495 (w), 1454 (m), 1092 (vs), 1066 (s), 910 (m), 733 (s), 696 (s) cm$^{-1}$.
HRMS (ESI, [M + H]$^+$) calcd for C$_{18}$H$_{29}$O$_2$ 277.2162, found 277.2150.

TABLE 2-continued

Structure and Characterization Data

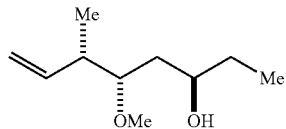

Color and State: Clear oil. $[\alpha]_D^{20}$ −103.7 (c = 0.48, CHCl₃).
¹H NMR (400 MHz, CDCl₃) δ 5.76 (ddd, J = 17.1, 10.6, 7.5 Hz, 1H), 5.06 (ddd, J = 8.1, 1.7, 1.1 Hz, 1H), 5.02 (d, J = 1.0 Hz, 1H), 3.82-3.76 (m, 1H), 3.42 (s, 3H), 3.32 (td, J = 6.6, 4.3 Hz, 1H), 2.56 (app. sextet, J = 6.9 Hz, 1H), 2.56 (d, J = 4.4 Hz, 1H), 1.56 (app. quintet, J = 3.6 Hz, 2H), 1.54-1.38 (m, 2H), 1.04 (d, J = 6.8 Hz, 3H), 0.92 (t, J = 7.4 Hz, 3H).
¹³C NMR (100 MHz, CDCl₃) δ 140.27 (o), 115.07 (e), 83.06 (o), 70.39 (o), 57.83 (o), 40.15 (o), 36.25 (e), 30.76 (e), 16.23 (o), 10.19 (o).
IR (neat) 3425 (w, br.), 3078 (w), 2963 (m), 2929 (m), 2877 (m), 2826 (w), 1640 (w), 1457 (m), 1085 (vs), 984 (m), 910 (s) cm⁻¹.
HRMS (ESI, [M + H]⁺) calcd for C₁₀H₂₁O₂ 173.1536, found 173.1533.

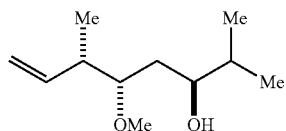

Color and State: Clear oil.
$[\alpha]_D^{24}$ −37.5 (c = 0.49, CHCl₃).
¹H NMR (400 MHz, CDCl₃) δ 5.75 (ddd, J = 17.3, 10.3, 7.6 Hz, 1H), 5.06 (ddd, J = 10.0, 1.6, 1.1 Hz, H), 5.02 (app. dt, J = 2.8, 1.6 Hz, 1H), 3.61 (ddt, J = 8.0, 5.7, 4.0 Hz, 1H), 3.42 (s, 3H), 3.32 (td, J = 6.7, 4.0 Hz, 1H), 2.56 (app. sextet, J = 6.9 Hz, 1H), 2.53 (d, J = 4.3 Hz, 1H), 1.63 (septet, J = 6.7 Hz, 1H), 1.61-1.50 (m, 2H), 1.05 (d, J = 6.8 Hz, 3H), 0.93 (d, J = 6.8 Hz, 3H), 0.88 (d, J = 6.8 Hz, 3H).
¹³C NMR (100 MHz, CDCl₃) δ 140.36 (o), 115.07 (e), 83.27 (o), 73.65 (o), 57.95 (o), 40.32 (o), 34.17 (o), 33.60 (e), 18.71 (o), 18.04 (o), 16.34 (o).
IR (neat) 3455 (w, br.), 3077 (w), 2958 (m), 2932 (m), 2875 (m), 2826 (w), 1640 (w), 1460 (w), 1084 (vs), 997 (s) cm⁻¹.
HRMS (ESI, [M + H]⁺) calcd for C₁₁H₂₃O₂ 187.1693, found 187.1683.

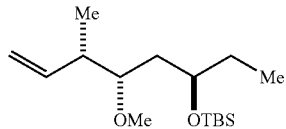 [SMILES: C=C[C@H](C)[C@H](C[C@@H](CC)O[Si](C)(C)C(C)(C)C)OC]

$[\alpha]_D^{20}$ −63.1 (c = 0.52, CHCl₃).
¹H NMR (400 MHz, CDCl₃) δ 5.84 (ddd, J = 16.8, 10.9, 6.9 Hz, 1H), 5.05 (s, 1H), 5.02 (dt, J = 8.3, 1.6 Hz, 1H), 3.80 (dt, J = 12.4, 5.1 Hz, 1H), 3.37 (s, 3H), 3.29 (dt, J = 8.1, 5.4, 1H), 2.58 (dq, J = 12.6, 6.1 Hz, 1H), 0.99 (d, J = 7.0 Hz, 3H), 0.90 (s, 9H), 0.85 (t, J = 7.5 Hz, 3H), 1.50 (dd, J = 7.7, 5.5 Hz, 1H), 1.46 (dd, J = 7.4, 5.6 Hz, 1H), 1.42 (dq, J = 7.7, 3.7 Hz, 2H), 0.07 (s, 3H), 0.06 (s, 3H).
¹³C NMR (100 MHz, CDCl₃) δ 140.32 (o), 114.64 (e), 81.59 (o), 70.31 (o), 56.87 (o), 38.83 (o), 37.63 (e), 30.96 (e), 26.13 (o), 18.27 (e), 15.34 (o), 9.03 (o), −3.77 (o), −4.43 (o).
IR (neat) 2958 (m), 2929 (m), 2884 (w), 2858 (w), 1641 (w), 1382 (w), 1364 (w), 1095 (s), 1059 (m), 1006 (m), 834 (s), 772 (vs) cm⁻¹.
HRMS (ESI, [M + Na]⁺) calcd for C₁₆H₃₄O₂NaSi 309.2220, found 309.2220.

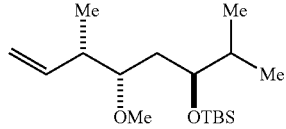 [SMILES: C=C[C@H](C)[C@H](C[C@H](O[Si](C)(C)C(C)(C)C)C(C)C)OC]

$[\alpha]_D^{20}$ −37.5 (c = 0.49, CHCl₃).
¹H NMR (400 MHz, CDCl₃) δ 5.88-5.79 (m, 1H), 5.05 (d, J = 1.2 Hz, 1H), 5.02 (app. dt, J = 7.6, 1.5 Hz, 1H), 3.72 (ddt, J = 8.0, 6.8, 3.3 Hz, 1H), 3.36 (s, 3H), 3.26 (dt, J = 7.6, 4.5 Hz, 1H), 2.63-2.55 (m, 1H), 1.36-1.30 (m, 2H), 0.98 (d, J = 7.0 Hz, 3H), 0.90 (s, 9H), 0.85 (d, J = 6.9 Hz, 3H), 0.82 (d, J = 7.0 Hz, 3H), 0.06 (s, 3H), 0.05 (s, 3H).
¹³C NMR (100 MHz, CDCl₃) δ 140.37 (o), 114.63 (e), 81.60 (o), 73.5 (o), 56.80 (o), 38.96 (o), 34.04 (o), 33.07 (e), 26.16 (o), 18.33 (e), 18.11 (o), 16.53 (o), 15.39 (o), −3.82 (o), −4.31 (o).
IR (neat) 2929 (m), 2930 (m), 2885 (w), 2858 (w), 1641 (w), 1386 (w), 1371 (w), 1096 (m), 1059 (s), 912 (m), 834 (s), 772 (vs) cm⁻¹.
HRMS (ESI, [M + H]⁺) calcd for C₁₇H₃₇O₂Si 301.2557, found 301.2556.

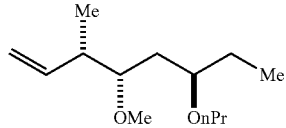

TABLE 2-continued

Structure and Characterization Data

Color and State: Clear oil.
$[\alpha]_D^{20}$ −59.1 (c = 0.99, CHCl$_3$).
$^1$H NMR (400 MHz, CDCl$_3$) δ 5.89-5.80 (m, 1H), 5.05 (dt, J = 3.4, 1.9 Hz, 1H), 5.01 (dt, J = 3.2, 1.7 Hz, 1H), 3.50 (dt, J = 9.0, 6.6 Hz, 1H), 3.42-3.36 (m, 1H), 3.39 (s, 3H), 3.33 (ddd, J = 9.9, 4.6, 2.7, 1H), 3.28 (dt, J = 9.0, 6.8 Hz, 1H), 2.51 (app. sextet of d, J = 6.8, 1.1 Hz, 1H), 1.65-1.54 (m, 2H), 1.53-1.44 (m, 3H), 1.39 (ddd, J = 14.4, 10.1, 2.9 Hz, 1H), 1.01 (d, J = 6.9 Hz, 3H), 0.94 (t, J = 7.4 Hz, 3H), 0.88 (t, J = 7.5 Hz, 3H).
$^{13}$C NMR (100 MHz, CDCl$_3$) δ 140.67 (o), 114.57 (e), 81.63 (o), 77.11 (o), 70.88 (e), 57.74 (o), 39.98 (o), 36.22 (e), 27.07 (e), 23.63 (e), 15.35 (o), 11.03 (o), 9.46 (o).
IR (neat) 3078 (w), 2962 (m), 2927 (m), 2874 (m), 2817 (w), 1639 (w), 1375 (w), 1089 (vs), 1007 (m), 909 (m) cm$^{-1}$.
HRMS (ESI, [M + H]$^+$) calcd for C$_{13}$H$_{27}$O$_2$ 215.2006, found 215.1999.

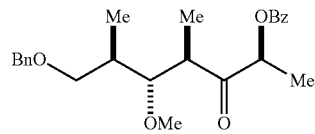

$[\alpha]_D^{22}$ −5.2 (c = 1.02, CHCl$_3$).
$^1$H NMR (400 MHz, CDCl$_3$) δ 8.10-8.07 (m, 2H), 7.57 (tt, J = 7.5, 1.5 Hz, 1H), 7.44 (t, J = 7.7 Hz, 2H), 7.36-7.26 (m, 5H), 5.37 (q, J = 7.0 Hz, 1H), 4.47 (s, 2H), 3.60 (dd, J = 9.2, 6.4 Hz, 1H), 3.45 (dd, J = 9.8, 2.2 Hz, 1H), 3.32-3.26 (m, 1H), 3.28 (s, 3H), 3.22 (dq, J = 9.6, 7.3 Hz, 1H), 2.11 (app. sextet of d, J = 6.9, 2.3 Hz, 1H), 1.51 (d, J = 7.0 Hz, 3H), 1.13 (d, J = 7.0 Hz, 3H), 1.06 (d, J = 7.1 Hz, 3H).
$^{13}$C NMR (100 MHz, CDCl$_3$) δ 210.32 (e), 165.86 (e), 138.67 (e), 133.25 (o), 129.88 (o), 129.81 (e), 128.47 (o), 128.45 (o), 127.58 (o), 127.52 (o), 86.11 (o), 75.19 (o), 73.17 (e), 71.62 (e), 61.27 (o), 45.62 (o), 35.48 (o), 16.09 (o), 15.18 (o), 14.43 (o).
IR (neat) 3062 (w), 3029 (w), 2967 (w), 2934 (w), 2876 (w), 1716 (s), 1601 (w), 1451 (m), 1264 (s), 1112 (s), 1084 (s), 1069 (s), 710 (vs), 696 (s) cm$^{-1}$.

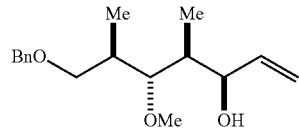 [SMILES: C=C[C@@H](O)[C@H](C)[C@H](OC)[C@H](C)COCc1ccccc1]

$[\alpha]_D^{20}$ +25.7 (c = 1.03, CHCl$_3$).
$^1$H NMR (400 MHz, CDCl$_3$) δ 7.37-7.31 (m, 4H), 7.30-7.27 (m, 1H), 5.82 (ddd, J = 17.2, 10.6, 4.8 Hz, 1H), 5.28 (dt, J = 17.2, 1.7 Hz, 1H), 5.14 (dt, J = 10.6, 1.7 Hz, 1H), 4.51 (s, 2H), 4.46 (app. d of quintets, J = 4.5, 2.3 Hz, 1H), 3.53 (d, J = 5.0 Hz, 1H), 3.52 (br. s, 1H), 3.46 (s, 3H), 3.23 (dd, J = 7.6, 4.3 Hz, 1H), 2.11 (app. quintet of t, J = 7.1, 4.8 Hz, 1H), 1.84 (qdd, J = 7.0, 4.7, 2.2 Hz, 1H), 1.02 (d, J = 7.0 Hz, 3H), 1.00 (d, J = 7.2 Hz, 3H).
$^{13}$C NMR (100 MHz, CDCl$_3$) δ 139.81 (o), 138.68 (e), 128.45 (o), 127.68 (o), 127.63 (o), 114.34 (e), 88.35 (o), 73.23 (e), 72.27 (e), 72.20 (o), 61.61 (o), 38.81 (o), 36.79 (o), 15.26 (o), 11.76 (o).
IR (neat) 3488 (w, br.), 3030 (w), 2969 (w), 2912 (w), 2881 (w), 2856 (w), 1739 (w), 1644 (w), 1365 (w), 1155 (w), 1084 (vs), 1029 (m), 920 (m), 735 (s), 697 (s) cm$^{-1}$.
HRMS (ESI, [M + Na]$^+$) calcd for C$_{17}$H$_{26}$O$_3$Na 301.1774, found 301.1775.

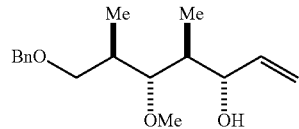 [SMILES: C=C[C@H](O)[C@H](C)[C@H](OC)[C@H](C)COCc1ccccc1]

$[\alpha]_D^{21}$ −2.9 (c = 0.47, CHCl$_3$).
$^1$H NMR (400 MHz, CDCl$_3$) δ 7.34-7.30 (m, 4H), 7.28-7.24 (m, 1H), 5.89 (ddd, J = 17.1, 10.4, 6.7 Hz, 1H), 5.26 (d, J = 17.2 Hz, 1H), 5.15 (d, J = 10.4 Hz, 1H), 4.52 (d, A of AB, J = 12.4 Hz, 1H), 4.49 (d, B of AB, J = 12.7 Hz, 1H), 4.15 (app. t, J = 6.2 Hz, 1H), 3.59 (dd, J = 9.2, 5.0 Hz, 1H), 3.47 (s, 3H), 3.42 (dd, J = 9.2, 6.8 Hz, 1H), 3.14 (dd, J = 6.3, 5.2 Hz, 1H), 3.00 (br. d, J = 2.6 Hz, 1H), 2.18 (app. quintet of t, J = 6.8, 5.1 Hz, 1H), 1.93 (app. sextet, J = 6.9 Hz, 1H), 1.09 (d, J = 7.0 Hz, 3H), 0.90 (d, J = 7.0 Hz, 3H).
$^{13}$C NMR (100 MHz, CDCl$_3$) δ 139.51 (o), 138.76 (e), 128.47 (o), 127.70 (o), 127.62 (o), 116.08 (e), 89.57 (o), 76.51 (o), 73.27 (e), 72.18 (e), 61.03 (o), 40.92 (o), 37.13 (o), 15.70 (o), 15.12 (o).
IR (neat) 3432 (w, br.), 3063 (w), 3028 (w), 2965 (w), 2924 (w), 2875 (w), 1723 (w), 1641 (w), 1364 (w), 1151 (w), 1086 (vs), 1072 (vs), 1026 (m), 920 (s), 734 (s), 697 (s) cm$^{-1}$.
HRMS (ESI, [M + Na]$^+$) calcd for C$_{17}$H$_{26}$O$_3$Na 301.1774, found 301.1769.

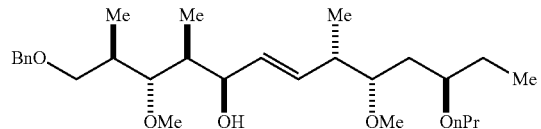

Color and State: Light green oil.
$[\alpha]_D^{25}$ −22.4 (c = 0.49, CHCl$_3$).
$^1$H NMR (400 MHz, CDCl$_3$) δ 7.36-7.31 (m, 4H), 7.29-7.25 (m, 1H), 5.69 (ddd, J = 15.6, 7.0, 1.2 Hz, 1H), 5.45 (ddd, J = 15.6, 5.5, 0.9 Hz, 1H), 4.50 (s, 2H), 4.43 (br. dd, J = 8.2, 4.5 Hz, 1H), 3.52 (d, J = 4.8 Hz, 2H), 3.48 (dd, J = 6.6, 2.5 Hz, 1H), 3.46-3.45 (m, 1H), 3.45 (s, 3H), 3.39 (dd, J = 6.2, 3.2 Hz, 1H), 3.37 (s, 3H), 3.32 (dt, J = 7.3, 2.7 Hz, 1H), 3.27 (dt, J = 6.2, 3.2 Hz, 1H), 3.22 (dd, J = 7.5, 4.4 Hz, 1H), 2.51 (app. quintet of d, J = 6.7, 3.8 Hz, 1H), 2.10 (app. quintet of t, J = 7.0, 4.8 Hz, 1H), 1.80 (qdd, J = 7.0, 4.7, 2.2 Hz, 1H), 1.57 (app. sextet, J = 7.1 Hz, 2H), 1.54-1.43 (m, 3H), 1.38 (ddd, J = 14.4, 10.0, 2.9 Hz, 1H), 1.01 (d, J = 6.9 Hz, 6H), 1.00 (d, J = 7.1 Hz, 3H), 0.93 (t, J = 7.4 Hz, 3H), 0.86 (t, J = 7.5 Hz, 3H).
$^{13}$C NMR (100 MHz, CDCl$_3$) δ 138.71 (e), 132.72 (o), 131.41 (o), 128.44 (o), 127.68 (o), 127.62 (o), 88.43 (o), 81.80 (o), 77.08 (o), 73.23 (e), 72.32 (e), 72.09 (o), 70.79 (e), 61.61 (o), 57.83 (o), 39.41 (o), 38.92 (o), 36.78 (o), 36.57 (e), 27.01 (e), 23.61 (e), 15.74 (e), 15.34 (e), 11.91 (e), 11.02 (e), 9.39 (e).
IR (neat) 3481 (w, br.), 3028 (w), 2961 (m), 2926 (m), 2874 (m), 1454 (m), 1083 (vs), 970 (s), 735 (s), 697 (s) cm$^{-1}$.
HRMS (ESI, [M + Na]$^+$) calcd for C$_{28}$H$_{48}$NaO$_5$ 487.3394, found 487.3373.

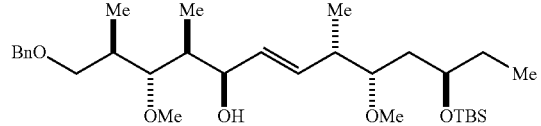 [SMILES: CC[C@H](C[C@H](OC)[C@@H](C)/C=C/[C@@H](O)[C@H](C)[C@H](OC)[C@H](C)COCc1ccccc1)O[Si](C)(C)C(C)(C)C]

Color and State: Clear oil.
[α]$_D^{20}$ −16.2 (c = 1.00, CHCl$_3$).
$^1$H NMR (400 MHz, CDCl$_3$) δ 7.37-7.31 (m, 4H), 7.30-7.27 (m, 1H), 4.51 (s, 2H), 3.90 (app. t, J = 6.6 Hz, 1H), 3.78 (dt, J = 11.9, 5.3 Hz, 1H), 3.56 (dd, J$_{AB}$ = 8.8 Hz, J$_{AX}$ = 5.2 Hz, 1H), 3.52-3.49 (m, 1H), 3.49 (s, 1H), 3.45 (s, 3H), 3.32 (s, 3H), 3.23 (dt, J = 7.8, 3.9 Hz, 1H), 3.21 (dd, J = 6.1, 2.8 Hz, 1H), 1.82-1.69 (m, 1H), 1.75 (dqt, J = 10.0, 6.7, 3.3 Hz, 1H), 2.12-2.03 (m, 1H), 1.58 (dtd, J = 13.6, 6.8, 3.5 Hz, 1H), 1.51-1.37 (m, 6H), 1.04 (d, J = 7.1 Hz, 3H), 1.01-0.93 (m, 1H), 0.97 (d, J = 6.9 Hz, 3H), 0.89 (s, 9H), 0.86 (t, J = 7.4 Hz, 3H), 0.86 (d, J = 6.8 Hz, 3H), 0.06 (s, 3H), 0.06 (s, 3H),
$^{13}$C NMR (100 MHz, CDCl$_3$) δ 138.77 (e), 128.47 (o), 127.70 (o), 127.64 (o), 89.22 (o), 81.92 (o), 73.23 (e), 72.45 (e), 71.16 (o), 70.49 (o), 61.92 (o), 57.16 (o), 37.35 (e), 37.07 (o), 36.84 (o). 34.90 (o), 32.99 (e), 30.83 (e), 27.86 (e), 26.12 (o), 18.25 (e), 15.48 (o), 15.20 (o), 11.48 (o), 9.02 (o), −3.82 (o), −4.40 (o).
IR (neat) 3508 (w, br.), 2958 (m), 2928 (m), 2881 (m), 2857 (m), 1462 (m), 1380 (m), 1252 (m), 1087 (vs), 1029 (m), 834 (s), 773 (s), 697 (s) cm$^{-1}$.
HRMS (ESI, [M + Na]$^+$) calcd for C$_{31}$H$_{58}$O$_5$NaSi 561.3946, found 561.3943.

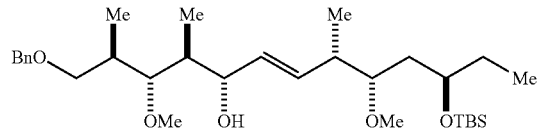 [SMILES: CC[C@H](C[C@H](OC)[C@@H](C)/C=C/[C@H](O)[C@H](C)[C@H](OC)[C@H](C)COCc1ccccc1)O[Si](C)(C)C(C)(C)C]

Color and State: Clear oil.
[α]$_D^{20}$ −21.6 (c = 0.95, CHCl$_3$).
$^1$H NMR (400 MHz, CDCl$_3$) δ 7.36-7.30 (m, 4H), 7.29-7.26 (m, 1H), 4.52 (d, A of AB, J$_{AB}$ = 12.0 Hz, 1H), 4.47 (d, B of AB, J$_{AB}$ = 12.0 Hz, 1H), 3.79 (dt, J = 12.3, 5.1 Hz, 1H), 3.61 (tt, J = 8.0, 2.6 Hz, 1H), 3.57 (dd, J = 9.2, 4.8 Hz, 1H), 3.47-3.46 (m, 1H), 3.46 (s, 3H), 3.40 (dd, J = 9.7, 2.3 Hz, 1H), 3.33 (s, 3H), 3.25 (dt, J = 7.7, 3.8 Hz, 1H), 3.09 (dd, J = 7.0, 4.5 Hz, 1H), 2.12 (app. quintet of t, J = 6.9, 4.7 Hz, 1H), 1.86-1.76 (m, 2H), 1.55-1.39 (m, 7H), 1.34-1.24 (m, 1H), 1.07 (d, J = 7.0 Hz, 3H), 0.89 (s, 9H), 0.87 (d, J = 7.0 Hz, 3H), 0.86 (d, J = 7.0 Hz, 3H), 0.85 (t, J = 7.2 Hz, 3H), 0.06 (s, 3H), 0.06 (s, 3H).
$^{13}$C NMR (100 MHz, CDCl$_3$) δ 138.82 (e), 128.47 (o), 127.70 (o), 127.61 (o), 90.04 (o), 82.13 (o), 74.55 (o), 73.28 (e), 72.26 (e), 70.58 (o), 61.08 (o), 57.07 (o), 41.39 (o), 37.43 (o), 37.31 (e), 34.76 (o), 32.54 (e), 30.92 (e), 27.18 (e), 26.14 (o), 18.27 (e), 15.76 (o), 15.69 (o), 15.23 (o), 9.01 (o), −3.80 (o), −4.39 (o).
IR (neat) 3463 (w, br.), 2958 (m), 2930 (m), 2881 (m), 2858 (m), 1459 (m), 1379 (m), 1252 (m), 1090 (vs), 1073 (vs), 1029 (m), 773 (s), 697 (s) cm$^{-1}$.
HRMS (ESI, [M + H]$^+$) calcd for C$_{31}$H$_{59}$O$_5$Si 539.4126, found 539.4116.

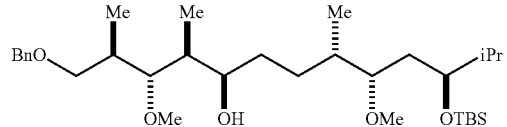 [SMILES: CO[C@@H]([C@@H](C)[C@H](O)CC[C@H](C)[C@H](C[C@H](O[Si](C)(C)C(C)(C)C)C(C)C)OC)[C@H](C)COCc1ccccc1]

Color and State: Clear oil.
[α]$_D^{22}$ −6.9 (c = 0.18, CHCl$_3$).
$^1$H NMR (400 MHz, CDCl$_3$) δ 7.37-7.31 (m, 4H), 7.30-7.28 (m, 1H), 4.51 (s, 3H), 3.90 (app. t, J = 6.7 Hz, 1H), 3.68 (dt, J = 8.3, 3.5 Hz, 1H), 3.56 (dd, J = 8.8, 5.3 Hz, 1H), 3.50 (dd, J = 8.9, 3.5 Hz, 1H), 3.49 (s, 3H), 3.45 (s, 3H), 3.32 (s, 3H), 3.22-3.19 (m, 1H), 3.21 (dd, J = 8.6, 3.2 Hz, 1H), 2.07 (app. quintet of dd, J = 7.0, 5.2, 3.5 Hz, 1H), 1.82-1.70 (m, 2H), 1.76 (dqt, J = 10.7, 7.1, 3.6 Hz, 1H), 1.62-1.54 (m, 1H), 1.47-1.40 (m, 1H), 1.44 (septet, J = 6.5 Hz, 1H), 1.39-1.19 (m, 3H), 1.05 (d, J = 7.1 Hz, 3H), 1.01-0.93 (m, 1H), 0.97 (d, J = 7.0 Hz, 3H), 0.89 (s, 9H), 0.86 (d, J = 6.9 Hz, 3H), 0.85 (d, J = 6.9 Hz, 3H), 0.83 (d, J = 7.0 Hz, 3H), 0.06 (s, 3H), 0.05 (s, 3H).
$^{13}$C NMR (100 MHz, CDCl$_3$) δ 138.70 (e), 128.42 (o), 127.65 (o), 127.59 (o), 89.13 (o), 81.83 (o), 73.59 (o), 73.17 (e), 72.37 (e), 71.09 (o), 61.87 (o), 57.06 (o), 37.04 (o), 36.78 (o), 34.90 (o), 33.73 (o), 32.92 (e), 32.87 (e), 27.83 (e), 26.10 (o), 18.26 (e), 17.74 (o), 16.86 (o), 15.43 (o), 15.15 (o), 11.45 (o), −3.92 (o), −4.29 (o).
IR (neat) 3500 (w, br.), 2956 (m), 2929 (m), 2879 (m), 2856 (m), 1458 (m), 1381 (w), 1251 (m), 1079 (vs), 1005 (m), 833 (s), 772 (s), 697 (s) cm$^{-1}$.
HRMS (ESI, [M + H]$^+$) calcd for C$_{32}$H$_{61}$O$_5$Si 553.4283, found 553.42554.

TABLE 2-continued

Structure and Characterization Data

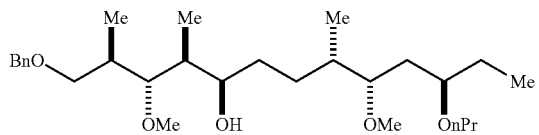

Color and State: Clear oil.
$^1$H NMR (400 MHz, CDCl$_3$) δ 7.36-7.31 (m, 4H), 7.29-7.25 (m, 1H), 4.50 (s, 2H), 3.90 (app. t, J = 6.6 Hz, 1H), 3.56 (dd, J = 8.8, 5.3 Hz, 1H), 3.51 (dd, J = 6.1, 3.3 Hz, 1H), 3.51-3.47 (br. m, 1H), 3.48 (dd, J = 6.7, 2.7 Hz, 1H), 3.45 (s, 3H), 3.39-3.33 (m, 1H), 3.35 (s, 3H), 3.31 (m, 1H), 3.28 (dd, J = 6.9, 2.3 Hz, 1H), 3.21 (dd, J = 8.8 Hz, 1H), 2.07 (app. quintet of dd, J = 6.9, 5.2, 3.3 Hz, 1H), 1.77-1.67 (m, 1H), 1.72 (dqt, J = 10.3, 6.8, 4.0 Hz, 1H), 1.64-1.39 (m, 9H), 1.35-1.17 (m, 1H), 1.04 (d, J = 7.1 Hz, 3H), 0.97 (d, J = 7.0 Hz, 3H), 0.93 (t, J = 7.5 Hz, 3H), 0.88 (t, J = 6.9 Hz, 3H), 0.88 (d, J = 6.6 Hz, 3H).
$^{13}$C NMR (100 MHz, CDCl$_3$) δ 138.74 (e), 128.45 (o), 127.68 (o), 127.62 (o), 89.20 (o), 82.02 (o), 77.38 (o), 73.21 (e), 72.43 (e), 71.14 (o), 70.82 (e), 61.88 (o), 58.00 (o), 37.04 (o), 36.82 (o), 35.88 (e), 35.83 (o), 32.95 (e), 28.38 (e), 27.07 (e), 23.61 (e), 15.31 (o), 15.17 (o), 11.47 (o), 11.03 (o), 9.44 (o).

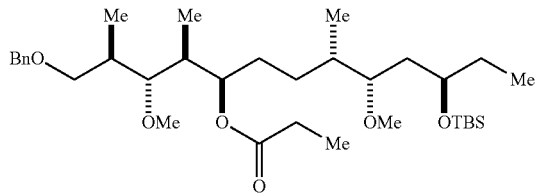 [SMILES: CCC(=O)O[C@H](CC[C@H](C)[C@H](C[C@@H](CC)O[Si](C)(C)C(C)(C)C)OC)[C@H](C)[C@H](OC)[C@H](C)COCc1ccccc1]

Color and State: Clear oil.
$[α]_D^{20}$ −23.3 (c = 0.49, CHCl$_3$).
$^1$H NMR (400 MHz, CDCl$_3$) δ 7.36-7.30 (m, 4H), 7.28-7.24 (m, 1H), 5.18 (td, J = 7.0, 1.8 Hz, 1H), 4.51 (d, A of AB, J$_{AB}$ = 12.0 Hz, 1H), 4.46 (d, B of AB, J$_{AB}$ = 12.0 Hz, 1H), 3.77 (dt, J = 11.5, 5.7 Hz, 1H), 3.57 (dd, A of AMX, J$_{AM}$ = 9.1 Hz, J$_{AX}$ = 4.8 Hz, 1H), 3.38 (s, 3H), 3.35 (dd, M of AMX, J$_{AM}$ = 9.1 Hz, J$_{MX}$ = 7.6 Hz, 1H), 3.31 (s, 3H), 3.21 (app. dq, J = 5.6, 3.8 Hz, 1H), 2.88 (dd, J = 8.6, 3.4 Hz, 1H), 2.32 (q, J = 7.6 Hz, 2H), 2.11 (qdd, J = 7.2, 4.4 Hz, 1H), 1.65-1.55 (m, 2H), 1.52-1.42 (m, 3H), 1.76 (dqt, J = 10.9, 7.7, 3.4 Hz, 1H), 1.40-1.37 (m, 2H), 1.15 (t, J = 7.6 Hz, 3H), 1.08 (d, J = 7.0 Hz, 3H), 1.02-0.95 (m, 1H), 0.91 (d, J = 7.0 Hz, 3H), 0.89 (s, 9H), 0.85 (t, J = 7.4 Hz, 3H), 0.84 (d, J = 6.8 Hz, 3H), 0.06 (s, 3H), 0.05 (s, 3H).
$^{13}$C NMR (100 MHz, CDCl$_3$) δ 174.20 (e), 138.92 (e), 128.44 (o), 127.59 (o), 127.55 (o), 85.95 (o), 81.78 (o), 73.46 (o), 73.24 (e), 71.99 (e), 70.44 (o), 61.51 (o), 57.12 (o), 38.62 (o), 37.20 (e), 36.11 (o), 34.30 (o), 30.86 (o), 30.63 (e), 28.21 (e), 27.08 (e), 26.13 (o), 18.26 (e), 16.44 (o), 15.52 (o), 10.63 (o), 9.54 (o), 8.99 (o), −3.80 (o), −4.41 (o).
IR (neat) 2958 (m), 2929 (m), 2880 (w), 2858 (w), 1732 (m), 1379 (w), 1190 (m), 1090 (vs), 1005 (m), 835 (s), 773 (s), 734 (m), 697 (m) cm$^{−1}$.
HRMS (ESI, [M + H]$^+$) calcd for C$_{34}$H$_{63}$O$_6$Si 595.4388, found 595.4414.

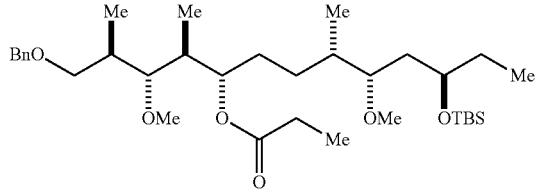 [SMILES: CCC(=O)O[C@@H](CC[C@H](C)[C@H](C[C@@H](CC)O[Si](C)(C)C(C)(C)C)OC)[C@H](C)[C@H](OC)[C@H](C)COCc1ccccc1]

Color and State: Clear oil.
$[α]_D^{20}$ −22.5 (c = 0.49, CHCl$_3$).
$^1$H NMR (400 MHz, CDCl$_3$) δ 7.35-7.31 (m, 4H), 7.30-7.24 (m, 1H), 5.07 (dt, J = 8.3, 4.2 Hz, 1H), 4.51 (d, A of AB, J$_{AB}$ = 12.0 Hz, 1H), 4.47 (d, B of AB, J$_{AB}$ = 12.0 Hz, 1H), 3.78 (dt, J = 11.5, 5.7 Hz, 1H), 3.55 (d, A of ABX, J$_{AB}$ = 9.0 Hz, J$_{AX}$ = 4.0 Hz, 1H), 3.44 (d, B of ABX, J$_{AB}$ = 8.9 Hz, J$_{BX}$ = 6.6. Hz, 1H), 3.38 (s, 3H), 3.30 (s, 3H), 3.22 (dt, J = 7.6, 3.8 Hz, 1H), 3.00 (app. t, J = 6.1 Hz, 1H), 2.30 (q, J = 7.7 Hz, 1H), 2.30 (q, J = 7.5 Hz, 1H), 2.07 (app. quintet of d, J = 6.8, 4.9 Hz, 1H), 2.00 (app. sextet of d, J = 6.7, 4.3 Hz, 1H), 1.77 (dqt, J = 10.2, 6.8, 3.4 Hz, 1H), 1.67-1.54 (m, 2H), 1.51-1.43 (m, 3H), 1.41-1.38 (m, 2H), 1.13 (t, J = 7.6 Hz, 3H), 1.09 (d, J = 6.9 Hz, 3H), 1.02 (app. tt, J = 13.8, 5.6 Hz, 1H), 0.94 (d, J = 7.1 Hz, 3H), 0.90-0.83 (m, 1H), 0.89 (s, 9H), 0.85 (t, J = 7.5 Hz, 3H), 0.84 (d, J = 6.8 Hz, 3H), 0.06 (s, 3H), 0.06 (s, 3H).
$^{13}$C NMR (100 MHz, CDCl$_3$) δ 174.09 (e), 138.92 (e), 128.42 (o), 127.66 (o), 127.53 (o), 86.02 (o), 81.87 (o), 74.58 (o), 73.20 (e), 72.54 (e), 70.51 (o), 60.80 (o), 57.05 (o), 38.59 (e), 37.29 (e), 36.81 (o), 34.05 (o), 30.89 (e), 28.09 (e), 27.66 (e), 27.11 (e), 26.12 (o), 18.25 (e), 15.58 (o), 15.43 (o), 12.19 (o), 9.45 (o), 9.00 (o), −3.81 (o), −4.41 (o).
IR (neat) 2959 (m), 2929 (m), 2882 (m), 2857 (m), 1732 (m), 1380 (w), 1189 (s), 1092 (vs), 1068 (s) 1005 (m), 835 (s), 773 (s), 734 (m), 698 (s) cm$^{−1}$.
HRMS (EI, M$^+$) calcd for C$_{34}$H$_{62}$O$_6$Si 594.4310, found 594.4309.

TABLE 2-continued

Structure and Characterization Data

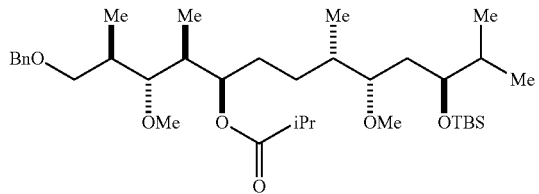 [SMILES: CO[C@@H]([C@@H](C)[C@@H](CC[C@H](C)[C@H](C[C@H](O[Si](C)(C)C(C)(C)C)C(C)C)OC)OC(=O)C(C)C)[C@H](C)COCc1ccccc1]

Color and State: Clear oil.
$[\alpha]_D^{22}$ −6.9 (c = 0.18, CHCl$_3$).
$^1$H NMR (400 MHz, CDCl$_3$) δ 7.35-7.29 (m, 4H), 7.29-7.24 (m, 1H), 5.17 (dt, J = 7.0, 1.4 Hz, 1H), 4.51 (d, A of AB, J$_{AB}$ = 12.0 Hz, 1H), 4.46 (d, B of AB, J$_{AB}$ = 12.0 Hz, 1H), 3.68 (dt, J = 7.8, 3.8 Hz, 1H), 3.57 (dd, A of ABX, J$_{AB}$ = 9.1 Hz, J$_{AX}$ = 4.9 Hz, 1H), 3.38 (s, 3H), 3.34 (B of ABX, J$_{AB}$ = 9.0 Hz, 1H), 3.30 (s, 3H), 3.19 (dt, J = 7.9, 3.8 Hz, 1H), 2.88 (dd, J = 8.7, 3.2 Hz, 1H), 2.54 (heptet, J = 7.0, 1H), 2.11 (dqt, J = 10.6, 7.4, 3.3 Hz, 1H), 1.83 (app. td, J = 7.0, 1.8 Hz, 1H), 1.79 (app. td, J = 6.9, 1.8 Hz, 1H), 1.74 (dqt, J = 10.2, 6.8, 3.4 Hz, 1H), 1.64-1.50 (m, 2H), 1.48-1.40 (m, 1H), 1.33, (ddd, J = 14.2, 8.3, 3.3 Hz), 1.28 (ddd, J = 14.1, 8.3, 3.1 Hz, 1H), 1.17 (d, J = 7.0 Hz, 6H), 1.08 (d, J = 7.0 Hz, 3H), 1.03-0.94 (m, 1H), 0.92 (d, J = 7.0 Hz, 3H), 0.89 (s, 9H), 0.84 (d, J = 7.0 Hz, 6H), 0.82 (d, J = 8.1 Hz, 3H), 0.06 (s, 3H), 0.04 (s, 3H).
$^{13}$C NMR (100 MHz, CDCl$_3$) δ 176.66 (e), 138.83 (e), 128.39 (o), 127.54 (o), 127.50 (o), 85.83 (o), 81.68 (o), 73.57 (o), 73.19 (e), 73.07 (o), 71.89 (e), 61.45 (o), 57.03 (o), 38.67 (o), 36.01 (o), 34.57 (o), 34.34 (o), 33.82 (o), 32.71 (e), 30.53 (e), 27.10 (e), 26.11 (o), 19.30 (o), 19.22 (o), 18.26 (e), 17.85 (o), 16.73 (o), 16.40 (o), 15.48 (o), 10.54 (o), −3.89 (o), −4.31(o).
IR (neat) 2957 (m), 2929 (m), 2876 (m), 2856 (m), 1728 (m), 1460 (m), 1192 (m), 1089 (vs), 1067 (s), 957 (m), 833 (s), 772 (s), 697 (m) cm$^{-1}$.

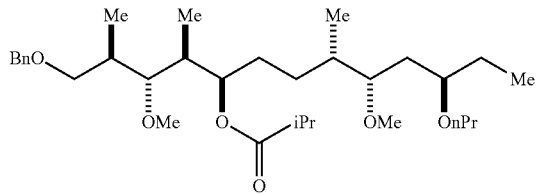

Color and State: Clear oil.
$^1$H NMR (400 MHz, CDCl$_3$) δ 7.35-7.32 (m, 4H), 7.29-7.23 (m, 1H), 5.16 (td, J = 7.0, 1.7 H, 1H), 4.50 (d, A of AB, J$_{AB}$ = 12.0 Hz, 1H), 4.45 (d, B of AB, J$_{AB}$ = 11.9 Hz, 1H), 3.57 (dd. J = 9.2, 4.9 Hz, 1H), 3.48 (dt, J = 9.0, 6.5 Hz, 1H), 3.38-3.33 (m, 2H), 3.37 (s, 3H), 3.33 (s, 3H), 3.27 (dt, J = 9.0, 6.8 Hz, 1H), 3.27 (dd, J = 9.1, 6.2 Hz, 1H), 2.87 (dd, J = 8.8, 3.2 Hz, 1H), 2.11, (app. quintet of t, J = 7.0, 3.2 Hz, 1H), 1.81 (app. dtd, J = 15.7, 7.0, 1.7 Hz, 1H), 1.70 (qdt, J = 10.6, 7.0, 3.5 Hz, 1H), 1.64-1.38 (m, 7H), 1.58 (app. sextet, J = 7.2 Hz, 2H), 1.16 (d, J = 7.0 Hz, 3H), 1.16 (d, J = 7.0 Hz, 3H), 1.07 (d, J = 7.0 Hz, 3H), 1.04-0.97 (m, 1H), 0.95-0.85 (m, 1H), 0.93 (t, J = 7.4 Hz, 3H), 0.91 (d, J = 7.0 Hz, 3H), 0.87 (t, J = 7.5 Hz, 3H), 0.86 (d, J = 6.9 Hz, 3H).
$^{13}$C NMR (100 MHz, CDCl$_3$) δ 176.71 (e), 138.87 (e), 128.41 (o), 127.55 (o), 127.52 (o), 85.87 (o), 81.81 (o), 77.30 (o), 73.21 (e), 73.17 (o), 71.94 (e), 70.84 (e), 61.48 (o), 57.90 (o), 38.66 (o), 36.03 (o), 35.72 (e), 35.21 (o), 34.60 (o), 30.60 (e), 27.54 (e), 27.07 (e), 23.61 (e), 19.31 (o), 19.23 (e), 16.42 (o), 15.35 (o), 11.05 (o), 10.54 (o), 9.43 (o).

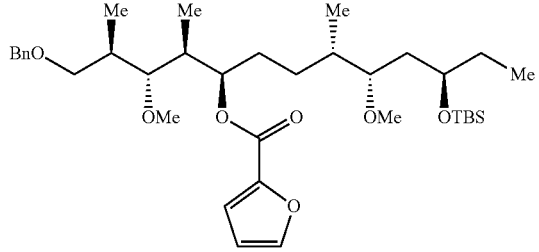

MA-02-045

Color and State: Clear oil.
$[\alpha]_D^{20}$ −15.5 (c = 0.3, CHCl$_3$).
$^1$H NMR (500 MHz, CDCl$_3$) δ 7.57 (dd, J = 1.5, 0.5 Hz, 1H), 7.34-7.29 (m, 4H), 7.29-7.24 (m, 1H), 7.13 (dd, J = 3.2, 1.0 Hz, 1H), 6.49 (dd, J = 3.5, 1.5 Hz, 1H), 5.40 (td, J = 7.2, 2.0 Hz, 1H), 4.51 (d, J = 12.0 Hz, 1H), 4.46 (d, J = 12.0 Hz, 1H), 3.68 (dt, J = 8.0, 3.5 Hz, 1H), 3.57 (dd, J = 9.5, 5.0 Hz, 1H), 3.38 (s, 3H), 3.34 (dd, J = 14.0, 9.0 Hz, 1H), 3.29 (s, 3H), 3.19 (dt, J = 8.5, 3.5 Hz, 1H), 2.95 (dd, J = 8.7, 3.2 Hz, 1H), 2.18-2.10 (m, 1H), 1.94-1.87 (m, 1H), 1.84-1.77 (m, 1H), 1.77-1.70 (m, 2H), 1.69-1.62 (m, 1H), 1.54-1.47(m, 1H), 1.38-1.25 (m, 2H), 1.08 (d, J = 7.0 Hz, 3H), 1.07-1.20 (m, 1H), 1.01 (d, J = 7.0 Hz, 3H), 0.88 (s, 9H), 0.86 (d, J = 7.0 Hz, 3H), 0.84 (d, J = 7.0 Hz, 3H), 0.82 (d, J = 7.0 Hz, 3H), 0.05 (s, 3H), 0.04 (s, 3H).
$^{13}$C NMR (125 MHz, CDCl$_3$) δ 158.56, 146.09, 145.27, 138.75, 128.31, 127.45, 127.41, 117.31, 111.67, 85.74, 81.64, 74.50, 73.54, 73.12, 71.83. 61.49, 56.96, 378.71, 36.00, 34.22, 33.69, 32.67, 30.48, 27.08, 26.01, 18.17, 17.68. 16.72, 16.33, 15.37, 10.57, −3.99, −4.40.
IR (neat) 2955 (m), 2928 (m), 2877 (m), 2855 (m), 1724 (m), 1471 (m), 1293 (s), 1179 (m), 1087 (vs), 937 (m), 832 (s), 762 (s), 697 (m) cm$^{-1}$.
HRMS (ESI, [M + H]$^+$) calcd for C$_{37}$H$_{63}$O$_7$Si 647.4337, found 647.4350.

TABLE 2-continued

Structure and Characterization Data

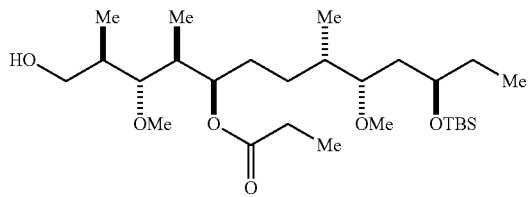 [SMILES: CCC(=O)O[C@H](CC[C@H](C)[C@H](C[C@@H](CC)O[Si](C)(C)C(C)(C)C)OC)[C@H](C)[C@H](OC)[C@H](C)CO]

Color and State: Clear oil.
$[\alpha]_D^{20}$ −31.7 (c = 0.48, CHCl$_3$).
$^1$H NMR (400 MHz, CDCl$_3$) δ 5.18 (td, J = 7.0, 2.0 Hz, 1H), 3.81 (dt, J = 11.1, 3.4 Hz, 1H), 3.78 (dt, J = 11.4, 5.6 Hz, 1H), 3.54 (ddd, J = 11.2, 7.0, 4.4 Hz, 1H), 3.45 (s, 3H), 3.32 (s, 3H), 3.22 (tt, J = 5.7, 3.8 Hz, 1H), 2.95 (dd, J = 8.7, 3.2 Hz, 1H), 2.77 (dd, J = 7.2, 3.5 Hz, 1H), 2.32 (q, J = 7.6 Hz, 2H), 1.90 (td, J = 7.0, 2.0 Hz, 1H), 1.86 (td, J = 6.9, 2.2 Hz, 1H), 1.78 (dqt, J = 10.0, 6.7, 3.3 Hz, 1H), 1.67-1.54 (m, 2H), 1.51-1.43 (m, 3H), 1.15 (t, J = 7.6, 3H), 1.40-1.37 (m, 2H), 1.14 (t, J = 7.0 Hz, 3H), 1.04-0.94 (m, 1H), 0.89 (d, J = 6.4 Hz, 3H), 0.89 (s, 9H), 0.85 (t, J = 7.5 Hz, 3H), 0.85 (d, J = 6.8 Hz, 3H), 0.05 (s, 3H), 0.05 (s, 3H).
$^{13}$C NMR (100 MHz, CDCl$_3$) δ 174.14 (e), 88.68 (o), 81.73 (o), 73.23 (o), 70.38 (o), 64.72 (e), 61.93 (o), 57.07 (o), 38.99 (o), 37.06 (e), 36.28 (o), 34.08 (o), 30.82 (e), 30.52 (e), 28.12 (e), 26.88 (e), 26.07 (o), 18.20 (e), 16.30 (o), 15.54 (o), 10.54 (o), 9.47 (o), 8.93 (o), −3.84 (o), −4.47 (o).
IR (neat) 3454 (w, br.), 2958 (m), 2929 (m), 2881 (m), 2859 (w), 1732 (m), 1381 (m), 1189 (s), 1089 (s), 835 (vs), 773 (vs) cm$^{-1}$.
HRMS (ESI, [M + H]$^+$) calcd for C$_{27}$H$_{57}$O$_6$Si 505.3919, found 505.3941.

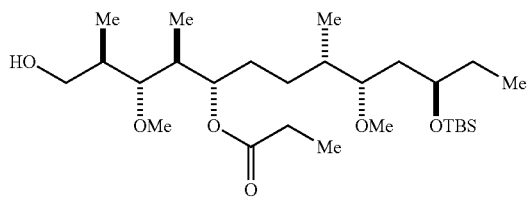 [SMILES: CCC(=O)O[C@@H](CC[C@H](C)[C@H](C[C@@H](CC)O[Si](C)(C)C(C)(C)C)OC)[C@H](C)[C@H](OC)[C@H](C)CO]

Color and State: Clear oil.
$[\alpha]_D^{20}$ −26.2 (c = 0.49, CHCl$_3$).
$^1$H NMR (400 MHz, CDCl$_3$) δ 5.08 (app. q, J = 5.8 Hz, 1H), 3.78 (dt, J = 11.5, 5.6 Hz, 1H), 3.70 (ddd, A of ABMX J$_{AB}$ = 11.0 Hz, J$_{AM}$ = 6.1 Hz, J$_{AX}$ = 3.6 Hz, 1H), 3.58 (app. dt, B of ABMX, J$_{AB}$ = 11.0 Hz, J$_{BM}$ = J$_{BX}$ = 5.5 Hz, 1H), 3.22 (dt, J = 7.4, 3.8 Hz, 1H), 3.46 (s, 3H), 3.30 (s, 3H), 3.04 (app. t, J = 5.7 Hz, 1H), 2.73 (t, M of ABMX, J$_{AM}$ = J$_{BM}$ =11.0 Hz, 1H), 2.32 (q, J = 7.6 Hz, 2H), 1.77 (dqt, J = 10.2, 6.8, 3.4 Hz, 1H), 2.13 (app. qt, J = 7.1, 5.6 Hz, 1H), 1.92 (app. ttt, J = 13.0, 6.5, 3.5 Hz, 1H), 1.78 (dqt, J = 10.2, 6.8, 3.4 Hz, 1H), 1.65-1.59 (m, 2H), 1.52-1.44 (m, 3H), 1.41-1.38 (m, 2H), 1.15-0.98 (m, 1H), 1.14 (t, J = 7.6 Hz, 3H), 1.04 (d, J = 7.0 Hz, 3H), 0.96 (d, J = 7.2 Hz, 3H), 0.89 (s, 9H), 0.86 (t, J = 7.5 Hz, 3H), 0.84 (d, J = 6.9 Hz, 3H), 0.06 (s, 3H), 0.06 (s, 3H).
$^{13}$C NMR (100 MHz, CDCl$_3$) δ 174.07 (e), 89.46 (o), 81.85 (o), 74.47 (o), 70.49 (o), 66.45 (e), 60.84 (o), 57.04 (o), 39.02 (o), 37.25 (o), 37.23 (o), 34.11 (o), 30.89 (e), 28.24 (e), 28.06 (e), 26.75 (e), 26.11 (o), 18.25 (e), 15.75 (o), 15.50 (o), 12.32 (o), 9.44 (o), 8.99 (o), −3.80 (o), −4.41 (o).
IR (neat) 3464 (w, br.), 2958 (m), 2928 (m), 2881 (m), 2858 (m), 1732 (m), 1381 (m), 1189 (s), 1092 (s), 835 (vs), 773 (vs) cm$^{-1}$.
HRMS (ESI, [M + H]$^+$) calcd for C$_{27}$H$_{57}$O$_6$Si 505.3919, found 505.3905.

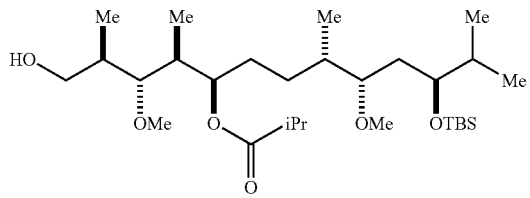 [SMILES: CO[C@@H]([C@@H](C)[C@@H](CC[C@H](C)[C@H](C[C@H](O[Si](C)(C)C(C)(C)C)C(C)C)OC)OC(=O)C(C)C)[C@H](C)CO]

Color and State: Clear oil.
$^1$H NMR (400 MHz, CDCl$_3$) δ 5.17 (td, J = 7.0, 1.8 Hz, 1H), 3.82 (dt, J = 11.0, 3.2 Hz, 1H), 3.69 (dt, J = 7.7, 3.8 Hz, 1H), 3.55 (ddd, J = 11.1, 7.0, 4.4 Hz, 1H), 3.45 (s, 3H), 3.32 (s, 3H), 3.20 (dt, J = 7.9, 3.8 Hz, 1H), 2.95 (dd, J = 8.8, 3.0 Hz, 1H), 2.77 (dd, J = 7.3, 3.4 Hz, 1H), 2.55 (heptet, J = 7.0 Hz, 1H), 1.93-1.85 (m, 2H), 1.77 (dqt, J = 10.3, 6.9, 3.5 Hz, 1H), 1.67-1.53 (m, 2H), 1.50-1.41 (m, 1H), 1.34 (ddd, J = 13.6, 6.8, 3.5 Hz, 1H), 1.29 (ddd, J = 13.9, 8.1, 3.3 Hz, 1H), 1.17 (d, J = 7.0 Hz, 6H), 1.15 (d, J = 7.2 Hz, 3H), 1.04-0.95 (m, 1H), 0.90 (d, J = 8.4 Hz, 3H), 0.89 (s, 9H), 0.86 (d, J = 7.3 Hz, 6H), 0.83 (d, J = 7.8 Hz, 3H), 0.06 (s, 3H), 0.05 (s, 3H).
$^{13}$C NMR (100 MHz, CDCl$_3$) δ 176.72 (e), 88.74 (o), 81.72 (o), 73.60 (o), 72.95 (o), 64.75 (e), 62.01 (o), 57.08 (o), 39.15 (o), 36.16 (o), 34.58 (e), 34.22 (o), 33.87 (o), 32.64 (e), 30.52 (e), 26.95 (e), 26.13 (o), 19.30 (o), 19.25 (o), 18.29 (e), 17.91 (o), 16.71 (o), 16.38 (o), 15.56 (o), 10.53 (o), −3.86 (o), −4.29 (o).

TABLE 2-continued

Structure and Characterization Data

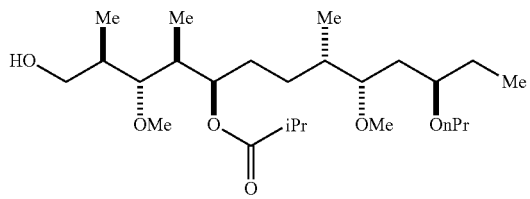

Color and State: Clear oil.
¹H NMR (400 MHz, CDCl₃) δ 5.16 (td, J = 6.9, 1.7 Hz, 1H), 3.80 (dd, J = 11.0, 3.3 Hz, 1H), 3.53 (dd, J = 11.0, 4.2 Hz, 1H), 3.48 (dt, J = 9.0, 6.6 Hz, 1H), 3.43 (s, 3H), 3.38-3.32 (m, 1H), 3.34 (s, 3H), 3.26 (dt, J = 9.1, 6.8 Hz 1H), 3.26 (dd, J = 12.3, 3.4 Hz, 1H), 2.93 (dd, J = 8.8, 3.0 Hz, 1H), 2.83 (br. s, 1H), 2.53 (septet, J = 7.0 Hz, 1H), 1, 92-1.84 (m, 2H), 1.73 (dqt, J = 10.1, 6.8, 3.5 Hz, 1H), 1.62-1.38 (m, 9H), 1.16 (d, J = 7.0 Hz, 6H), 1.14 (d, J = 7.2 Hz, 3H), 1.04-0.97 (m, 1H), 0.92 (t, J = 7.5 Hz, 3H), 0.88 (d, J = 7.8 Hz, 3H), 0.87 (t, J = 7.8 Hz, 3H), 0.86 (d, J = 6.9 Hz, 3H).
¹³C NMR (100 MHz, CDCl₃) δ 176.71 (e), 88.70 (o), 81.80 (o), 77.28 (o), 72.98 (o), 70.86 (e), 64.71 (e), 61.99 (o), 57.89 (o), 39.07 (o), 36.16 (o), 35.61 (e), 34.99 (o), 34.56 (o), 30.51 (e), 27.35 (e), 27.06 (e), 23.59 (e), 19.28 (e), 19.22 (e), 16.35 (e), 15.41 (e), 11.03 (e), 10.49 (e), 9.42 (e).

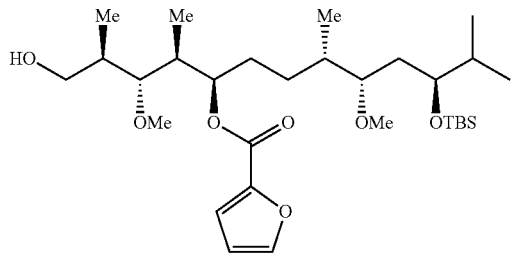

MA-02-048

[α]$_D^{20}$ −19.0 (c = 0.6, CHCl₃).
¹H NMR (500 MHz, CDCl₃) δ 7.57 (t, J = 1.2 Hz, 1H), 7.13 (d, J = 4.0, 1.0 Hz, 1H), 6.50 (dd, J = 3.5, 1.5 Hz, 1H), 5.40 (td, J = 7.0, 2.0 Hz, 1H), 3.83 (dd, J = 11.2, 3.7 Hz, 1H), 3.67 (dt, J = 8.5, 3.5 Hz, 1H), 3.45 (s, 3H), 3.30 (s, 3H), 3.20 (dt, J = 9.0, 3.5 Hz, 1H), 3.02 (dd, J = 9.0, 3.0 Hz, 1H), 2.80 (br. s, 1H), 2.00-1.93 (m, 1H), 1.92-1.86 (m, 1H), 1.84-1.79 (m, 1H), 1.76-1.65 (m, 3H), 1.55-1.46 (m, 1H), 1.38-1.25 (m, 3H), 1.14 (d, J = 7.5 Hz, 3H), 1.11-1.02 (m, 1H), 0.99 (d, J = 7.0 Hz, 3H), 0.87 (s, 9H), 0.86 (d, J = 7.0 Hz, 3H), 0.84 (d, J = 6.5 Hz, 3H), 0.82 (d, J = 7.0 Hz, 3H), 0.04 (s, 3H), 0.03 (s, 3H).
¹³C NMR (125 MHz, CDCl₃) δ 158.49, 146.22, 145.09, 117.48, 111.72, 88.52, 81.65, 74.24, 73.53, 64 61, 62.01, 56.96, 39.17, 36.17, 34.06, 33.71, 32.55, 30.44, 26.91, 25.99, 18.16, 17.72, 16.66, 16.23, 15.42, 10.53, −3.99, −4.42.
IR (neat) 3420 (w, br.), 2957 (m), 2930 (m), 2881 (m), 2858 (m), 1714 (s), 1471 (m), 1386 (m), 1295 (s), 1180 (m), 1079 (vs), 938 (m), 833 (s), 764 (vs), 733 (s), 664 (w) cm⁻¹.
HRMS (ESI, [M + H]⁺) calcd for C₃₀H₅₇O₇Si 557.3868, found 557.3864.

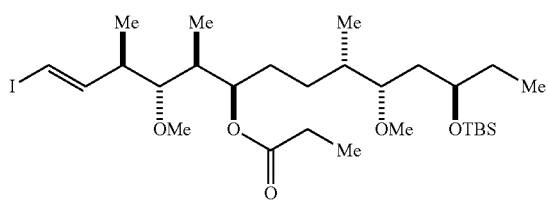 [SMILES: CCC(=O)O[C@H](CC[C@H](C)[C@H](C[C@@H](CC)O[Si](C)(C)C(C)(C)C)OC)[C@H](C)[C@H](OC)[C@H](C)/C=C/I]

Color and State: Pale yellow solid.
[α]$_D^{20}$ −32.2 (c = 0.51, CHCl₃).
¹H NMR (400 MHz, CDCl₃) δ 6.56 (dd, J = 14.6, 8.9 Hz, 1H), 6.02 (d, J = 14.5 Hz, 1H), 5.19 (td, J = 7.0, 1.4 Hz, 1H), 3.40 (s, 3H), 3.33 (s, 3H), 3.78 (dt, J = 12.1, 5.3 Hz, 1H), 3.22 (dt, J = 7.7, 3.7 Hz, 1H), 2.76 (dd, J = 9.5, 2.3 Hz, 1H), 2.48 (dqd, J = 9.6, 6.8, 2.4 Hz, 1H), 2.32 (q, J = 7.6 Hz, 2H), 1.98 (tdd, J = 11.2, 9.3, 4.6, 1H), 1.78 (dqt, J = 10.1, 6.8, 3.4 Hz, 1H), 1.66-1.56 (m, 2H), 1.54-1.42 (m, 4H), 1.40 (dd, J = 4.5, 2.5, 1H), 1.38 (dd, J = 4.6, 2.5 Hz, 1H), 1.15 (t, J = 7.8 Hz, 3H), 1.12 (d, J = 7.3 Hz, 3H), 0.89 (s, 9H), 0.86 (t, J = 6.9 Hz, 3H), 0.85 (d, J = 6.7 Hz, 3H), 0.82 (d, J = 7.0 Hz, 3H), 0.06 (s, 3H), 0.05 (s, 3H).
¹³C NMR (100 MHz, CDCl₃) δ 174.19 (e), 147.64 (o), 86.05 (o), 81.76 (o), 75.14 (o), 73.38 (o), 70.42 (o), 61.68 (o), 57.14 (o), 43.45 (o), 39.29 (o), 37.13 (e), 34.11 (o), 30.88 (e), 30.51 (e), 28.19 (e), 26.98 (e), 26.13 (o), 18.26 (e), 18.14 (o), 15.49 (o), 9.89 (o), 9.55 (o), 9.02 (o), −3.79 (o), −4.41 (o).
IR (neat) 2957 (m), 2929 (m), 2880 (w), 2857 (w), 1732 (m), 1602 (w), 1381 (m), 1188 (s), 1092 (vs), 1067 (s), 966 (m), 835 (vs), 773 (vs) cm⁻¹.
HRMS (ESI, [M + Na]⁺) calcd for C₂₈H₅₅O₅INaSi 649.2756, found 649.2756.

TABLE 2-continued

Structure and Characterization Data

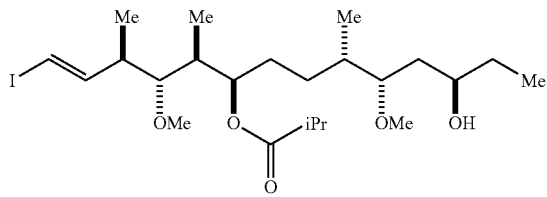 [SMILES: CC[C@@H](O)C[C@H](OC)[C@@H](C)CC[C@@H](OC(=O)C(C)C)[C@H](C)[C@H](OC)[C@H](C)/C=C/I]

Color and State: Pale yellow oil.
$[\alpha]_D^{23}$ −30.2 (c = 0.48, CHCl$_3$).
$^1$H NMR (400 MHz, CDCl$_3$) δ 6.56 (dd, J = 14.6, 9.0 Hz, 1H), 6.02 (d, J = 14.5 Hz, 1H), 5.17 (td, J = 7.0, 1.5 Hz, 1H), 3.49 (dt, J = 9.0, 6.5 Hz, 1H), 3.40 (s, 3H), 3.38-3.33 (m, 1H), 3.35 (s, 3H), 3.28 (dt, J = 8.9, 6.8 Hz, 1H), 3.27 (dd, J = 5.4, 3.2 Hz, 1H), 2.74 (dd, J = 9.5, 2.3 Hz, 1H), 2.54 (septet, J = 7.0, 1H), 2.47 (dqd, J = 9.3, 7.0, 2.1 Hz, 1H), 1.72 (dqt, J = 10.0, 6.6, 3.4, 1H), 1.66-1.40 (m, 10H), 1.17 (d, J = 6.9 Hz, 3H), 1.17 (d, J = 7.0 Hz, 3H), 1.12 (d, J = 7.0 Hz, 3H), 1.05-0.99 (m, 1H), 0.94 (t, J = 7.4 Hz, 3H), 0.89 (t, J = 7.4 Hz, 3H), 0.87 (d, J = 6.9 Hz, 3H), 0.83 (d, J = 7.0 Hz, 3H).
$^{13}$C NMR (100 MHz, CDCl$_3$) δ 176.72 (e), 147.63 (o), 86.07 (o), 81.86 (o), 77.34 (o), 75.13 (o), 73.12 (o), 70.86 (e), 61.68 (o), 57.96 (o), 43.43 (o), 39.37 (o), 35.70 (e), 35.09 (o), 34.61 (o), 30.52 (e), 27.51 (e), 27.12 (e), 23.63 (e), 19.35 (o), 19.26 (o), 15.33 (o), 11.07 (o), 9.89 (o), 9.48 (o).
IR (neat) 2961 (m), 2925 (m), 2873 (m), 1727 (m), 1600 (w), 1191 (m), 1089 (vs), 965 (m) cm$^{-1}$.

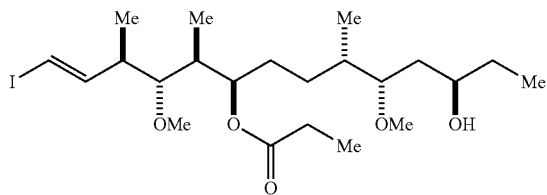 [SMILES: CCC(=O)O[C@H](CC[C@H](C)[C@H](C[C@H](O)CC)OC)[C@H](C)[C@H](OC)[C@H](C)/C=C/I]

Color and State: Light yellow oil
$[\alpha]_D^{20}$ −15.7 (c = 1.00, CHCl$_3$).
$^1$H NMR (400 MHz, CDCl$_3$) δ 6.56 (dd, J = 14.6, 9.0 Hz, 1H), 6.03 (d, J = 14.6 Hz, 1H), 5.18 (app. td, J = 7.0, 1.5 Hz, 1H), 3.73 (app. qt, J = 6.0, 3.0, 1H), 3.40 (s, 3H), 3.38 (s, 3H), 3.30 (ddd, J = 8.4, 5.1, 3.1 Hz, 1H), 2.75 (dd, J = 9.5, 2.3 Hz, 1H), 2.48 (dqd, J = 9.1, 6.8, 2.3 Hz, 1H), 2.32 (q, J = 7.6 Hz, 2H), 1.84-1.75 (m, 1H), 1.64-1.51 (m, 2H), 1.50-1.40 (m, 4H), 1.32-1.25 (m, 1H), 1.15 (t, J = 7.6 Hz, 3H), 1.12 (d, J = 6.8 Hz, 3H), 0.94 (t, J = 7.5 Hz, 3H), 0.90 (d, J = 6.8 Hz, 3H), 0.83 (d, J = 7.0 Hz, 3H).
$^{13}$C NMR (100 MHz, CDCl$_3$) δ 174.23 (e), 147.59 (o), 86.06 (o), 83.06 (o), 75.20 (o), 73.29 (o), 70.70 (o), 61.73 (o), 57.76 (o), 43.46 (o), 39.40 (o), 35.86 (e), 34.68 (o), 30.72 (e), 30.34 (e), 28.17 (e), 27.40 (e), 18.13 (o), 15.75 (o), 10.27 (o), 9.92 (o), 9.54 (o).
IR (neat) 3448 (w, br.), 2962 (m), 2928 (m), 2876 (w), 2831 (w), 1728 (m), 1600 (w), 1187 (s), 1088 (vs), 965 (s) cm$^{-1}$.
HRMS (ESI, [M + H]$^+$) calcd for C$_{22}$H$_{42}$O$_5$I 513.2071, found 513.2058.

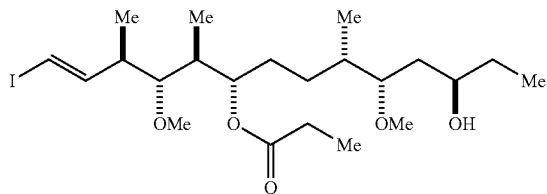 [SMILES: CCC(=O)O[C@@H](CC[C@H](C)[C@H](C[C@H](O)CC)OC)[C@H](C)[C@H](OC)[C@H](C)/C=C/I]

Color and State: Yellow oil.
$[\alpha]_D^{20}$ −11.5 (c = 0.52, CHCl$_3$).
$^1$H NMR (400 MHz, CDCl$_3$) δ 6.59 (dd, J = 14.5 Hz, 1H), 6.02 (d, J = 14.5 Hz, 1H), 5.05 (dt, J = 8.5, 4.3 Hz, 1H), 3.76-3.69 (m, 1H), 3.39 (s, 3H), 3.36 (s, 3H), 3.30 (ddd, J = 8.3, 5.0, 3.0 Hz, 1H), 2.87 (dd, J = 6.9, 4.0 Hz, 1H), 2.52-2.42 (m, 1H), 2.50 (d, J = 1.8 Hz, 1H), 2.32 (q, J = 7.6 Hz, 2H), 1.98 (app. quintet of d, J = 7.0, 5.1 Hz, 1H), 1.85-1.75 (m, 1H), 1.64-1.54 (m, 2H), 1.52-1.41 (m, 4H), 1.14 (t, J = 7.6 Hz, 3H), 1.09 (d, J = 6.9 Hz, 3H), 1.07-0.98 (m, 1H), 0.97-0.83 (m, 1H), 0.94 (t, J = 7.4 Hz, 3H), 0.89 (d, J = 6.8 Hz, 3H), 0.85 (d, J = 7.1 Hz, 3H).
$^{13}$C NMR (100 MHz, CDCl$_3$) δ 174.08 (e), 148.53 (o), 86.57 (o), 83.18 (o), 75.06 (o), 74.63 (o), 70.70 (o), 60.47 (o), 57.74 (o), 43.34 (o), 39.13 (o), 35.93 (e), 34.69 (o), 30.73 (e), 28.06 (e), 27.92 (e), 27.52 (e), 17.97 (o), 15.73 (o), 11.87 (o), 10.25 (o), 9.48 (o).
HRMS (ESI, [M + H]$^+$) calcd for C$_{22}$H$_{42}$O$_5$I 513.2071, found 513.2047.
IR (neat) 3438 (w, br.), 2961 (m), 2925 (m), 2877 (m), 2826 (w), 1728 (m), 1600 (w), 1186 (s), 1089 (vs), 961 (m) cm$^{-1}$.

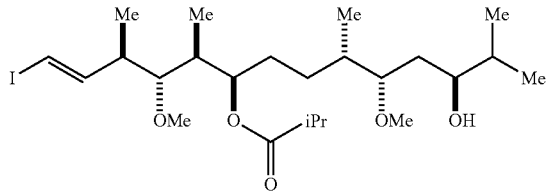 [SMILES: CO[C@@H]([C@@H](C)[C@@H](CC[C@H](C)[C@H](C[C@H](O)C(C)C)OC)OC(=O)C(C)C)[C@H](C)/C=C/I]

TABLE 2-continued

Structure and Characterization Data

Color and State: Dark yellow oil.
$^1$H NMR (400 MHz, CDCl$_3$) δ 6.56 (dd, J = 14.6, 9.0 Hz, 1H), 6.03 (d, J = 14.6 Hz, 1H), 5.17 (td, J = 7.0, 1.6 Hz, 1H), 3.54 (ddt, J = 11.0, 8.2, 5.5, 2.7, 1H), 3.29 (ddd, J = 8.1, 4.8, 3.4 Hz, 1H), 2.74 (dd, J = 9.6, 2.4 Hz, 1H), 2.34 (d, J = 5.0 Hz, 1H), 3.40 (s, 3H), 3.38 (s, 3H), 2.54 (septet, J = 7.0 Hz, 1H), 2.48 (dqd, J = 15.9, 6.9, 2.3 Hz, 1H), 1.85-1.75 (m, 1H), 1.63 (septet of d, J = 6.6, 1.2 Hz, 1H), 1.65-1.40 (m, 5H), 1.34-1.24 (m, 1H), 1.18 (d, J = 7.0 Hz, 3H), 1.17 (d, J = 7.0 Hz, 3H), 1.12 (d, J = 7.0 Hz, 3H), 1.04-0.97 (m, 1H), 0.95 (d, J = 6.7 Hz, 3H), 0.91 (d, J = 6.8 Hz, 3H), 0.90 (d, J = 6.8 Hz, 3H), 0.84 (d, J = 7.0 Hz, 3H).

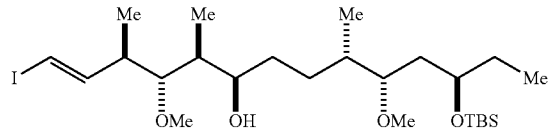 [SMILES: CC[C@H](C[C@H](OC)[C@@H](C)CC[C@@H](O)[C@H](C)[C@H](OC)[C@H](C)/C=C/I)O[Si](C)(C)C(C)(C)C]

[α]$_D^{20}$ −10.1 (c = 0.51, CHCl$_3$).
$^1$H NMR (400 MHz, CDCl$_3$) δ 6.55 (dd, J = 14.5, 8.6 Hz, 1H), 6.08 (d, J = 14.5 Hz, 1H), 3.47 (s, 3H), 3.33 (s, 3H), 3.87 (br. t, J = 6.4 Hz, 1H), 3.78 (dt, J = 12.4, 5.0 Hz, 1H), 3.24 (dt, J = 7.6, 3.8 Hz, 1H), 3.00 (app. t, J = 5.8 Hz, 1H), 2.81 (d, J = 3.0 Hz, 1H), 2.54 (app. sextet, J = 7.1 Hz, 1H), 2.54 (app. dq, J = 15.0, 6.7 Hz, 1H), 1.78 (dqt, J = 10.2, 6.8, 3.5 Hz, 1H), 1.52-1.40 (m, 6H), 1.07-0.97 (m, 1H), 1.03 (d, J = 6.8 Hz, 3H), 0.94 (d, J = 7.0 Hz, 3H), 0.89 (s, 9H), 0.87-0.84 (m, 1H), 0.86 (t, J = 7.4 Hz, 3H), 0.86 (d, J = 6.7 Hz, 3H), 0.06 (s, 3H), 0.06 (s, 3H).
$^{13}$C NMR (100 MHz, CDCl$_3$) δ 148.57 (o), 89.83 (o), 81.95 (o), 75.44 (o), 71.39 (o), 70.50 (o), 61.92 (o), 57.15 (o), 43.72 (o), 38.69 (o), 37.27 (e), 34.80 (o), 33.17 (e), 30.86 (e), 27.98 (e), 26.12 (o), 18.26 (e), 16.96 (o), 15.59 (o), 10.95 (o), 9.03 (o), −3.80 (o), −4.40 (o).
IR (neat) 3461 (w, br.), 2957 (m), 2928 (m), 2880 (m), 2857 (m), 1602 (w), 1381 (m), 1092 (s), 967 (m), 835 (vs), 772 (vs) cm$^{-1}$.
HRMS (ESI, [M + H]$^+$) calcd for C$_{25}$H$_{52}$O$_4$ISi 571.2674, found 571.2647.

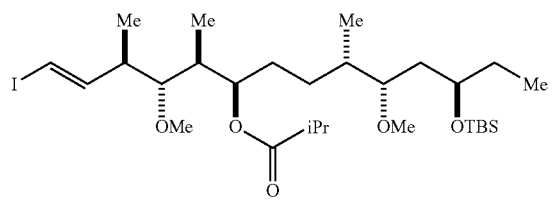 [SMILES: CC[C@H](C[C@H](OC)[C@@H](C)CC[C@@H](OC(=O)C(C)C)[C@H](C)[C@H](OC)[C@H](C)/C=C/I)O[Si](C)(C)C(C)(C)C]

[α]$_D^{20}$ −34.8 (c = 0.50, CHCl$_3$).
$^1$H NMR (400 MHz, CDCl$_3$) δ 6.56 (dd, J = 14.6, 9.0 Hz, 1H), 6.02 (d, J = 14.6 Hz, 1H), 5.17 (td, J = 7.0, 1.4 Hz, 1H), 3.78 (dt, J = 12.3, 5.2 Hz, 1H), 3.40 (s, 3H), 3.32 (s, 3H), 3.22 (dt, J = 7.7, 3.8 Hz, 1H), 2.74 (dd, J = 9.5, 2.4 Hz, 1H), 2.54 (heptet, J = 7.0 Hz, 1H), 2.48 (dqd, J = 9.6, 6.9, 2.5 Hz, 1H), 1.77 (dqt, J = 10.1, 6.7, 3.4 Hz, 1H), 1.66-1.51 (m, 4H), 1.50-1.42 (m, 3H), 1.40 (dd, J = 4.4, 2.8 Hz, 1H), 1.38 (dd, J = 4.4, 2.6 Hz, 1H), 1.17 (d, J = 7.0 Hz, 6H), 1.12 (d, J = 7.0 Hz, 3H), 1.04-0.95 (m, 1H), 0.90-0.82 (m, 1H), 0.89 (s, 9H), 0.86 (t, J = 6.8 Hz, 3H), 0.83 (d, J = 7.1 Hz, 3H), 0.06 (s, 3H), 0.05 (s, 3H).
$^{13}$C NMR (100 MHz, CDCl$_3$) δ 176.72 (e), 147.62 (o), 86.06 (o), 81.75 (o), 75.13 (o), 73.08 (o), 70.42 (o), 61.69 (o), 57.14 (o), 43.43 (o), 39.42 (o), 37.18 (e), 34.61 (o), 34.14 (o), 30.88 (e), 30.52 (e), 27.02 (e), 26.13 (o), 19.35 (o), 19.28 (o), 18.26 (e), 18.14 (o), 15.48 (o), 9.89 (o), 9.01 (o), −3.79 (o), −4.41 (o).
IR (neat) 2958 (m), 2929 (m), 2879 (m), 2857 (w), 1729 (s), 1602 (w), 1383 (m), 1191 (m), 1092 (vs), 1067 (s), 835 (vs), 773 (vs) cm$^{-1}$.
HRMS (ESI, [M + H]$^+$) calcd for C$_{29}$H$_{58}$O$_5$ISi 641.3093, found 641.3111.

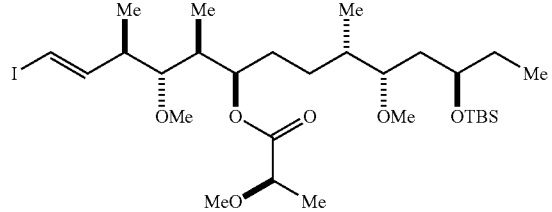 [SMILES: CC[C@H](C[C@H](OC)[C@@H](C)CC[C@@H](OC(=O)[C@@H](C)OC)[C@H](C)[C@H](OC)[C@H](C)/C=C/I)O[Si](C)(C)C(C)(C)C]

$^1$H NMR (400 MHz, CDCl$_3$) δ 6.55 (dd, J = 14.6, 8.9 Hz, 1H), 6.04 (d, J = 14.5 Hz, 1H), 5.31 (app. t, J = 6.8 Hz, 1H), 3.86 (q, J = 6.8 Hz, 1H), 3.77 (app. quintet, J = 5.6 Hz, 1H), 3.42 (s, 3H), 3.41 (s, 3H), 3.32 (s, 3H), 3.22 (dt, J = 7.4, 3.8 Hz, 1H), 2.72 (dd, J = 9.4, 2.0 Hz, 1H), 2.49 (qd, J = 8.4, 6.8 Hz, 1H), 1.78 (dqt, J = 9.9, 6.7, 3.4 Hz, 1H), 1.68-1.52 (m, 3H), 1.51-1.44 (m, 3H), 1.43-1.37 (m, 2H), 1.41 (d, J = 6.9 Hz, 3H), 1.11 (d, J = 6.9 Hz, 3H), 1.01 (qt, J = 9.8, 4.8 Hz, 1H), 0.89 (s, 9H), 0.85 (d, J = 6.8 Hz, 3H), 0.85 (t, J = 7.5 Hz, 3H), 0.85 (d, J = 6.9 Hz, 3H), 0.06 (s, 6H).

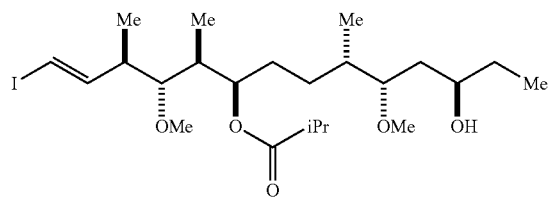 [SMILES: CC[C@@H](O)C[C@H](OC)[C@@H](C)CC[C@@H](OC(=O)C(C)C)[C@H](C)[C@H](OC)[C@H](C)/C=C/I]

TABLE 2-continued

Structure and Characterization Data

[α]$_D^{23}$ −25.9 (c = 0.51, CHCl$_3$).
$^1$H NMR (400 MHz, CDCl$_3$) δ 6.55 (dd, J = 14.6, 9.0 Hz, 1H), 6.03 (d, J = 14.6 Hz, 1H), 5.17 (td, J = 7.0, 1.4 Hz, 1H), 3.77-3.69 (m, 1H), 3.40 (s, 3H), 3.37 (s, 3H), 3.30 (ddd, J = 8.4, 5.1, 3.1 Hz, 1H), 2.74 (dd, J = 9.6, 2.3 Hz, 1H), 2.54 (septet, J = 7.0 Hz, 1H), 2.50-2.44 (m, 1H), 2.47 (d, J = 4.9 Hz, 1H), 1.84-1.75 (m, 1H), 1.65-1.54 (m, 4H), 1.52-1.39 (m, 4H), 1.17 (d, J = 7.0 Hz, 3H), 1.17 (d, J = 7.0 Hz, 3H), 1.12 (d, J = 7.0 Hz, 3H), 1.00 (ddd, J = 12.9, 10.0, 4.5 Hz, 1H), 0.94 (t, J = 7.5 Hz, 3H), 0.90 (d, J = 6.8 Hz, 3H), 0.83 (d, J = 7.0 Hz, 3H).
$^{13}$C NMR (100 MHz, CDCl$_3$) δ 176.75 (e), 147.57 (o), 86.06 (o), 83.07 (o), 75.21 (o), 72.99 (o), 70.68 (o), 61.74 (o), 57.73 (o), 43.44 (o), 39.53 (o), 35.82 (e), 34.63 (o), 34.60 (o), 30.72 (e), 30.34 (e), 27.37 (e), 19.35 (o), 19.27 (o), 18.14 (o), 15.76 (o), 10.28 (o), 9.92 (o).
IR (neat) 3439 (w, br.), 2964 (m), 2930 (m), 2874 (m), 2829 (w), 1724 (m), 1600 (w), 1193 (m), 1088 (vs), 965 (m) cm$^{-1}$.
HRMS (ESI, [M + Na]$^+$) calcd for C$_{23}$H$_{44}$IO$_5$ 527.2228, found 527.2208.

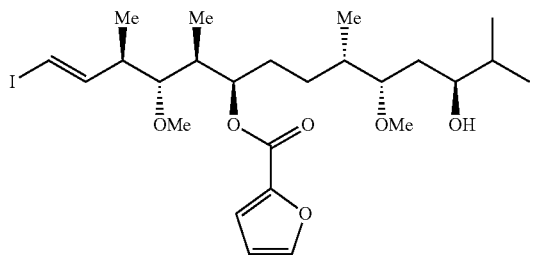

MA-02-053

[α]$_D^{20}$ −8.9 (c = 1.0, CHCl$_3$).
$^1$H NMR (400 MHz, CDCl$_3$) δ 7.57 (dd, J = 2.0. 0.8 Hz, 1H), 7.12 (d, J = 3.6 Hz, 1H), 6.56 (dd, J = 14.4, 8.8 Hz, 1H), 6.02 (d, J = 14.8 Hz, 1H), 5.40 (td, J = 7.2, 1.6 Hz, 1H), 3.55-3.48 (m, 1H), 3.41 (s, 3H), 3.36 (s, 3H), 3.30-3.24 (m, 1H), 2.81 (dd, J = 9.8, 2.0 Hz, 1H), 2.52-2.45 (m, 1H), 2.41 (br. s, 1H), 1.85-1.76 (m, 1H), 1.76-1.55 (m, 5H), 1.55-1.43 (m, 3H), 1.38-1.25 (m, 3H), 1.10 (d, J = 6.8 Hz, 3H), 1.09-0.99 (m, 1H), 0.91 (d, J = 7.8 Hz, 3H), 0.91 (d, J = 7.8 Hz, 3H), 0.89 (d, J = 6.4 Hz, 3H), 0.84(d, J = 6.8 Hz, 3H).
$^{13}$C NMR (100 MHz, CDCl$_3$) δ 158.52, 147.37, 146.25, 144.99, 117.52, 111.74, 85.76, 83.22, 75.13, 74.31, 73.78, 61.69, 57.80, 43.35, 39.65, 34.77, 33.92, 33.15, 30.35, 27.53, 18.65, 17.99, 17.79, 15.62, 9.85.
IR (neat) 3482 (w, br.), 2957 (m), 2931 (m), 2873 (m), 2829 (w), 1711 (s), 1471 (m), 1386 (w), 1295 (vs), 1178 (m), 1118 (s), 1088 (s), 943 (w), 762 (m) cm$^{-1}$.
HRMS (ESI, [M + H]$^+$) calcd for C$_{25}$H$_{42}$O$_6$I 565.2020, found 565.2028.

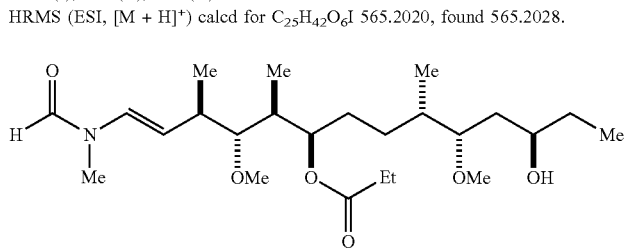

1

Color and State: Clear oil.
[α]$_D^{20}$ −21.6 (c = 0.50, CHCl$_3$).
$^1$H NMR (400 MHz, CDCl$_3$) δ 8.27 (s, 1H) *[8.05 (s, 1H)], 5.19 (td, J = 6.8, 1.7 Hz, 1H) *[5.18 (td, J = 7.0, 1.9 Hz, 1H)], 5.10 (dd, J = 14.2, 9.3 Hz, 1H) *[5.13 (dd, J = 14.5, 9.6 Hz, 1H)], 6.45 (d, J = 14.1 Hz, 1H) *[7.12 (d, J = 14.7 Hz, 1H)], 3.76-3.68 (m, 1H), 3.44 (s, 3H) *[3.44 (s, 3H)], 3.36 (s, 3H), 3.29 (ddd, J = 8.3, 4.9, 3.1 Hz, 1H), 3.01 (s, 3H) *[3.04 (s, 3H)], 2.81 (dd, J = 9.3, 2.2 Hz, 1H), 2.51-2.40 (m, 2H), 2.33 (q, J = 7.6 Hz, 2H), 1.83-1.73 (m, 1H), 1.65-1.54 (m, 3H), 1.51-1.39 (m, 4H), 1.36-1.25 (m, 1H), 1.17 (d, J = 7.8 Hz, 3H) *[1.15 (d, J = 7.4 Hz, 3H)], 1.16 (d, J = 6.9 Hz, 1H) *[1.15 (d, J = 7.4 Hz, 3H)], 1.05-0.97 (m, 1H), 0.93 (t, J = 7.4 Hz, 3H), 0.89 (d, J = 6.8 Hz, 3H) *[0.88 (d, J = 6.8 Hz, 3H)], 0.84 (d, J = 7.0 Hz, 3H) *[0.83 (d, J = 7.0 Hz, 3H)].
$^{13}$C NMR (100 MHz, CDCl$_3$) δ 174.25 (e) *(174.29), 162.31 (o) *(160.99), 128.71 (o) *(124.74), 111.91 (o) *(113.66), 86.68 (o) *(86.74), 83.04 (o) *(73.48), 70.65 (o) *(70.71), 61.93 (o) *(61.99), 57.77 (o) *(57.71), 39.66 (o), 37.96 (o) *(38.28), 35.99 (e) *(35.88), 34.93 (o) *(34.86), 27.73 (o) *(33.25), 30.75 (e) *(30.69), 30.59 (e) *(30.45), 28.19 (e), 27.53 (e) *(27.39), 20.26 (o) *(20.43), 15.78 (o), 10.23 (o) *(10.26), 10.00 (o) *(9.85), 9.55(o).
IR (neat) 3439 (w, br.), 2961 (w), 2929 (m), 2876 (w), 2827 (w), 1727 (m), 1688 (m), 1632 (vs), 1190 (m), 1089 (s), 1072 (s) cm$^{-1}$.
HRMS (ESI, [M + H]$^+$) calcd for C$_{24}$H$_{46}$NO$_6$ 444.3320, found 444.3304.

TABLE 2-continued

Structure and Characterization Data

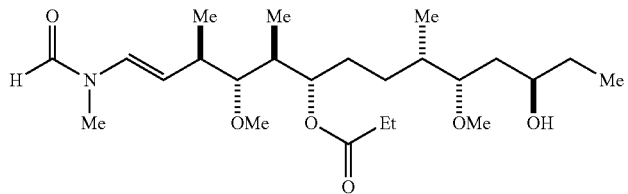

2

Color and State: Clear oil.
[α]$_D^{20}$ −44.7 (c = 0.48, CHCl$_3$).
$^1$H NMR (400 MHz, CDCl$_3$) δ 8.26 (s, 1H) *[8.04 (s, 1H)], 6.44 (d, J = 14.1 Hz, 1H) *[7.10 (d, J = 14.7 Hz, 1H)], 5.14 (dd, J = 14.3, 9.1 Hz, 1H) *[5.20 (dd, J = 16.1, 9.1 Hz, 1H)], 5.09 (dt, J = 4.7, 4.1 Hz, 1H) *[5.12-5.07 (m, 1H)], 3.76-3.69 (m, 1H), 3.42 (s, 3H) *[3.43 (s, 3H)], 3.36 (s, 3H), 3.30 (ddd, J = 8.2, 4.8, 3.2 Hz, 1H), 3.00 (s, 3H) *[3.04 (s, 3H)], 2.90 (dd, J = 7.5, 3.8 Hz, 1H) *[2.88 (dd, J = 4.9, 3.4 Hz, 1H)], 2.48 (br. d, J = 5.0 Hz, 1H) *[2.51 (br. d, J = 4.5 Hz, 1H)], 2.51-2.37 (m, 1H), 2.32 (q, J = 7.5 Hz, 2H) *[2.31 (q, J = 7.5 Hz, 2H)], 1.97 (app. quintet of d, J = 7.1, 4.8 Hz, 1H) *[1.91 (app. quintet of d, J = 7.5, 4.3 Hz, 1H)], 1.84-1.75 (m, 1H), 1.63-1.54 (m, 3H), 1.54-1.42 (m, 4H), 1.15 (t, J = 7.5 Hz, 3H) *[1.13 (t, J = 7.2 Hz, 3H)], 1.14 (d, J = 6.7 Hz, 3H), 1.10-1.00 (m, 1H), 0.94 (t, J = 7.4 Hz, 3H), 0.89 (d, J = 6.8 Hz, 3H), 0.85 (d, J = 7.0 Hz, 3H), *[0.82 (d, J = 7.1 Hz, 3H)].
$^{13}$C NMR (100 MHz, CDCl$_3$) δ 174.06 (e) *(174.02), 162.32 (o) *(160.96), 128.40 (o) *(124.47), 113.03 (o) *(114.53), 87.29 (o) *(87.44), 83.18 (o), 74.72 (o) *(74.82), 70.67 (o), 60.77 (o) *(60.91), 57.73 (o), 39.44 (o) *(39.74), 37.91 (o) *(38.12), 35.95 (e) *(35.91), 34.76 (o), 30.75 (e), 28.06 (e) *(27.90), 27.77 (e), 27.72 (o) *(33.27), 27.69 (e) *(27.40), 19.96 (o) *(20.03), 15.76 (o) *(15.80), 11.76 (o) *(11.55), 10.24 (o), 9.47 (o).
IR (neat) 3481 (w, br.), 2961 (m), 2925 (m), 2877 (w), 2825 (w), 1727 (m), 1688 (m), 1652 (vs), 1188 (m), 1077 (s) cm$^{-1}$.
HRMS (ESI, [M + H]$^+$) calcd for C$_{24}$H$_{46}$NO$_6$ 444.3320, found 444.3327.

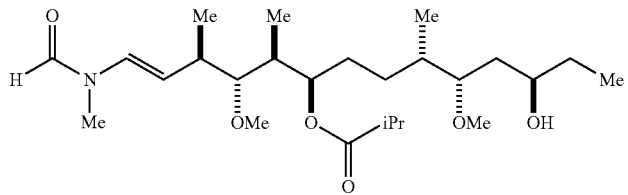

3

Color and State: Clear oil.
[α]$_D^{20}$ −38.4 (c = 0.46, CHCl$_3$).
$^1$H NMR (400 MHz, CDCl$_3$) δ 8.28 (s, 1H) *[8.05 (s, 1H)], 6.45 (d, J = 14.2 Hz, 1H) *[7.13 (d, J = 14.7 Hz, 1H)], 5.18 (td, J = 6.8, 1.5 Hz, 1H) *[5.18 (td, J = 8.2, 1.7 Hz, 1H)], 5.10 (dd, J = 14.2, 9.2 Hz, 1H) *[5.13 (dd, J = 14.5, 9.6 Hz, 1H)], 3.75-3.68 (m, 1H), 3.36 (s, 3H) *[3.44 (s, 3H)], 3.29 (ddd, J = 8.1, 4.9, 3.1 Hz, 1H), 3.01 (s, 3H) *[3.04 (s, 3H)], 2.80 (dd, J = 9.7, 2.0 Hz, 1H), 2.55 (septet, J = 7.0 Hz, 1H), 2.50-2.41 (m, 1H), 2.43 (d, J = 5.0 Hz, 1H) *[2.47 (d, J = 5.0 Hz, 1H)], 1.83-1.72 (m, 1H), 1.64-1.39 (m, 7H), 1.35-1.24 (m, 1H), 1.04-0.92 (m, 1H), 0.93 (t, J = 7.4 Hz, 3H), 0.89 (d, J = 6.8 Hz, 3H) *[0.88 (d, J = 6.8 Hz, 3H)], 0.85 (d, J = 7.0 Hz, 3H) *[0.84 (d, J = 7.0 Hz, 3H)], 1.18 (d, J = 6.9 Hz, 3H), 1.18 (d, J = 7.0 Hz, 3H) *[1.18 (d, J = 7.2 Hz, 3H)], 1.16 (d, J = 7.0 Hz, 3H).
$^{13}$C NMR (100 MHz, CDCl$_3$) δ 176.74 (e) *(176.77), 162.28 (o) *(160.96), 128.68 (o) *(124.69), 111.84 (o) *(113.58), 86.63 (o) *(86.69), 82.99 (o), 73.08 (o) *(73.13), 70.57 (o) *(70.63), 61.90 (o) *(61.97), 57.70 (o) *(57.64), 39.75 (o), 37.90 (o) *(38.22), 35.97 (e) *(35.86), 34.86 (o) *(34.79), 34.58 (o), 30.72 (e) *(30.66), 30.57 (e) *(30.42), 27.69 (o) *(33.22), 27.47 (e) *(27.34), 20.23 (o) *(20.41), 19.32 (o), 19.24 (o), 15.74 (o), 10.20 (o) *(10.22), 9.95 (o) *(9.80).
IR (neat) 3449 (w, br.), 2964 (m), 2928 (m), 2874 (w), 2820 (w), 1724 (m), 1689 (m), 1653 (vs), 1159 (m), 1089 (s), 1069 (s) cm$^{-1}$.
HRMS (ESI, [M + H]$^+$) calcd for C$_{25}$H$_{48}$NO$_6$ 458.3476, found 458.3489.

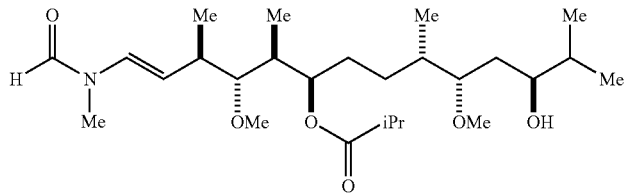

4

Color and State: Clear oil.
$^1$H NMR (400 MHz, CDCl$_3$) δ 8.27 (s, 1H) *[8.05 (s, 1H)], 6.45 (d, J = 14.2 Hz, 1H), *[7.13 (d, J = 14.6 Hz, 1H)], 5.17 (t, J = 6.7 Hz, 1H) *[5.18 (t, J = 6.6 Hz, 1H)], 5.10 (dd, J = 14.3, 9.2 Hz 1H) *[5.13 (dd, J = 14.7, 9.1 Hz, 1H)], 3.56-3.49 (m, 1H), 3.43 (s, 3H), 3.36 (s, 3H), 3.28 (dt, J = 7.8, 4.1 Hz, 1H), 3.00 (s, 3H) *[3.04 (s, 3H)], 2.80 (dd, J = 9.6, 2.3 Hz, 1H), 2.55 (septet, J = 7.1 Hz, 1H), 2.50-2.40 (m, 1H), 2.32 (d, J = 4.9 Hz, 1H), *[2.36 (d, J = 5.0 Hz, 1H)], 1.83-1.73 (m, 1H), 1.61 (septet, J = 6.7 Hz, 1H), 1.59-1.54 (m, 2H), 1.46-1.38 (m, 1H), 1.35-1.25 (m, 1H), 1.18 (d, J = 7.1 Hz, 3H) *[1.19 (d, J = 6.8 Hz, 3H)], 1.18 (d, J = 6.4 Hz, 3H), 1.16 (d, J = 7.1 Hz, 3H), 1.07-0.97 (m, 1H), 0.93 (d, TABLE 2-continued Structure and Characterization Data J = 6.7 Hz, 3H), 0.89 (d, 1 = 6.4 Hz, 6H) *[0.90 (d, J = 6.4 Hz, 6H)], 0.85 (d, J = 6.9 Hz, 3H) *[0.84 (d, J = 6.9 Hz, 3H)].
IR (neat) 3496 (w, br.), 2961 (m), 2932 (m), 2874 (w), 2829 (w), 1724 (m), 1689 (m), 1653 (vs), 1159 (m), 1090 (s), 1069 (s) cm$^{-1}$.

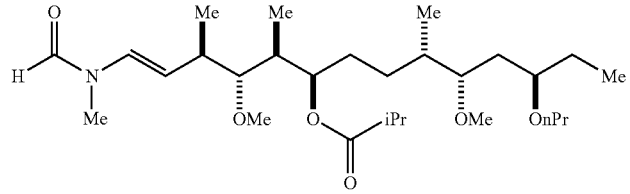

5

Color and State: Clear oil.
$[\alpha]_D^{22}$ −25.8 (c = 0.39, CHCl$_3$).
$^1$H NMR (400 MHz, CDCl$_3$) δ 8.27 (s, 1H) *[8.05 (s, 1H)], 6.45 (d, J = 14.2 Hz, 1H) *[6.45 (d, J = 14.7 Hz, 1H)], 5.18 (td, J = 6.7, 1. 7 Hz, 1H) *[5.17 (t, J = 6.9 Hz, 1H)], 5.10 (dd, J = 14.2, 9.2 Hz, 1H) *[5.11 (dd, J = 14.5, 9.9 Hz, 1H)], 3.48 (dt, J = 9.0, 6.5 Hz, 1H), 3.43 (s, 3H), 3.37 (dd, J = 5.8, 3.5 Hz, 1H), 3.33 (s, 3H) *[3.33 (s, 3H)], 3.30-3.24 (m, 1H), 3.27 (td, J = 9.2, 4.2 Hz, 1H) 3.00 (s, 3H) *[3.04 (s, 3H)], 2.80 (dd, J = 9.5, 2.5 Hz, 1H) *[2.79 (dd, J = 9.6, 2.5 Hz, 1H)], 2.54 (septet, J = 7.1 Hz, 1H), 2.50-2.39 (m, 1H), 1.75-1.66 (m, 1H), 1.64-1.37 (m, 10H), 1.18 (d, J = 7.1 Hz, 3H) *[1.18 (d, J = 7.0 Hz, 3H)], 1.18 (d, J = 7.0 Hz, 3H) *[1.17 (d, J = 7.0 Hz, 3H)], 1.16 (d, J = 7.4 Hz, 3H) *[1.16 (d, J = 7.4 Hz, 3H)], 1.04-0.96 (m, 1H), 0.93 (t, J = 7.4 Hz, 3H), 0.87 (t, J = 7.4 Hz, 3H), 0.86 (d, J = 6.4 Hz, 3H) *[0.85 (d, J = 7.0 Hz, 3H)], 0.84 (d, J = 6.7 Hz, 3H) *[0.83 (d, J = 7.1 Hz, 3H].
$^{13}$C NMR (100 MHz, CDCl$_3$) δ 176.76 (e) *(176.80), 162.31 (o) *(160.97), 128.68 (o) *(124.69), 111.93 (o) *(113.68), 86.66 (o) *(86.70), 81.85 (o), 77.30 (o), 73.23 (o) *(73.30), 70.86 (e), 61.91 (o) *(61.99), 57.94 (o) *(57.92), 39.58 (o) *(39.69), 37.91 (o) *(38.25), 35.77 (e) *(35.75), 35.29 (o) *(35.31), 34.62 (o), 30.68 (e), 27.71 (o) *(33.24), 27.63 (e) *(27.59), 27.07 (e), 23.62 (e), 20.27 (o) *(20.43), 19.35 (o), 19.27 (o), 15.36 (o), 11.05 (o), 9.95 (o) *(9.78), 9.43 (o).
IR (neat) 2962 (m), 2928 (m), 2873 (m), 1726 (m), 1694 (m), 1655 (vs), 1192 (m), 1089 (s), 1069 (s) cm$^{-1}$.
HRMS (ESI, [M + H]$^+$) calcd for C$_{28}$H$_{54}$NO$_6$ 500.3946, found 500.3925.

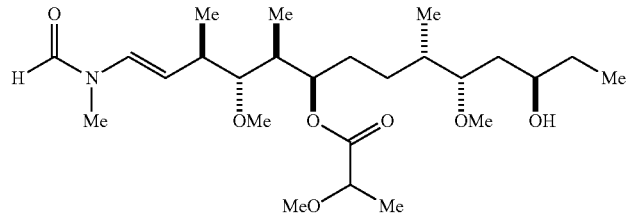

6

$^1$H NMR (400 MHz, CDCl$_3$) δ 8.27 (s, 1H), *[8.05 (s, 1H)], 6.46 (d, J = 14.1 Hz, 1H) *[7.13 (d, J = 14.7 Hz, 1H)], 5.31 (t, J = 6.8 Hz, 1H), 5.09 (dd, J = 14.1, 9.3 Hz, 1H) *[5.12 (dd, J = 15.4, 10.0 Hz, 1H)], 3.86 (q, J = 6.8 Hz, 1H), 3.74-3.67 (m, 1H), 3.45 (s, 3H), 3.41 (s, 3H), 3.36 (s, 3H), 3.30 (ddd, J = 8.4, 4.6, 3.5 Hz, 1H), 3.00 (s, 3H) *[3.04 (s, 3H)], 2.77 (dd, J = 9.6, 2.3 Hz, 1H) *[2.76 (dd, J = 9.7, 2.2 Hz, 1H)], 2.51-2.40 (m, 1H), 2.36 (d, J = 5.1 Hz, 1H) *[2.40 (d, J = 5.2 Hz, 1H)], 1.83-1.74 (m, 1H), 1.67-1.51 (m, 4H), 1.49-1.41 (m, 3H), 1.42 (d, J = 6.8 Hz, 3H), 1.33-1.22 (m, 1H), 1.15 (d, J = 6.9 Hz, 3H), 1.05-0.97 (m, 1H), 0.93 (t, J = 7.4 Hz, 3H), 0.89 (d, J = 6.8 Hz, 3H) *[0.88 (d, J = 7.0 Hz, 3H)], 0.86 (d, J = 7.1 Hz, 3H) *[0.85 (d, J = 6.9 Hz, 3H)].

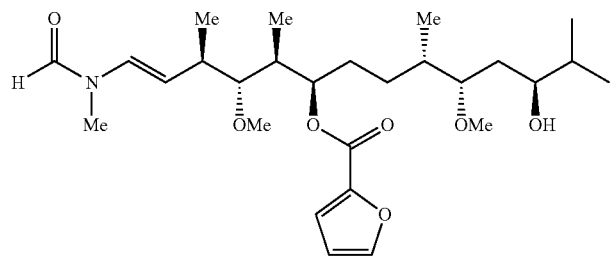

MA-02-054

$[\alpha]_D^{20}$ −3.8 (c = 0.35, CHCl$_3$).
$^1$H NMR (500 MHz, CDCl$_3$) δ 8.27 (s, 0.6H) *[8.05 (s, 0.4H)], 7.58 (dd, J= 1.7, 0.7 Hz, 1H), 7.14 (dd, J = 3.8, 1.0 Hz, 1H), *[7.14 (d, J= 14.2 Hz, 0.4H)], 6.51 (dd, J = 3.2, 1.7 Hz, 1H), 6.45 (d, J = 14.0 Hz, 0.6H), 5.42 (td, J = 8.0, 1.5 Hz, 0.6H) *[5.40 (td, J = 8.0, 1.5 Hz, 0.4H)], *[5.14 (dd, J = 14.5, 9.5 Hz 0.4H)], 5.11 (dd, J = 14.0, 9.0 Hz 0.6H), 3.53-3.48 (m, 1H), 3.45 (s, 2H), *[3.45 (s, 1H)], *[3.35 (s, 1H)], 3.35 (s, 2H), 3.29-3.24 (m, 1H), *[3.04 (s, 1H)], 3.01 (s, 2H), 2.80 (app. dt, J = 9.5, 2.5 Hz, 1H), 2.52-2.42 (m, 1H), 2.38 (dd, J = 15.2, 4.0 Hz, 1H), 1.82-1.54 (m, 6H), 1.55-1.44 (m, 3H), 1.15 (d, J = 7.0 Hz, 2H) *[1.15 (d, J = 7.0 Hz, 1H)], 1.09-0.98 (m, 1H), 0.94 (d, J = 7.0 Hz, 2H) *[0.93 (d, J = 7.0 Hz, 1H)], 0.91 (d, J = 7.0 Hz, 2H) *[0.90 (d, J = 7.0 Hz, 1H)], 0.89 (d, J = 6.5 Hz, 2H) *[0.89 (d, J = 6.5 Hz, 1H)], 0.84 (d, J = 7.0 Hz, 3H).

TABLE 2-continued

Structure and Characterization Data $^{13}$C NMR (125 MHz, CDCl$_3$) δ 162.15, *(160.84), *(158.58), 158.55, 146.26, 145.05, 128.61, *(124.64), 117.52, 113.46, 111.75, *(111.73), *(86.50), 86.44, 83.23, *(83.20), *(74.49), 74.44, *(73.83), 73.76, *(61.99), 61.88, 57.82, *(57.77), 39.92, *(38.22), 37.86, 35.03, *(34.97), 33.95, *(33.92), 33.27, *(33.22), 33.10, 30.62, *(30.46), 27.70, 27.59, *(27.57), *(20.28), 20.11, *(18.62), 18.60, *(17.81), 17.74, 15.65, 9.94, *(9.84).
IR (neat) 3480 (w, br.), 2957 (m), 29257 (m), 2873 (w), 2831 (w), 1688 (m), 1652 (vs), 1471 (m), 1295 (s), 1179 (m), 1118 (s), 1088 (s), 1073 (s), 938 (m), 762 (m), 728 (m) cm$^{-1}$.
HRMS (ESI, [M + H]$^+$) calcd for C$_{27}$H$_{45}$O$_7$NNa 518.3088, found 518.3085.

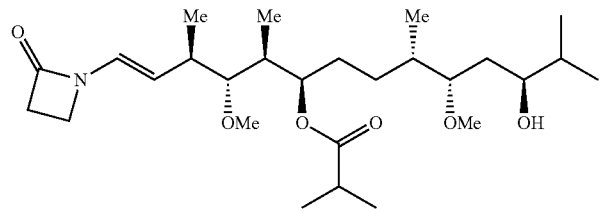

MA-02-043

$[α]_D^{20}$ −38.2 (c = 0.8, CHCl$_3$).
$^1$H NMR (500 MHz, CDCl$_3$) δ 6.53 (d, J = 14.5 Hz, 1H), 5.16 (td, J = 7.0, 1.5 Hz, 1H), 4.98 (dd, J = 14.5, 9.5 Hz, 1H), 3.57-3.49 (m, 1H), 3.41 (s, 3H), 3.38 (t, J = 4.5 Hz, 2H), 3.36 (s, 3H), 3.30-3.27 (m, 1H), 2.96 (t, J = 4.5 Hz, 2H), 2.76 (dd, J = 10.0, 2.0 Hz, 1H), 2.54 (septet, J = 7.5 Hz, 1H), 2.43-2.38 (m, 1H), 2.36 (d, J = 5.0 Hz, 1H), 1.82-1.75 (m, 1H), 1.65-1.48 (m, 6H), 1.48-1.39 (m, 1H), 1.17 (d, J = 7.0 Hz, 3H), 1.17 (d, J = 7.0 Hz, 3H), 1.12 (d, J = 7.0 Hz, 3H), 1.10-0.95 (m, 1H), 0.94 (d, J = 6.5 Hz, 3H), 0.90 (d, J = 6.5 Hz, 3H), 0.88 (d, J = 6.5 Hz, 3H), 0.82 (d, J = 7.0 Hz, 3H).
$^{13}$C NMR (125 MHz, CDCl$_3$) δ 176.62, 163.82, 122.01, 111.75, 86.55, 83.03, 73.86, 73.03, 61.82, 57.68, 39.65, 38.20, 37.24, 35.93, 34.89, 34.47, 33.95, 30.34, 27.40, 19.93, 19.21, 19.11, 18.74, 17.84, 15.63, 9.76.
IR (neat) 3479 (w, br.), 2961 (m), 2932 (m), 2875 (w), 1727 (vs), 1658 (w), 1463 (w), 1396 (m), 1339 (m), 1090 (vs), 1026 (s), 943 (m), 731 (s) cm$^{-1}$.

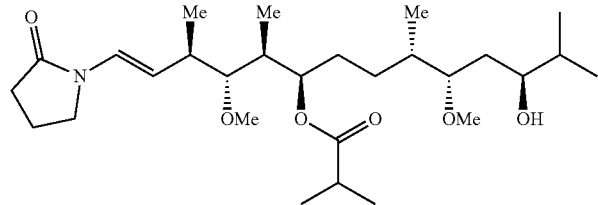

MA-02-041

$[α]_D^{20}$ −54.7 (c = 0.7, CHCl$_3$).
$^1$H NMR (500 MHz, CDCl$_3$) δ 6.87 (d, J = 14.5 Hz, 1H), 5.16 (td, J = 7.0, 1.5 Hz, 1H), 4.93 (dd, J = 14.7, 9.2 Hz, 1H), 3.55-3.49 (m, 1H), 3.49 (t, J = 6.7 Hz, 2H), 3.41 (s, 3H), 3.35 (s, 3H), 3.30-3.27 (app. quin., J = 3.5 Hz, 1H), 2.77 (dd, J = 9.7, 1.7 Hz, 1H), 2.55 (septet, J = 7.0 Hz, 1H), 2.46 (t, J = 8.0 Hz, 2H), 2.45-2.40 (m, 1H), 2.37 (d, J = 5.0 Hz, 1H), 2.07 (quin., J = 8.0 Hz, 2H), 1.82-1.73 (m, 1H), 1.65-1.47 (m, 6H), 1.46-1.38 (m, 1H), 1.17 (d, J = 7.0 Hz, 3H), 1.16 (d, J = 7.0 Hz, 3H), 1.14 (d, J = 7.0 Hz, 3H), 1.00-0.95 (m, 1H), 0.93 (d, J = 6.5 Hz, 3H), 0.88 (d, J = 7.0 Hz, 3H), 0.88 (d, J = 6.5 Hz, 3H), 0.83 (d, J = 7.0 Hz, 3H).
$^{13}$C NMR (125 MHz, CDCl$_3$) δ 176.64, 172.93, 123.95, 112.58, 86.65, 83.01, 73.86, 73.10, 61.82, 57.66, 45.33, 39.67, 37.94, 34.88, 34.47, 33.94, 33.39, 31.32, 30.31, 27.37, 20.33, 19.21, 19.11, 18.73, 17.84, 17.38, 15.61, 9.73.
IR (neat) 3490 (w, br), 2961 (m), 2931 (m), 2875 (w), 1724 (s), 1702 (s), 1686 (vs), 1657 (s), 1462 (w), 1409 (m), 1365 (w), 1272 (m), 1193 (m), 1159 (m), 1091 (vs), 960 (m), 911 (w), 731 (m) cm$^{-1}$.
HRMS (ESI, [M + H]$^+$) calcd for C$_{28}$H$_{52}$O$_6$N 498.3789, found 498.3808.

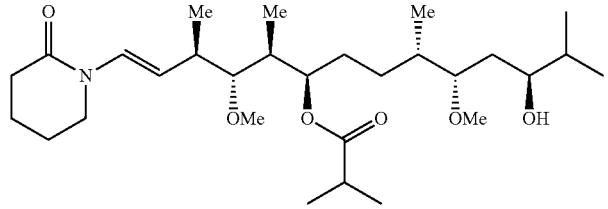

MA-02-042

$[α]_D^{20}$ −41.9 (c = 0.4, CHCl$_3$).
$^1$H NMR (500 MHz, CDCl$_3$) δ 7.39 (d, J = 15.0 Hz, 1H), 5.16 (td, J = 7.0, 1.5 Hz, 1H), 5.00 (dd, J = 14.5, 9.2 Hz, 1H), 3.55-3.49 (m, 1H), 3.42 (s, 3H), 3.40 (t, J = 6.2 Hz, 2H), 3.35 (s, 3H), 3.31-3.25 (m, 1H), 2.78 (dd, J = 10.0, 2.0 Hz, 1H), 2.55 (septet, J = 7.0 Hz, 1H), 2.50-2.42 (m, 1H), 2.46 (t, J = 6.5 Hz, 2H), 2.35 (d, J = 5.0 Hz, 1H), 1.89-1.82 (m, 2H), 1.81-1.73 (m, 3H), 1.65-1.60 (m, 1H), 1.58-1.38 (m, 6H), 1.17 (d, J = 7.0 Hz, 3H), 1.17 (d, J = 7.0 Hz, 3H), 1.14 (d, J = 7.0 Hz, 3H), 1.02-0.95 (m, 1H), 0.93 (d, J = 6.5 Hz, 3H), 0.88 (d, J = 7.0 Hz, 3H), 0.88 (d, J = 6.5 Hz, 3H), 0.84 (d, J = 7.0 Hz, 3H).
$^{13}$C NMR (125 MHz, CDCl$_3$) δ 176.67, 168.29, 127.01, 111.56, 86.75, 83.02, 73.88, 73.17, 61.85, 57.68, 45.19, 39.70, 38.23, 34.91, 34.48, 33.94, 33.40, 32.93, 30.33, 27.39, 22.60, 20.58, 19.22, 19.13, 18.76, 17.85, 15.61, 9.70.

IR (neat) 3416 (w, br.), 2954 (m), 2932 (m), 2873 (w), 1725 (s), 1636 (vs), 1460 (w), 1382 (m), 1263 (m), 1193 (w), 1161 (s), 1085 (vs), 964 (m), 731 (w) cm$^{-1}$.
HRMS (ESI, [M + H]$^+$) calcd for $C_{29}H_{54}O_6N$ 512.3945, found 512.3949.

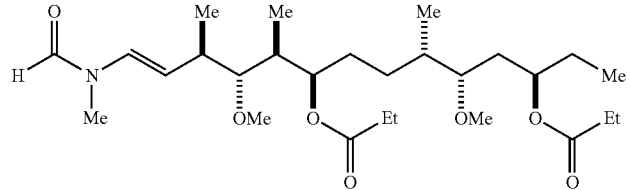

7

Color and State: Clear oil.
$[\alpha]_D^{23}$ −16.9 (c = 0.50, CHCl$_3$).
$^1$H NMR (400 MHz, CDCl$_3$) δ 8.27 (s, 1H) *[8.05 (s, 1H)], 6.45 (d, J = 14.1 Hz, 1H) *[7.12 (d, J = 14.7 Hz, 1H)], 5.19 (td, J = 6.9, 1.6 Hz, 1H) *[5.19 (td, J = 7.2, 1.6 Hz, 1H)], 5.10 (dd, J = 14.2, 9.3 Hz, 1H) *[5.12 (dd, J = 14.5, 9.9 Hz, 1H)], 3.44 (s, 3H) *[3.44 (s, 3H)], 3.29 (s, 3H), 3.00 (s, 3H) *[3.04 (s, 3H)], 2.96 (dt, J = 8.5, 3.7 Hz, 1H), 2.81 (dd, J = 9.7, 2.2 Hz, 1H), 2.52-2.40 (m, 1H), 2.33 (q, J = 7.4 Hz, 2H), 2.32 (q, J = 7.6 Hz, 2H), 1.74-1.65 (m, 1H), 1.63-1.49 (m, 6H), 1.48-1.39 (m, 1H), 1.16 (t, J = 7.6 Hz, 3H), 1.16 (d, J = 7.4 Hz, 3H), 1.15 (t, J = 7.5 Hz, 3H), 1.04-0.92 (m, 1H), 0.87 (t, J = 7.6 Hz, 3H), 0.85 (d, J = 6.8 Hz, 3H) *[0.84 (d, J = 7.2 Hz, 3H)], 0.84 (d, J = 6.9 Hz, 3H) *[0.83 (d, J = 7.1 Hz, 3H)].
$^{13}$C NMR (100 MHz, CDCl$_3$) δ 174.35 (e), 174.25 (e) *(174.29), 162.30 (o) *(160.97), 128.70 (o) *(124.71), 111.89 (o) *(113.67), 86.65 (o) *(86.70), 81.94 (o) *(81.90), 73.44 (o) *(73.49), 72.83 (o) *(72.80), 61.92 (o) *(61.98), 58.15 (o), 39.60 (o), 37.95 (o) *(38.28), 35.30 (e) *(35.27), 35.19 (o) *(35.11), 30.75 (e), 30.60 (e), 28.19 (e), 28.12 (e) *(28.09), 27.70 (o) *(33.23), 27.47 (e) *(27.35), 20.24 (o) *(20.42), 15.44 (o) *(15.42), 9.96 (o), 9.91 (o), 9.65 (o), 9.56 (o).
IR (neat) 2967 (m), 2930 (m), 2877 (w), 2829 (w), 1728 (s), 1691 (s), 1654 (vs), 1187 (s), 1091 (s), 1065 (s) cm$^{-1}$.
HRMS (ESI, [M + H]$^+$) calcd for $C_{27}H_{50}NO_7$ 500.3582, found 500.3605

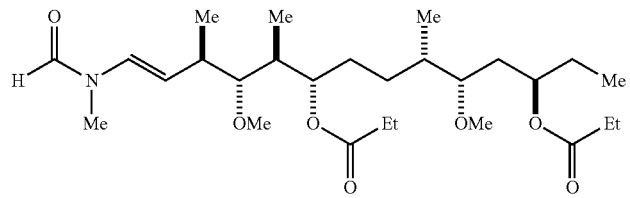

8

Color and State: Clear oil.
$[\alpha]_D^{22}$ −41.5 (c = 0.26, CHCl$_3$).
$^1$H NMR (400 MHz, CDCl$_3$) δ 8.27 (s, 1H) *[8.04 (s, 1H)], 6.44 (d, J = 14.1 Hz, 1H) *[7.10 (d, J = 14.7 Hz, 1H)], 5.14 (dd, J = 16.0, 9.3 Hz, 1H) *[5.18 (dd, J = 16.6, 9.1 Hz, 1H)], 5.09 (dt, J = 8.5, 4.4 Hz, 1H) *[5.13-5.07 (m, 1H)], 5.01 (dddd, J = 10.2, 8.3, 6.1, 4.1 Hz, 1H), 3.42 (s, 3H) *[3.44 (s, 3H)], 3.29 (s, 3H), 3.01 (s, 3H) *[3.04 (s, 3H)], 2.97 (dd, J = 8.2, 3.9 Hz, 1H) *[3.02-3.00 (m, 1H)], 2.90 (dd, J = 7.4, 3.7 Hz, 1H) *[2.88 (dd, J = 5.1, 3.5 Hz, 1H)], 2.51-2.37 (m, 1H), 2.33 (q, J = 7.6 Hz, 2H) *[2.32 (q, J = 7.5 Hz, 2H)], 2.32 (q, J = 7.7 Hz, 2H) *[2.32 (q, J = 7.4 Hz, 2H)], 1.97 (app. quintet of d, J = 7.1, 4.8 Hz, 1H) *[1.92 (app. quintet of d, J = 7.9, 4.2 Hz, 1H)], 1.75-1.66 (m, 1H), 1.62-1.42 (m, 1H), 1.37-1.25 (m, 1H), 1.15 (t, J = 7.7 Hz, 3H), *[1.14 (t, J = 7.5 Hz, 3H)], 1.14 (d, J = 6.8 Hz, 3H) *[1.14 (d, J = 6.3 Hz, 3H)], 1.14 (d, J = 7.1 Hz, 3H) *[1.13 (d, J = 7.8 Hz, 3H)], 1.10-1.01 (m, 1H), 0.88 (t, J = 7.4 Hz, 3H), 0.85 (d, J = 6.9 Hz, 3H), 0.85 (d, J = 6.9 Hz, 3H) *[0.82 (d, J = 7.1 Hz, 3H)]
$^{13}$C NMR (100 MHz, CDCl$_3$) δ 174.34 (e), 174.07 (e) *(174.03), 162.32 (o) *(160.97), 128.40 (o) *(124.48), 113.07 (o) *(114.56), 87.29 (o) *(87.43), 82.02 (o) *(81.98), 74.64 (o) *(74.72), 72.85 (o), 60.78 (o), *(60.93), 58.16 (o), 39.44 (o) *(39.75), 37.92 (o) *(38.13), 35.39 (e), 35.04 (o), 28.13 (e), 28.09 (e), 28.08 (e), 27.98 (e) *(27.84), 27.72 (o) *(33.28), 27.66 (e) *(27.60), 19.97 (o) *(20.05), 15.39 (o) *(15.42), 11.77 (o) *(11.56), 9.66 (o), 9.58 (o), 9.50 (o).
IR (neat) 2969 (m), 2931 (m), 2880 (w), 2828 (w), 1729 (s), 1692 (s), 1656 (vs), 1187 (s), 1093 (s), 1074 (s) cm$^{-1}$.
HRMS (ESI, [M + H]$^+$) calcd for $C_{27}H_{50}NO_7$ 500.3582, found 500.3564.

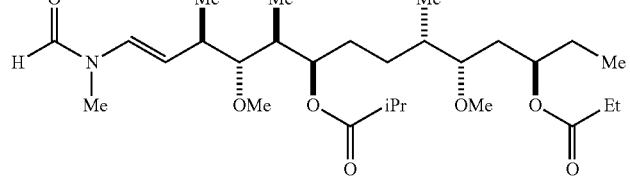

9

Color and State: Clear oil.
$[\alpha]_D^{22}$ −35.8 (c = 0.29, CHCl$_3$).
$^1$H NMR (400 MHz, CDCl$_3$) δ 8.28 (s, 1H) *[8.05 (s, 1H)], 6.45 (d, J = 14.2 Hz, 1H) *[7.13 (d, J = 14.7 Hz, 1H)], 5.18

(td, J = 7.0, 1.0 Hz, 1H) *[5.19 (m, 1H)], 5.10 (dd, J = 13.8, 9.2 Hz, 1H) *[5.13 (dd, J = 14.6, 9.7 Hz, 1H)], 5.00 (ddt, J = 8.9, 6.2, 3.2 Hz, 1H), 3.42 (s, 3H), 3.29 (s, 3H), 3.00 (s, 3H) *[3.04 (s, 3H)], 2.96 (dt, J = 8.7, 3.5 Hz, 1H), 2.80 (dd, J = 9.6, 2.2 Hz, 1H), 2.55 (septet, J = 7.0 Hz, 1H), 2.50-2.40 (m, 1H), 2.32 (q, J = 7.5 Hz, 2H), 1.72-1.60 (m, 1H), 1.59-1.40 (m, 6H), 1.35-1.23 (m, 1H), 1.18 (d, J = 6.6 Hz, 3H), 1.18 (d, J = 7.4 Hz, 1H), 1.16 (d, J = 7.8 Hz, 3H), 1.15 (t, J = 7.8 Hz, 3H), 1.03-0.92 (m, 1H), 0.89-0.79 (m, 1H), 0.87 (t, J = 7.3 Hz, 3H), 0.84 (d, J = 6.4 Hz, 3H), 0.84 (d, J = 7.0 Hz, 3H).
$^{13}$C NMR (100 MHz, CDCl$_3$) δ 176.79 (e) *(176.82), 174.35 (e), 162.30 (o) *(160.98), 128.71 (o) *(124.72), 111.88 (o) *(113.65), 86.67 (o) *(86.72), 81.93 (u) *(81.90), 73.15 (o) *(73.19), 72.84 (o) *(72.81), 61.92 (o) *(62.00), 58.14 (o), 39.73 (o) *(38.26), 37.93 (o) *(38.26), 35.35 (e) *(35.31), 35.23 (o) *(35.16), 34.62 (o), 30.78 (e), *(30.62), 28.12 (e), 28.09 (e), 27.71 (o) *(33.22), 27.50 (e) *(27.39), 20.25 (o) *(20.43), 19.35 (o), 19.27 (o), 15.44 (o) *(15.42), 9.96 (o) *(9.81), 9.64 (o), 9.57 (o).
IR (neat) 2967 (m), 2928 (m), 2876 (w), 2828 (w), 1726 (s), 1692 (m), 1655 (vs), 1190 (s), 1091 (s), 1066 (s) cm$^{-1}$.
HRMS (ESI, [M + H]$^+$) calcd for C$_{28}$H$_{52}$NO$_7$ 514.3738, found 514.3717.

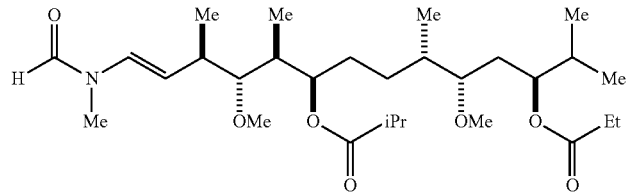

10

Color and State: Clear oil.
[α]$_D^{22}$ −28.3 (c = 0.13, CHCl$_3$).
$^1$H NMR (400 MHz, CDCl$_3$) δ 8.27 (s, 1H) *[8.05 (s, 1H)], 6.45 (d, J = 14.1 Hz, 1H) *[7.13 (d, J = 14.7 Hz, 1H)], 5.18 (td, J = 6.7, 1.5 Hz, 1H) *[5.18 (td, J = 6.3, 1.3 Hz, 1H)], 5.10 (dd, J = 14.2, 9.3 Hz, 1H) *[5.13 (dd, J = 14.6, 9.8 Hz, 1H)], 4.97 (dt, J = 8.4, 4.3 Hz, 1H), 3.44 (s, 3H), 3.29 (s, 3H), 3.00 (s, 3H) *[3.04 (s, 3H)], 2.90 (dt, J = 8.0 4.0 Hz, 1H), 2.79 (dd, J = 9.9, 1.9 Hz, 1H) *[2.80 (dd, J = 9.6, 2.2 Hz, 1H)], 2.56 (septet, J = 6.9 Hz, 1H), 2.50-2.40 (m, 1H), 2.33 (q, J = 7.6 Hz, 2H), 1.80 (app. quintet of d, J = 6.8, 5.3 Hz, 1H), 1.73-1.65 (m, 1H), 1.62-1.52 (m, 1H), 1.50-1.40 (m, 3H), 1.19-1.14 (m, 1H), 1.18 (d, J = 7.2 Hz, 3H), 1.18 (d, J = 7.2 Hz, 3H) *[1.16 (d, J = 7.4 Hz, 3H)], 1.16 (t, J = 7.3 Hz, 3H), 1.04-0.92 (m, 1H), 0.88 (d, J = 6.8 Hz, 3H), 0.88 (d, J = 6.8 Hz, 3H), 0.85 (d, J = 6.9 Hz, 3H) *[0.84 (d, J = 6.9 Hz, 3H)]
$^{13}$C NMR (100 MHz, CDCl$_3$) δ 176.79 (e) *(176.82), 174.34 (e), 162.29 (o) *(160.97), 128.71 (o) *(124.71), 111.88 (o) *(113.65), 86.67 (o) *(86.72), 82.00 (o) *(81.97), 75.49 (o) *(75.47), 73.14 (o) *(73.18), 61.92 (o) *(62.00), 58.19 (o) *(58.18), 39.76 (o) *(39.74), 37.94 (o) *(38.26), 35.26 (o) *(35.18), 34.62 (o), 32.63 (e) *(32.57), 32.34 (o), 30.81 (e) *(30.63), 28.10 (e), 27.70 (o) *(33.22), 27.50 (e) *(27.38), 20.25 (o) *(20.42), 19.36 (o), 19.28 (o), 18.51 (o), 17.61 (o) *(17.65), 15.55 (o) *(15.52), 9.98 (o) *(9.81), 9.65 (o).
IR (neat) 2966 (m), 2933 (m), 2876 (w), 2829 (w), 1726 (s), 1693 (s), 1655 (vs), 1190 (s), 1091 (s), 1066 (s) cm$^{-1}$.

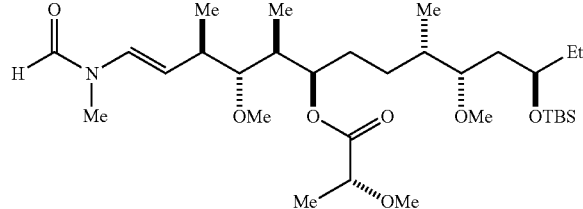 [SMILES: CC[C@H](C[C@H](OC)[C@@H](C)CC[C@@H](OC(=O)[C@@H](C)OC)[C@H](C)[C@H](OC)[C@H](C)/C=C/N(C)C=O)O[Si](C)(C)C(C)(C)C]

Color and State: White solid.
$^1$H NMR (400 MHz, CDCl$_3$) δ 8.27 (s, 1H) *[8.05 (s, 1H)], 6.45 (d, J = 14.1 Hz, 1H), *[7.13 (d, J = 14.7 Hz, 1H)], 5.32 (t, J = 7.7 Hz, 1H) *[5.32 (t, J = 6.2 Hz, 1H)], 5.09 (dd, J = 14.1, 9.1 Hz, 1H) *[5.12 (dd, J = 14.7, 9.5 Hz, 1H)], 3.87 (q, J = 6.8 Hz, 1H), 3.76 (dt, J = 11.5, 5.7 Hz, 1H), 3.45 (s, 3H) *[3.45 (s, 3H)], 3.41 (s, 3H), 3.30 (s, 3H), 3.21 (dtd, J = 7.9, 6.3, 3.1 Hz, 1H), 3.00 (s, 3H), *[3.04 (s, 3H)], 2.77 (dd, J = 9.5, 2.6 Hz, 1H) *[2.76 (dd, J = 9.6, 2.9 Hz, 1H)], 2.52 (m, 1H), 1.67 (m, 3H), 1.77 (dqt, J = 10.6, 7.2, 3.5 Hz, 1H), 1.50-1.41 (m, 3H), 1.42 (d, J = 6.8 Hz, 3H), 1.36 (app. t, J = 6.0 Hz, 2H), 1.15 (d, J = 7.0 Hz, 3H), 1.04-0.94 (m, 1H), 0.88 (s, 9H), 0.86 (d, J = 6.7 Hz, 3H), 0.84 (t, J = 7.4 Hz, 3H), 0.84 (d, J = 6.9 Hz, 3H), 0.05 (s, 6H).

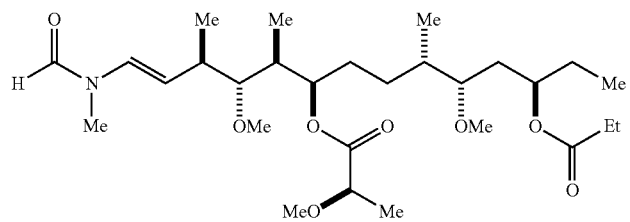

11

Color and State: Clear oil.

[α]$_D^{23}$ −7.7 (c = 0.15, CHCl$_3$).

$^1$H NMR (400 MHz, CDCl$_3$) δ 8.28 (s, 1H) *[8.05 (s, 1H)], 6.46 (d, J = 14.2 Hz, 1H) *[7.13 (d, J = 14.7 Hz, 1H)], 5.31 (td, J = 6.9, 1.8 Hz, 1H) *[5.31 (td, J = 6.8, 1.6 Hz, 1H)], 5.09 (dd, J = 14.1, 9.2 Hz, 1H) *[5.12 (dd, J = 14.6, 9.5 Hz, 1H)], 5.00 (tdt, J = 9.0, 6.0, 3.3 Hz, 1H), 3.87 (q, J = 6.8 Hz, 1H) *[3.87 (q, J = 6.9 Hz, 1H)], 3.45 (s, 3H), 3.42 (s, 3H), 3.29 (s, 3H), 3.00 (s, 3H) *[3.04 (s, 3H)], 2.96 (dt, J = 9.0, 3.4 Hz, 1H), 2.77 (dd, J = 9.6, 2.5 Hz, 1H) *[2.76 (dd, J = 9.9, 2.1 Hz, 1H)], 2.52-2.40 (m, 1H), 2.32 (q, J = 7.6 Hz, 2H), 1.70 (dqt, J = 10.1, 6.8, 3.4 Hz, 1H), 1.65-1.47 (m, 7H), 1.42 (d, J = 6.8 Hz, 3H), 1.37-1.25 (m, 1H), 1.16 (d, J = 6.5 Hz, 3H), 1.15 (t, J = 7.4 Hz, 3H), 1.04-0.93 (m, 1H), 0.87 (t, J = 7.1 Hz, 3H), 0.85 (d, J = 6.8 Hz, 3H) *[0.85 (d, J= 7.1 Hz, 3H)], 0.84 (d, J = 6.9 Hz, 3H).

IR (neat) 2968 (m), 2929 (m), 2878 (w), 2827 (w), 1730 (s), 1691 (m), 1655 (vs), 1189 (s), 1090 (s), 1067 (s) cm$^{-1}$.

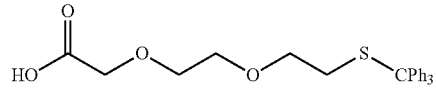

$^1$H NMR (400 MHz, CDCl$_3$) δ 7.44-7.41 (m, 6H), 7.30-7.26 (m, 6H), 7.23-7.19 (m, 3H), 4.13 (s, 2H), 3.68-3.66 (m, 2H), 3.47-3.45 (m, 2H), 3.27 (t, A$_2$ of A$_2$B$_2$, J$_{AB}$ = 6.8 Hz, 2H), 2.45 (t, B$_2$ of A$_2$B$_2$, J$_{AB}$ = 6.8 Hz, 2H).

$^{13}$C NMR (100 MHz, CDCl$_3$) δ 174.34 (e), 144.80 (e), 129.69 (o), 127.99 (o), 126.78 (o), 71.16 (e), 69.94 (e), 69.82 (e), 68.53 (e), 66.78 (e), 31.50 (e).

IR (neat) 3053 (w), 2968 (w), 2928 (w), 2896 (w), 2861 (w), 1721 (m), 1486 (w), 1440 (m), 1143 (m), 1120 (s), 1013 (m), 741 (s), 699 (vs), 676 (s) cm$^{-1}$.

HRMS (ESI, [M + Na]$^+$) calcd for C$_{25}$H$_{26}$O$_4$NaS 445.1444, found 445.1437.

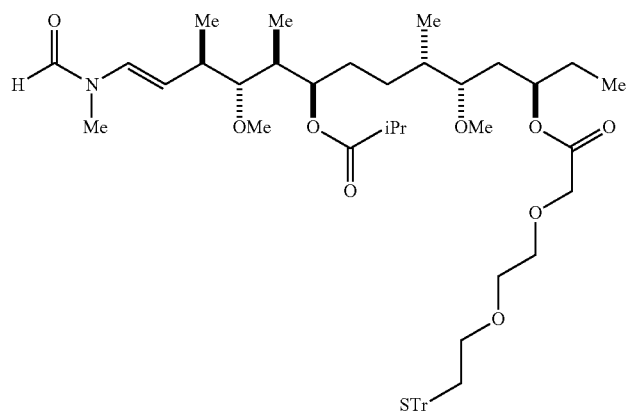

12

Color and State: Clear oil.

[α]$_D^{21}$ −11.3 (c = 0.13, CHCl$_3$). Tr means trityl.

$^1$H NMR (400 MHz, CDCl$_3$) δ 8.27 (s, 1H), *[8.04 (s, 1H)], 7.42-7.39 (m, 6H), 7.29-7.25 (m, 6H), 7.22-7.18 (m, 3H), 6.45 (d, J = 14.2 Hz, 1H) *[7.12 (d, J = 14.7 Hz, 1H)], 5.18 (td, J = 6.7, 1.3 Hz, 1H), *[5.17 (td, J = 8.2, 1.7 Hz, 1H)], 5.13-5.05 (m, 1H), 5.10 (dd, J = 14.1, 9.2 Hz, 1H) *[5.12 (dd, J = 14.2, 9.6 Hz, 1H)], 4.10 (s, 2H), 3.65 (dd, J = 5.7, 3.8 Hz, 2H), 3.50-3.48 (m, 2H), 3.43 (s, 3H) *[3.43 (s, 3H)], 3.30 (t, A of A$_2$B$_2$, J$_{AB}$ = 7.0 Hz, 2H), 3.27 (s, 3H), 3.00 (s, 3H) *[3.03 (s, 3H)], 2.55 (septet, J = 7.2 Hz, 1H), 2.50-2.39 (m, 1H), 2.43 (t, B$_2$ of A$_2$B$_2$, J$_{AB}$ = 7.0 Hz, 2H), 2.93 (dt, J = 8.4, 3.2 Hz, 1H), 2.79 (dd, J = 9.6, 1.9 Hz, 1H), 1.75-1.65 (m, 1H), 1.62-1.48 (m, 6H), 1.45-1.37 (m, 1H), 1.35-1.22 (m, 1H), 1.18 (d, J = 6.9 Hz, 3H) *[1.18 (d, J = 6.9 Hz, 3H)], 1.03-0.91 (m, 1H), 1.18 (d, J = 6.9 Hz, 3H) *[1.17 (d, J = 6.8 Hz, 3H)], 1.16 (d, J = 6.6 Hz, 3H), 0.86 (t, J = 7.3 Hz, 3H), 0.84 (d, J = 7.0 Hz, 3H) *[0.83 (d, J = 6.6 Hz, 3H)], 0.82 (d, J = 6.6 Hz, 3H) *[0.81 (d, J = 7.1 Hz, 3H)].

$^{13}$C NMR (100 MHz, CDCl$_3$) δ 144.96 (e), 176.77 (e) *(176.81), 170.34 (e), 162.28 (o) *(160.97), 129.76 (o), 128.70 (o) *(124.71), 128.02 (o), 126.79 (o), 111.84 (o) *(113.61), 86.64 (o) *(86.70), 81.81 (o), 73.84 (o) *(73.81), 73.11 (o) *(73.15), 70.87 (e), 70.30 (e), 69.81 (e), 68.78 (e), 66.75 (e), 61.92 (o) *(62.00), 58.03 (o), 39.76 (o), 37.93 (o) *(38.25), 35.03 (e) *(35.00), 34.84 (o) *(34.78), 34.61 (o), 31.74 (e), 30.83 (e) *(30.65), 28.09 (e), 27.70 (o) *(33.23), 27.21 (e) *(27.10), 20.25 (o) *(20.44), 19.36 (o), 19.28 (o), 15.54 (o) *(15.51), 9.97 (o), 9.70 (o) *(9.81).

IR (neat) 2966 (m), 2927 (m), 2873 (w), 1748 (m), 1724 (m), 1689 (m), 1654 (s), 1444 (m), 1198 (s), 1149 (s), 1091 (s), 1068 (s), 741 (s), 700 (vs) cm$^{-1}$.

HRMS (ESI, [M + H]$^+$) calcd for C$_{50}$H$_{72}$O$_9$NS 862.4922, found 862.4885.

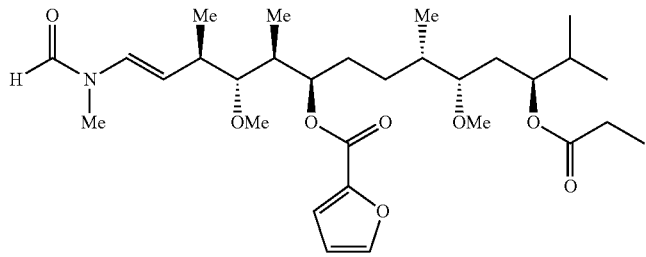

MA-02-058

$[\alpha]_D^{20}$ −1.2 (c = 0.3, CHCl$_3$).
$^1$H NMR (500 MHz, CDCl$_3$) δ 8.27 (s, 0.6H) *[8 05 (s, 0.4H)], 7.58 (dd, J = 1.5, 0.5 Hz, 1H), 7.14 (dd, J = 4.5, 1.0 Hz, 1H), *[7.13 (d, J = 14.5 Hz, 0.4H)], 6.51 (dd, J = 3.2, 1.7 Hz, 1H), 6.45 (d, J = 14.5 Hz, 0.6H), 5.42 (td, J = 7.0, 1.5 Hz, 0.6H) *[5.40 (td, J = 7.0, 1.5 Hz, 0.4H)], *[5.14 (dd, J = 14.5, 9.5 Hz 0.4H)], 5.11 (dd, J = 14.0, 9.0 Hz 0.6H), 4.96 (app. quintate of d, J = 4.5, 1.0 Hz, 1H), 3.45 (s, 2H), *[3.45 (s, 1H)], 3.28 (s, 3H), *[3.04 (s, 1H)], 3.00 (s, 2H), 2.91 (dd, J = 7.5, 4.2 Hz, 1H), 2.80 (app. dt, J = 9.5, 2.5 Hz, 1H), 2.53-2.41 (m, 1H), *[2.32 (q, J = 7.5 Hz, 0.7H)], 2.32 (q, J = 7.5 Hz, 1.3H), 1.82-1.1.75 (m, 1H), 1.75-1.69 (m, 2H), 1.68-1.60 (m, 2H), 1.55-1.45 (m, 3H), 1.15 (d, J = 7.5 Hz, 2H) *[1.15 (d, J = 7.0 Hz, 1H)], 1.13 (d, J = 7.5 Hz, 2H) *[1.13 (d, J = 7.5 Hz, 1H)], 1.08-0.99 (m, 1H), 0.93 (d, J = 7.0 Hz, 2H) *[0.93 (d, J = 7.0 Hz, 1H)], 0.86 (d, J = 6.5 Hz, 3H) 0.85 (t, J = 6.2 Hz, 3H), 0.85 (d, J = 6.5 Hz, 3H).
$^{13}$C NMR (125 MHz, CDCl$_3$) δ 174.16, 162.12 , *(160.81), *(158.56), 158.53, 146.22, 145.12, 128.60, *(124.63), 117.47, *(117.45), 113.51, 111.77, *(111.73), *(86.51), 86.45, 81.89, *(81.86), 75.35, *(75.33), *(74.51), 74.48, *(61.94), 61.82, 58.07, *(58.06), 39.76, *(39.74), *(38.21), 37.85, 35.10, *(35.02), 33.06, 32.50, *(32.44), 33.18, 30.72, *(30.53), 27.94, 27.56, 27.50 *(27.38), *(20.25), 20.07, 18.36, *(17.47), 17.43, 15.40, *(15.36), 9.91, *(9.79), 9.47.
IR (neat) 2964 (m), 2932 (m), 2876 (w), 2829 (w), 1723 (s), 1692 (s), 1655 (vs), 1472 (m), 1295 (s), 1180 (s), 1118 (s), 1090 (s), 1071 (s), 938 (m), 763 (m) cm$^{-1}$.
HRMS (ESI, [M + H]$^+$) calcd for C$_{30}$H$_{49}$O$_8$NNa 574.3350, found 574.3361.

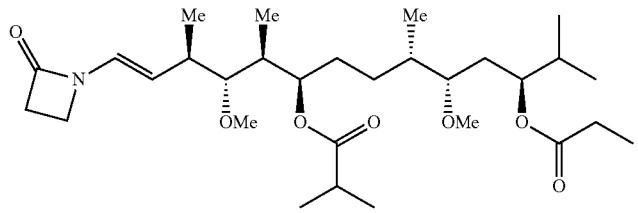

MA-02-047

$[\alpha]_D^{20}$ −44.9 (c = 0.5, CHCl$_3$).
$^1$H NMR (500 MHz, CDCl$_3$) δ 6.54 (d, J = 14.5 Hz, 1H), 5.16 (td, J = 7.0, 1.5 Hz, 1H), 4.98 (dd, J = 14.2, 9.2 Hz, 1H), 4.97 (t, J = 8.5 Hz, 1H), 3.41 (s, 3H), 3.37 (t, J = 4.5 Hz, 2H), 3.29 (s, 3H), 2.96 (t, J = 4.5 Hz, 2H), 2.90 (dt, J = 8.5, 3.2 Hz, 1H), 2.76 (dd, J = 10.0, 2.0 Hz, 1H), 2.54 (septet, J = 7.0 Hz, 1H), 2.43-2.36 (m, 1H), 2.34 (app. q, J = 7.5 Hz, 2H), 1.82-1.76 (m, 1H), 1.73-1.62 (m, 1H), 1.61-1.50 (m, 3H), 1.50-1.39 (m, 3H), 1.17 (d, J = 7.0 Hz, 3H), 1.17 (d, J = 7.0 Hz, 3H), 1.15 (t, J = 7.5 Hz, 3H), 1.12 (d, J = 7.0 Hz, 3H), 1.10-0.90 (m, 1H), 0.87 (d, J = 6.5 Hz, 3H), 0.87 (d, J = 7.0 Hz, 3H), 0.84 (d, J = 7.0 Hz, 3H), 0.82 (d, J = 7.0 Hz, 3H).
$^{13}$C NMR (125 MHz, CDCl$_3$) δ 176.65, 174.20, 163.80, 121.99, 111.75, 86.52, 81.83, 75.33, 73.00, 61.83, 58.02, 39.57, 38.19, 37.25, 35.93, 35.02, 34.48, 32.43, 32.20, 30.53, 27.96, 27.24, 19.94, 19.21, 19.13, 18.37, 17.50, 15.39, 9.73, 9.51.
IR (neat) 2966 (m), 2935 (w), 2877 (w), 1754 (vs), 1726 (vs), 1658 (w), 1462 (w), 1396 (m), 1339 (m), 1191 (s), 1091 (s), 1026 (s), 944 (m), 807 (w) cm$^{-1}$.
HRMS (ESI, [M + H]$^+$) calcd for C$_{30}$H$_{54}$O$_7$N 540.3894, found 540.3892.

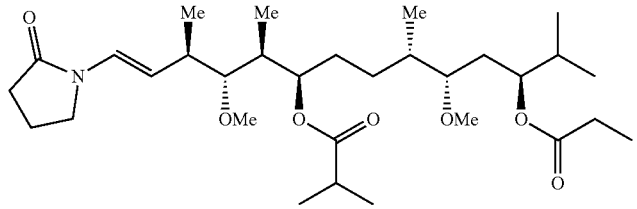

MA-02-044

$[\alpha]_D^{20}$ −37.0 (c = 0.5, CHCl$_3$).
$^1$H NMR (500 MHz, CDCl$_3$) δ 6.87 (d, J = 15.0 Hz, 1H), 5.16 (t, J = 7.0 Hz, 1H), 4.97 (dd, J = 8.5, 4.0 Hz, 1H), 4.93 (dd, J = 14.7, 9.2 Hz, 1H), 3.53-3.47 (m, 2H), 3.41 (d, J = 0.5 Hz 3H), 3.35 (d, J = 0.5 Hz, 3H), 2.89 (dt, J = 8.5, 3.5 Hz, 1H), 2.77 (d, J = 10.0 Hz, 1H), 2.55 (septet, J = 6.7 Hz, 1H), 2.46 (t, J = 7.7 Hz, 2H), 2.45-2.40 (m, 1H), 2.32 (app. q, J = 7.5 Hz, 2H), 2.07 (quin., J = 7.2 Hz, 2H), 1.82-1.76 (m, 1H), 1.73-1.68 (m, 1H), 1.67-1.62 (m, 1H), 1.60-1.48 (m, 3H), 1.48-1.30 (m, 3H), 1.18-1.20 (m, 12H), 0.98-0.91 (m, 1H), 0.87 (d, J = 6.5 Hz, 6H), 0.83 (d, J = 6.5 Hz, 3H), 0.83 (d, J = 6.5 Hz, 3H).
$^{13}$C NMR (125 MHz, CDCl$_3$) δ 176.65, 174.18, 172.90, 123.92, 112.59, 86.64, 81.83, 75.33, 73.07, 61.82, 58.01, 45.32,

TABLE 2-continued

Structure and Characterization Data 39.59, 37.95, 35.03, 34.48, 32.44, 32.19, 31.32, 30.49, 27.95, 27.24, 20.32, 19.20, 19.12, 18.36, 17.50, 15.35, 9.70, 9.49.
IR (neat) 2967 (m), 2934 (w), 2876 (w), 1726 (s), 1702 (vs), 1657 (w), 1461 (w), 1406 (m), 1270 (m), 1190 (s), 1091 (s), 962 (m) cm$^{-1}$.
HRMS (ESI, [M + H]$^+$) calcd for $C_{31}H_{56}O_7N$ 554.4051, found 554.4066.

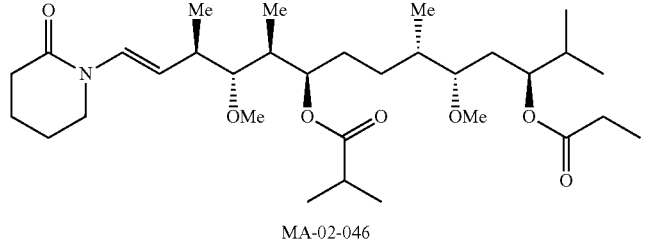 [SMILES: CCC(=O)O[C@@H](C[C@H](OC)[C@@H](C)CC[C@@H](OC(=O)C(C)C)[C@H](C)[C@H](OC)[C@H](C)/C=C/N1CCCCC1=O)C(C)C]

MA-02-046

$[\alpha]_D^{20}$ −34.2 (c = 0.4, CHCl$_3$).
$^1$H NMR (500 MHz, CDCl$_3$) δ 7.39 (d, J = 15.0 Hz, 1H), 5.16 (td, J = 7.0, 1.0 Hz, 1H), 5.00 (dd, J = 14.5, 9.5 Hz, 1H), 4.98-4.95 (m, 1H), 3.42 (s, 3H), 3.41-3.33 (m, 2H), 3.28 (s, 3H), 2.89 (dt, J = 9.0, 3.2 Hz, 1H), 2.77 (dd, J = 10.0, 2.0 Hz, 1H), 2.55 (septet, 2H = 7.0 Hz, 1H), 2.50-2.42 (m, 1H), 2.46 (t, J = 6.5 Hz, 2H), 2.35 (app. q, J = 7.5 Hz, 2H), 1.89-1.82 (m, 2H), 1.81-1.73 (m, 3H), 1.72-1.68 (in, 1H), 1.64-1.60 (m, 1H), 1.58-1.50 (m, 3H), 1.48-1.39 (m, 1H), 1.17 (d, J = 7.0 Hz, 3H), 1.17 (d, J = 7.0 Hz, 3H), 1.15 (t, J = 7.5 Hz, 3H), 1.14 (d, J = 7.0 Hz, 3H), 0.99-0.90 (m, 1H), 0.88 (d, J = 7.0 Hz, 3H), 0.88 (d, J = 7.0 Hz, 3H), 0.83 (d, J = 6.5 Hz, 6H).
$^{13}$C NMR (125 MHz, CDCl$_3$) δ 176.69, 174.20, 168.28, 126.96, 111.56, 86.71, 81.83, 75.32, 73.14, 61.86, 58.04, 45.18, 39.60, 38.24, 35.07, 34.49, 32.93, 32.45, 32.20, 30.50, 27.96, 27.22, 22.60, 20.58, 19.22, 19.14, 18.38, 17.51, 15.35, 9.66, 9.51.
IR (neat) 2963 (m), 2934 (w), 2874 (w), 1726 (s), 1665 (m), 1645 (m), 1460 (m), 1410 (w), 1263 (m), 1191 (s), 1161 (s), 1085 (s), 965 (m) cm$^{-1}$.
HRMS (ESI, [M + H]$^+$) calcd for $C_{32}H_{58}O_7N$ 568.42078, found 568.42053.

We claim:

1. A compound of Formula (1),

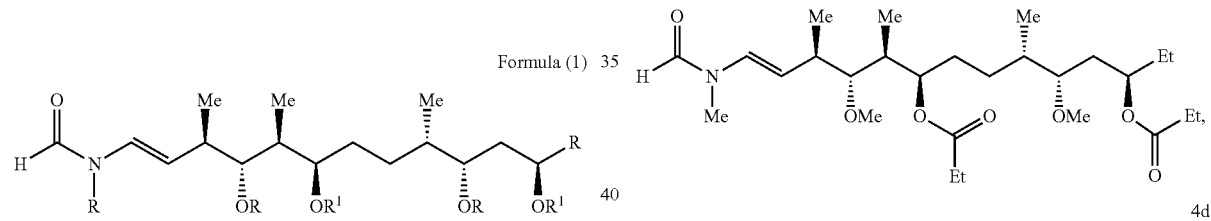

wherein

R$^1$ is independently —C(=O)R, —C(OR)(R)(R), —C(=O)NR$^2$R$^3$, —S(O$_2$)NR, —P(=O)(OR)$_2$, aliphatic moiety or aryl moiety, and R, R$^2$, and R$^3$ are independently a substituted or unsubstituted aliphatic moiety, or a substituted or unsubstituted aryl moiety, that optionally includes one or more heteroatoms.

2. A compound selected from compound 4a, 4b, 4c, 4d, 4e, 4f, 4g, 4h, 11, 12, MA-02-058, MA-02-047, MA-02-044, or MA-02-046 as shown below

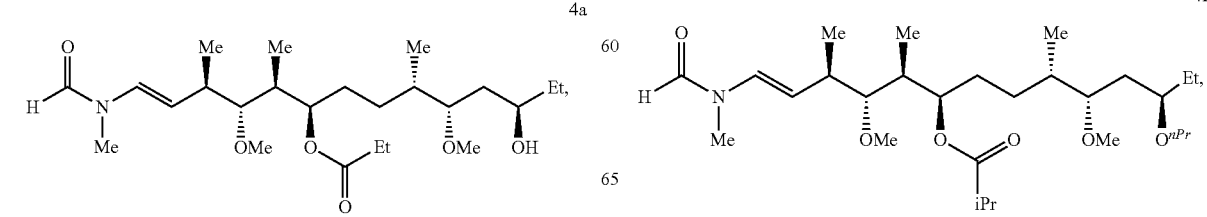

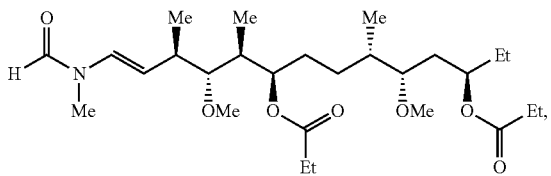
4c
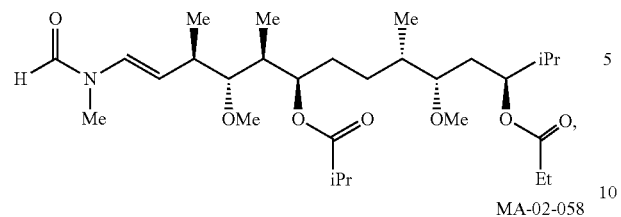
4g
MA-02-058
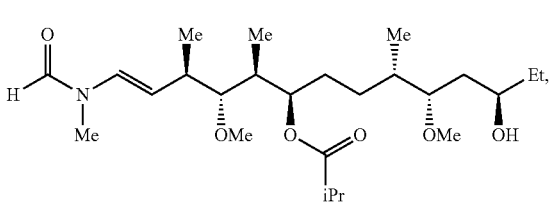
4d
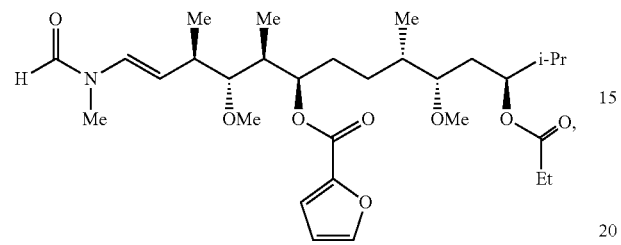
MA-02-047
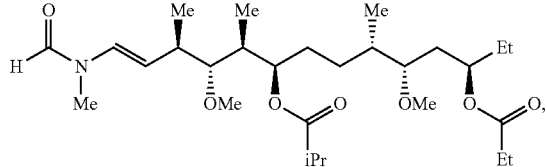
4e
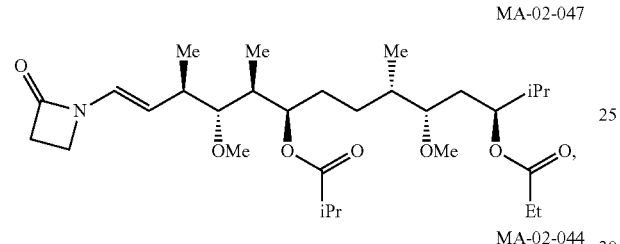
MA-02-044
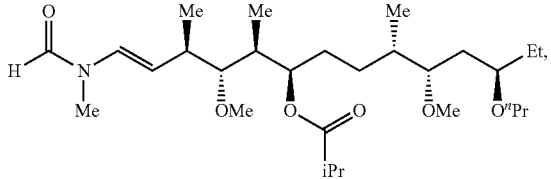
4f
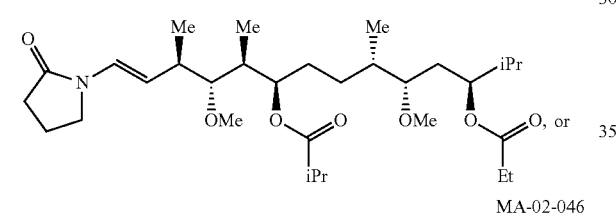
MA-02-046
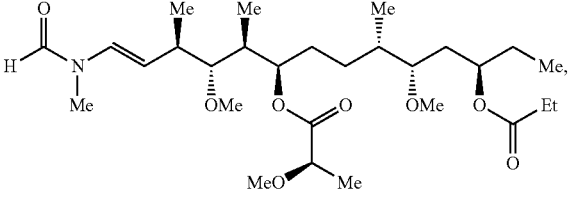
11
3. A pharmaceutical composition, comprising an effective amount of a compound of Formula (1) of claim 1 and a pharmaceutically acceptable vehicle.
4. A pharmaceutical composition comprising compound 4a, 4b, 4c, 4d, 4e, 4f, 4g, 4h, 11, 12, MA-02-058, MA-02-047, MA-02-044, MA-02-046, or a pharmaceutically acceptable salt thereof, and further comprising a pharmaceutically acceptable vehicle
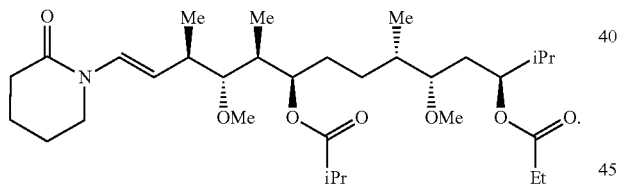
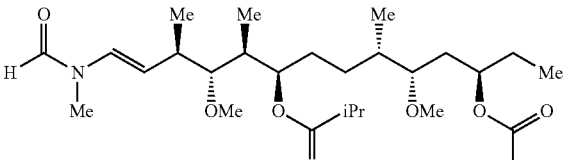
12
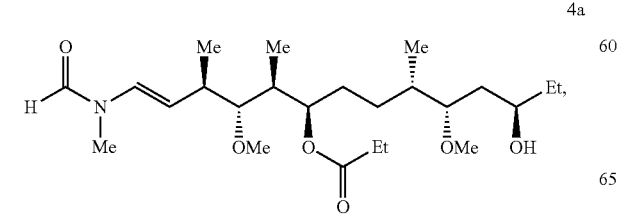
4a
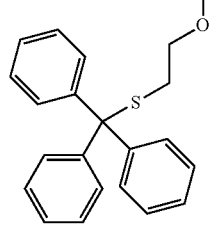

-continued

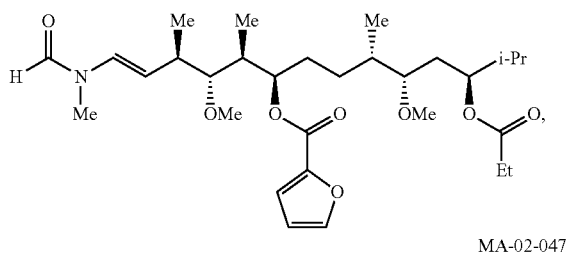

MA-02-058

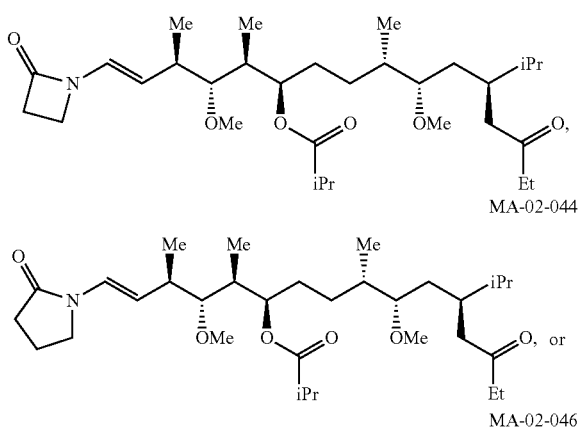

MA-02-047

MA-02-044

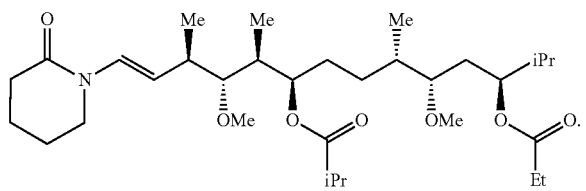

MA-02-046

5. The pharmaceutical composition of claim 3, is used for the treatment and/or mitigation of cancer.

6. The pharmaceutical composition of claim 5, wherein the cancer is metastatic cancer.

7. The pharmaceutical composition of claim 6, wherein the metastatic cancer is breast cancer, ovarian cancer, lung cancer, pancreatic cancer, melanoma, colorectal cancer, kidney cancer, cervical cancer, testicular cancer, or liver cancer.

8. The pharmaceutical composition of claim 3 is used for suppressing metastatic cancer cell motility, survival, or both.

9. The pharmaceutical composition of claim 3, further comprising one or more antineoplastic agent(s).

10. The pharmaceutical composition of claim 3, wherein the pharmaceutical composition further comprises a protein or a glycosaminoglycan.

11. The pharmaceutical composition of claim 10, wherein the protein is an antibody, hemoglobin, alphafeto-protein, fibrinogen, or serum albumin.

12. The pharmaceutical composition of claim 10, wherein the glycosaminoglycan comprises hyaluronic acid.

13. A method of treating and/or mitigating cancer, a cell proliferation disorder, or an actin-related disorder, comprising administering to a subject the pharmaceutical of claim 3.

14. A method of inhibiting actin in a subject in need thereof, comprising administering to the subject the compound of Formula (1) of claim 1.

15. The method of claim 14, wherein the subject has inflammatory lung disease.

16. A method for reducing actin released into circulation upon cellular damage, comprising administering the pharmaceutical composition of claim 3, to a subject in need thereof.

17. The method of claim 16, wherein the cellular damage was caused by stroke, or an adverse cardiovascular problem.

18. A method of suppressing tumor growth, metastasis, or both, comprising administering the pharmaceutical composition of claim 3, to a subject in need thereof.

19. A method of inhibiting actin in a subject in need thereof, comprising administering to the subject the pharmaceutical composition of claim 3.

20. A method of suppressing tumor growth, metastasis, or both, comprising administering the pharmaceutical composition of claim 4, to a subject in need thereof.

21. A method of treating and/or mitigating cancer, a cell proliferation disorder, or an actin-related disorder, comprising administering to a subject the pharmaceutical composition of claim 3.

* * * * *